United States Patent
Mersh et al.

(10) Patent No.: US 12,136,354 B2
(45) Date of Patent: Nov. 5, 2024

(54) VIRTUAL REALITY SIMULATION AND METHOD

(71) Applicant: Quality Executive Partners, Inc., Sandy Springs, GA (US)

(72) Inventors: Crystal Mersh, Sandy Springs, GA (US); Brian Duncan, Santa Fe, NM (US); Nicole Monachino, Alexandria, VA (US); Rebecca Brewer, Perkasie, PA (US); Robert Ferer, Charlotte, NC (US); Vanessa Figueroa, Riverdale, NY (US); Tyler DeWitt, New York, NY (US); Kenneth M. Wieber, St. Augustine, FL (US); Katayoun Meyer, Broomfield, CO (US); Scott Driscoll, Atlanta, GA (US); Michael Orndorff, Douglasville, GA (US)

(73) Assignee: Quality Executive Partners, Inc., Sandy Springs, GA (US)

( * ) Notice: Subject to any disclaimer, the term of this patent is extended or adjusted under 35 U.S.C. 154(b) by 0 days.

(21) Appl. No.: 18/387,232

(22) Filed: Nov. 6, 2023

(65) Prior Publication Data

US 2024/0087473 A1    Mar. 14, 2024

Related U.S. Application Data

(63) Continuation of application No. 17/278,913, filed as application No. PCT/US2019/056136 on Oct. 14, 2019, now Pat. No. 11,854,424.
(Continued)

(51) Int. Cl.
G09B 23/24    (2006.01)
G06T 19/00    (2011.01)
(Continued)

(52) U.S. Cl.
CPC ............ G09B 23/24 (2013.01); G06T 19/003 (2013.01); G09B 9/00 (2013.01); G16H 10/40 (2018.01); G16H 40/67 (2018.01)

(58) Field of Classification Search
CPC ... G09B 9/24; G09B 9/26; G09B 9/28; G09B 9/30; G09B 9/00; G16H 40/67; G16H 10/40; G06T 19/003
See application file for complete search history.

(56) References Cited

U.S. PATENT DOCUMENTS

| | | |
|---|---|---|
| 11,227,509 B2 | 1/2022 | Ueltschi |
| 2009/0177452 A1 | 7/2009 | Ullrich |

(Continued)

FOREIGN PATENT DOCUMENTS

| | | |
|---|---|---|
| JP | 2005-134536 A | 5/2005 |
| JP | 2011-502300 A | 1/2011 |
| WO | WO 2018/106289 | 6/2018 |

OTHER PUBLICATIONS

Examination Report No. 1 in corresponding Australian patent application No. 2019399480, issued Nov. 23, 2023. (2 pages).
(Continued)

Primary Examiner — Timothy A Musselman
(74) Attorney, Agent, or Firm — Watts Law LLC; Samantha R. Smart, Esq.

(57) ABSTRACT

One aspect of the present disclosure include a method and system for providing an interactive virtual reality simulation for virtual reality training. A headset, controllers, and/or one or more sensors communicate with a processor to display the interactive virtual reality simulation on a user display within the headset. The interactive virtual reality training for use in facilitating virtually reality simulations including a microscope simulation, a bacteria streaking simulation, and/or a visually inspecting containers simulation.

22 Claims, 66 Drawing Sheets

Related U.S. Application Data

(60) Provisional application No. 62/744,753, filed on Dec. 10, 2018.

(51) Int. Cl.
*G09B 9/00* (2006.01)
*G16H 10/40* (2018.01)
*G16H 40/67* (2018.01)

(56) References Cited

U.S. PATENT DOCUMENTS

| | | |
|---|---|---|
| 2011/0015913 A1 | 1/2011 | Yamashita |
| 2014/0315174 A1 | 10/2014 | Sassani |
| 2015/0000025 A1 | 1/2015 | Clements |
| 2016/0370971 A1 | 12/2016 | Hackett |
| 2018/0090029 A1 | 3/2018 | Fisher et al. |

OTHER PUBLICATIONS

European Search Report and Examination Report from corresponding application EP19895297.0, issued Aug. 26, 2022. (14 pages).
Japanese Office Action in corresponding application JP2021-5213578, issued Aug. 24, 2023. (1 page—English translation of prior art listing.).

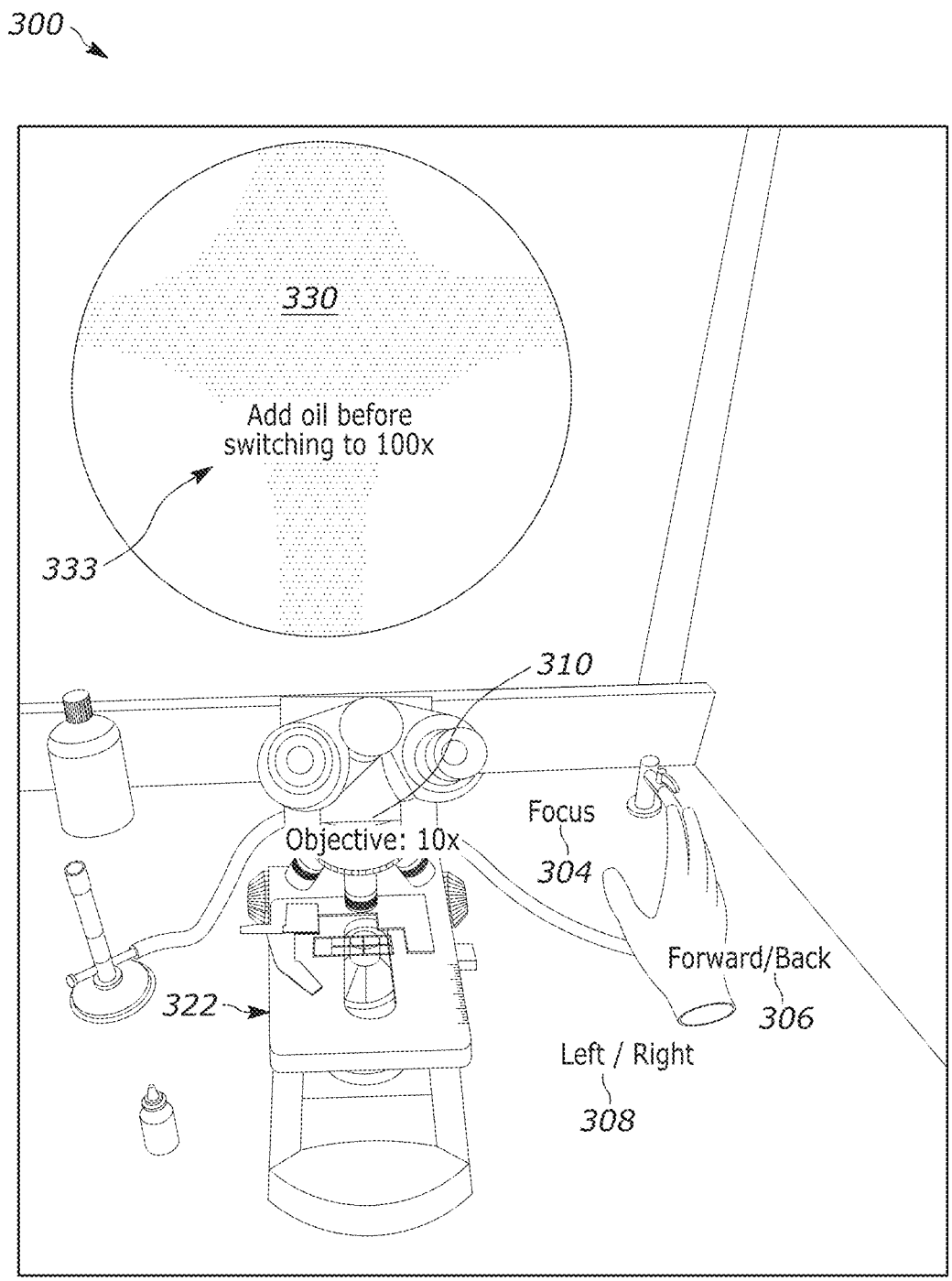
FIG. 3H1

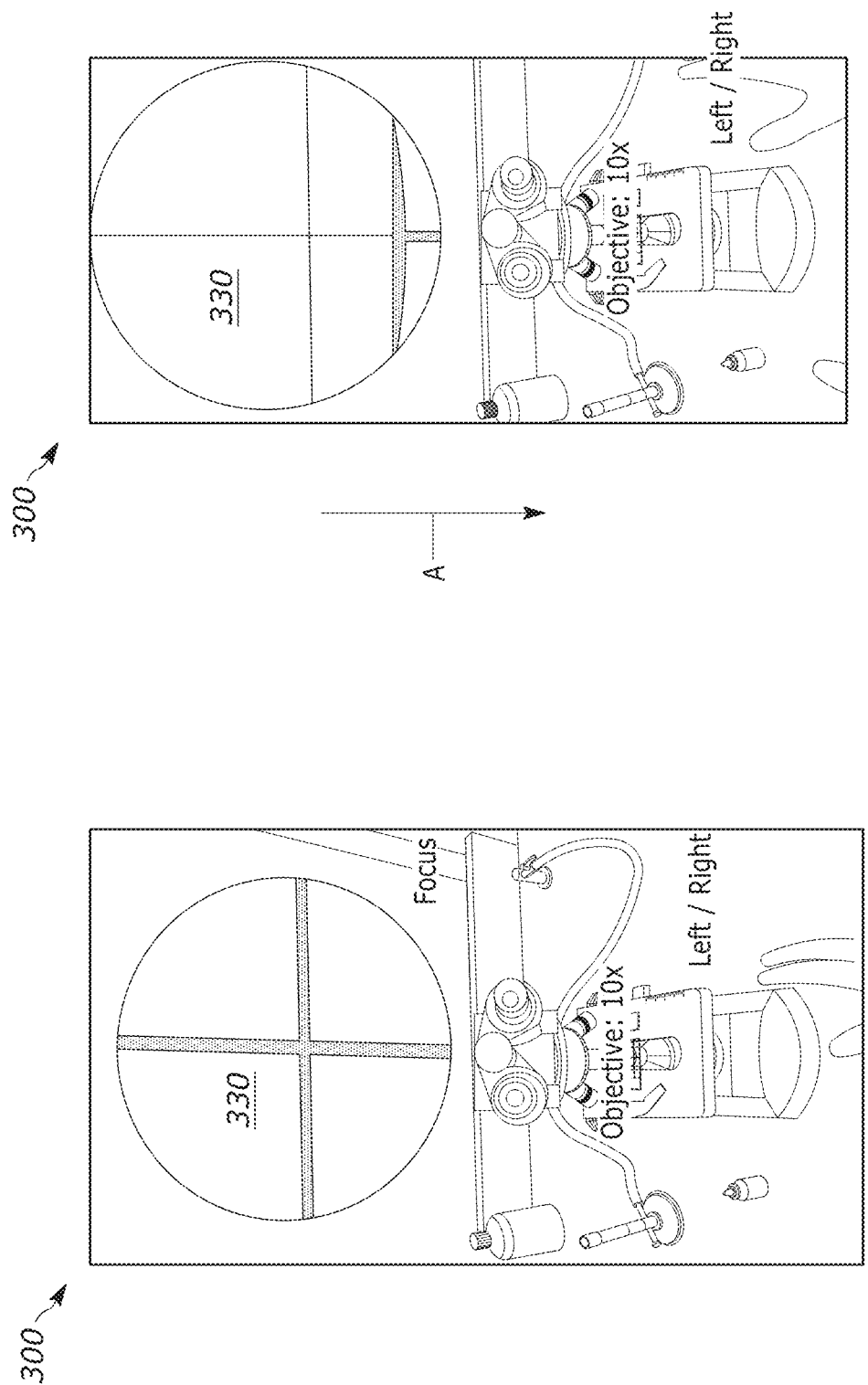

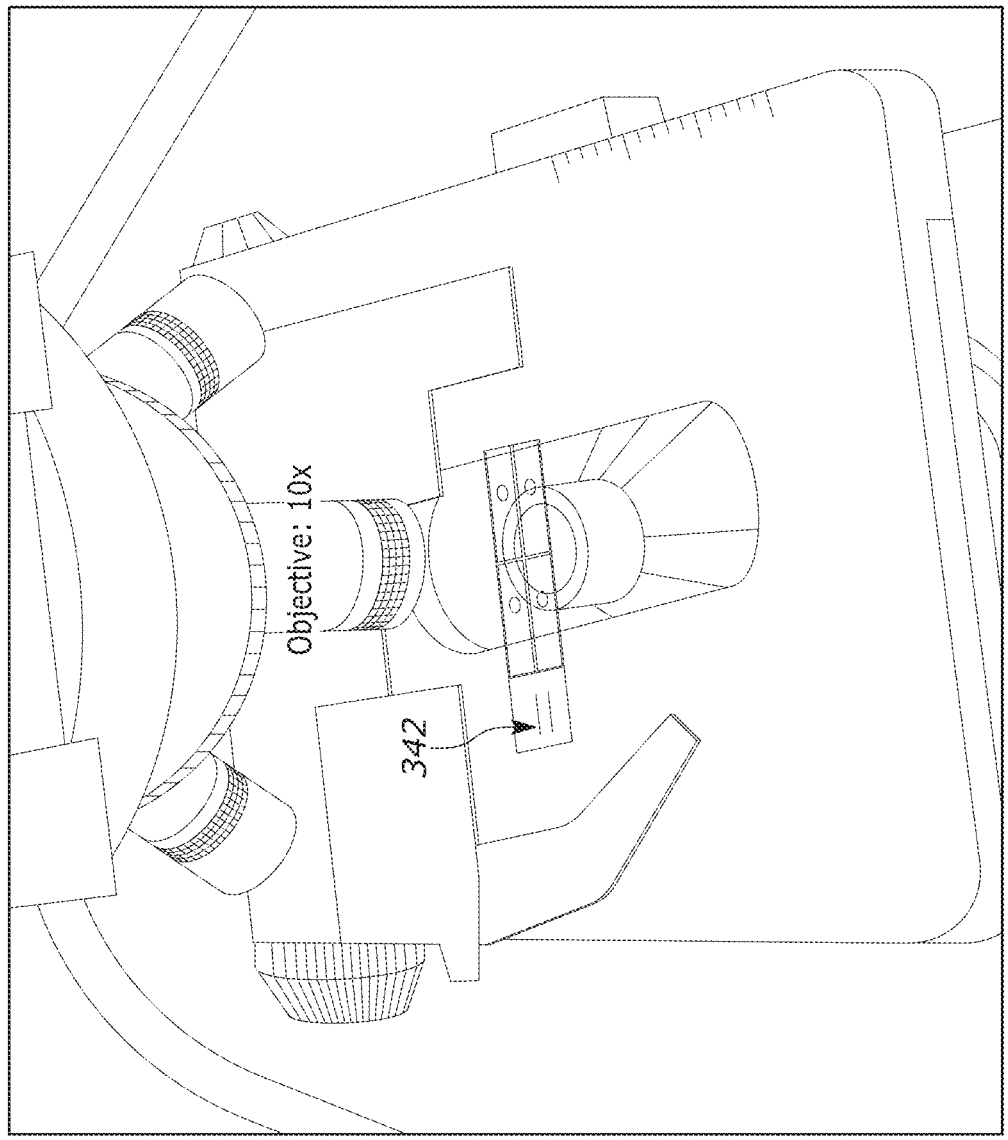
FIG. 3L3

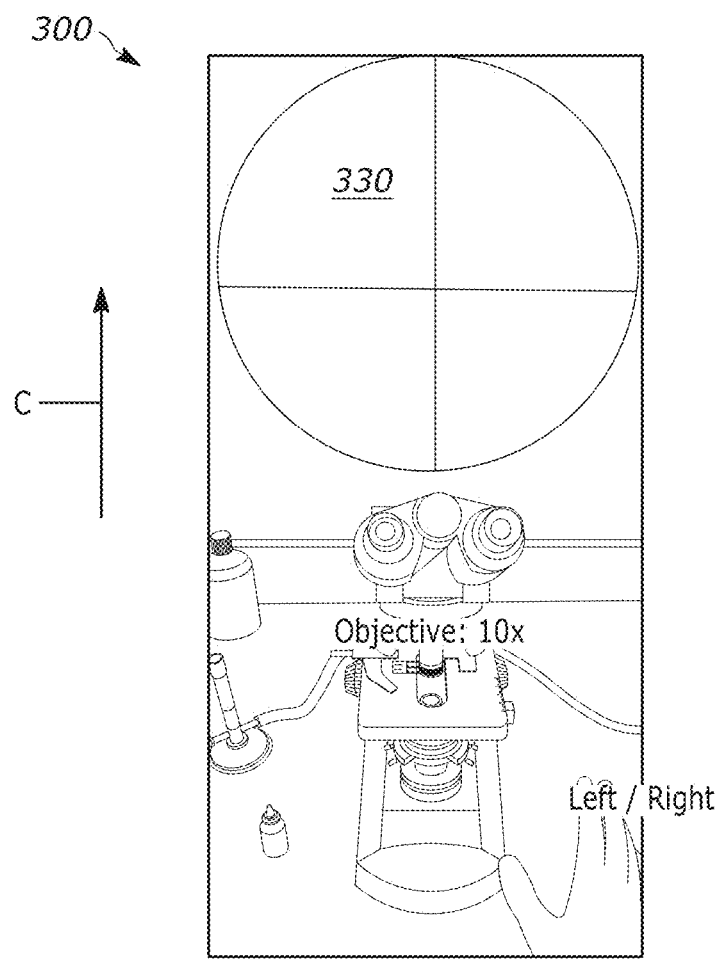
FIG. 3L4
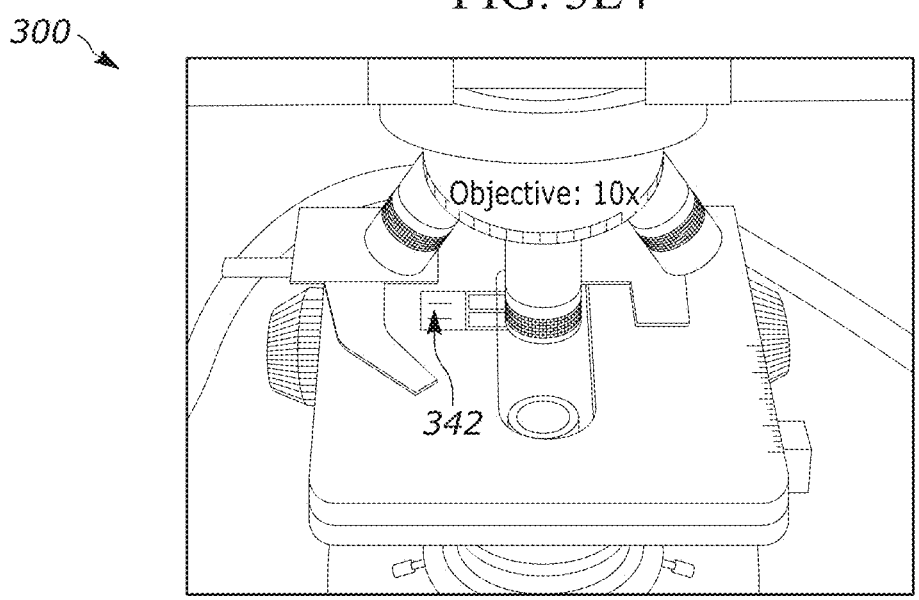
FIG. 3L5

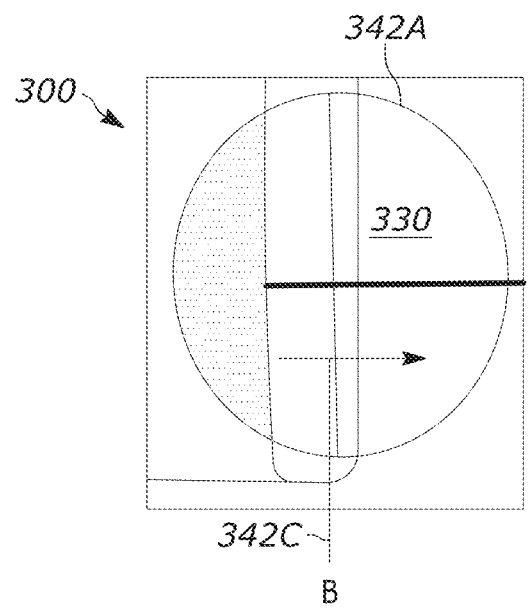
FIG. 3M
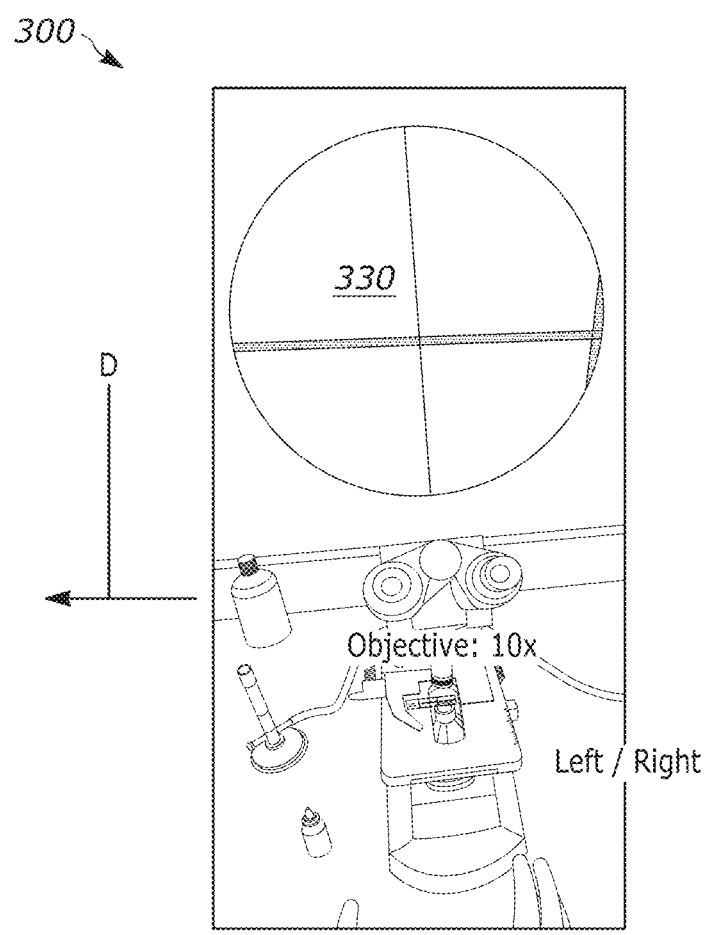
FIG. 3M1

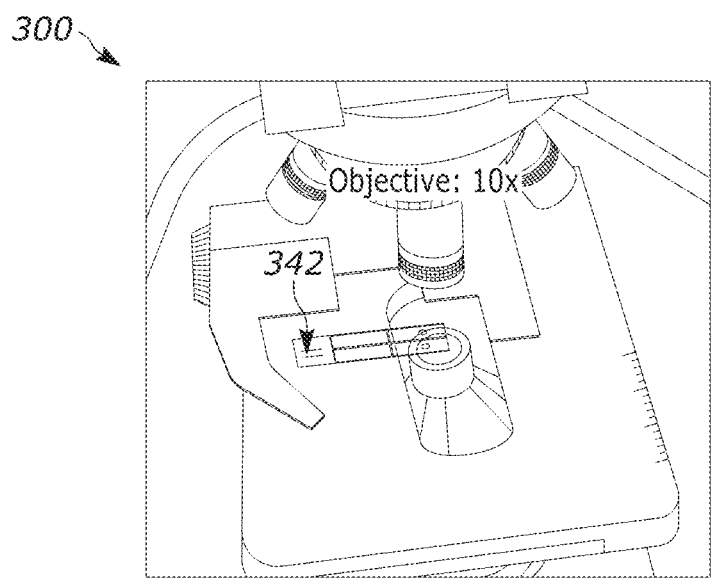
FIG. 3M2
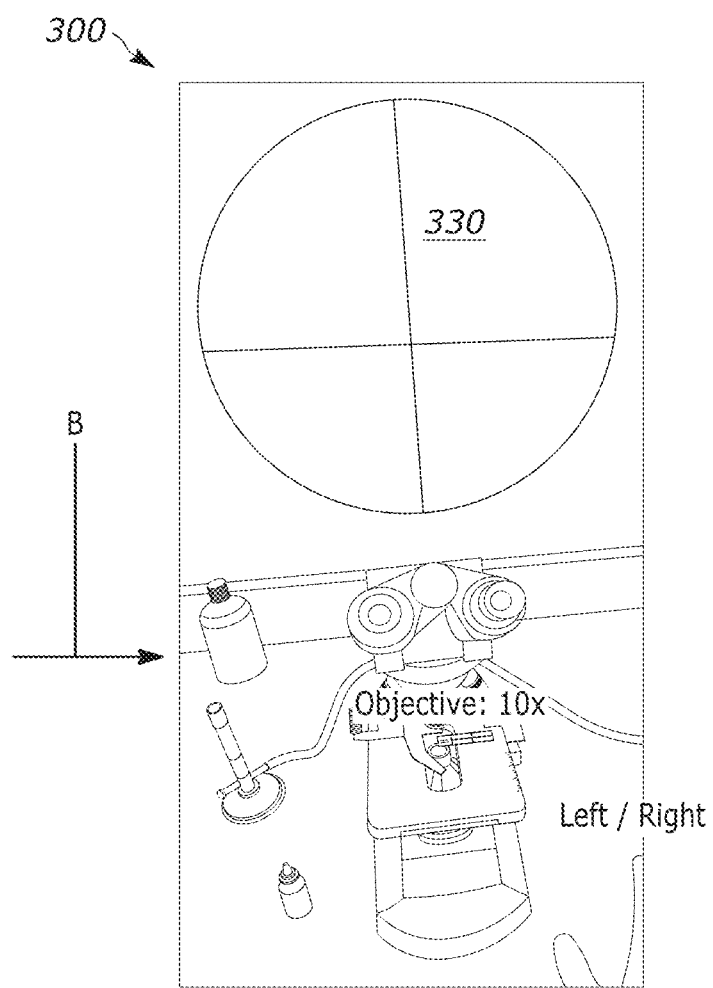
FIG. 3M3

VIRTUAL REALITY SIMULATION AND METHOD

CROSS REFERENCES TO RELATED APPLICATIONS

The following is a continuation application claiming priority under 35 U.S.C. § 120 to co-pending U.S. nonprovisonal application Ser. No. 17/278,913 that was filed on Mar. 23, 2021 and published on Feb. 10, 2022 under publication number US-2022-0044593 entitled VIRTUAL REALITY SIMULATION AND METHOD, which claims priority under 35 U.S.C. § 371 to international PCT application serial number PCT/US19/056,136 filed Oct. 14, 2019 entitled VIRTUAL REALITY SIMULATION AND METHOD that was published on Jun. 18, 2020, under international publication number WO/2019/123,026, which claims priority under 35 U.S.C. § 119 to U.S. Provisional Patent Application Ser. No. 62/744,753 filed Oct. 12, 2018 entitled SOFTWARE IMMERSIVE TOOL. Priority is claimed for all the above-identified applications and publication, all of which are incorporated herein by reference in their entireties for all purposes.

TECHNICAL FIELD

The present disclosure generally relates to an apparatus and methods for virtual reality training, and more particularly to methods and devices utilizing a processor device, visual outputs, sensor devices and special sensors combination for use in facilitating virtual reality simulations including a microscope simulation, a bacteria streaking simulation, and/or a visually inspecting containers simulation.

BACKGROUND

Training for laboratory situations, such as using a microscope, isolating a bacterial colony by streaking a plate, and/or visually inspecting containers for contaminates, is required for most workers in a laboratory and/or manufacturing environment. Real-world training can be time consuming (e.g., waiting for the bacteria to grow), expensive (e.g., microscopes can be damaged by improper use), and/or risky if students make mistakes on real products and contaminated containers get sent to hospitals and/or are used on patients. Further, in the real-world specific elements cannot be emphasized, or altered to better ingrain training. This is particularly the ease for training that requires extensive laboratory training time for various certification or degreed programs. Such training is both expensive in capital equipment, as well as requiring tear down, cleaning, and set-up costs.

SUMMARY

One aspect of the present disclosure comprises a non-transitory computer readable medium storing instructions executable by an associated processor to perform a method for implementing a bacteria streaking simulation comprising generating a three-dimensional initial view based upon a view selection input by a user, sending instructions to present the initial view to a user display of a headset, the user display comprised within the headset, receiving an input from a controller comprising at least one sensor indicating user movement within the initial view, and accessing memory to identify an assigned status of a loop. Responsive to the loop being coupled to a user icon within the initial view, storing a pattern of interaction between the loop and a streaking plate comprised within the initial view, storing the pattern comprising generating a series of waypoints and connecting them to comprise the pattern, and assigning a decreasing bacterial concentration to the loop, wherein the concentration of the loop at the location of a waypoint creation is assigned to the waypoint, wherein each progressive waypoint within the series of waypoints being created by the loop has a decreasing bacterial concentration. Responsive to the pattern of interaction overlapping one or more existing waypoint of one or more existing patterns, assigning an altered bacterial concentration to the loop based upon the assigned value of the one or more existing waypoint and the assigned bacterial concentration of the loop at the location bf the overlap and storing the series of waypoints and their assigned bacterial concentrations.

Another aspect of the present disclosure comprises a virtual reality system for providing a bacterial streaking simulation, the system comprising a processing device having a processor configured to perform a predefined set of operations in response to receiving a corresponding input frond at least one ok virtual reality headset and at least one controller, the processing device comprising memory, wherein a three-dimensional initial view of a bacterial streaking simulation is stored, the initial view comprising a streaking plate, a heating element, and a loop. The processor instructs the initial view to be presented on a user display comprised within the headset, the at least one controller sends an input to the processor indicating the controller is moving within the initial view, and the processor instructs the movement of the controller of the at least one controller be presented on the user display. Responsive to an input from the controller, the processor assigns the loop to be controlled by movement of the controller, the controller sends an input indicating that the controller is moving and interacting with the streaking plate, and the processor generates and stores a pattern of interaction between the loop and the streaking plate, wherein the processor generates the pattern by assigning a linearly decreasing bacterial concentration to the loop responsive to a distance traveled by said loop while interacting with the streaking plate, the processor generates a series of waypoints, wherein the bacterial concentration of the loop at the location of a waypoint creation is assigned to the waypoint, the processor instructs the user display to illustrate the waypoints as a line forming the pattern on the streaking plate. The processor generates a first rectangle extending toward a previous waypoint in the series bf waypoints and a second rectangle extending toward a next waypoint in the series of waypoints, the processor calculates a cell potential of the first and second rectangles based upon the assigned bacterial concentration of the waypoint. The processor randomly assigns cell placement with the first and second rectangles based upon the cell potential, and the processor simulates bacterial growth on the streaking plate based upon the cell placement within the first and second rectangles.

Yet another aspect of the present disclosure comprises a non-transitory computer readable medium storing instructions executable by an associated processor to perform a method for implementing a visual inspection simulation comprising generating a three-dimensional initial view based upon a view selection input by a user, sending instructions to present the initial view to a user display of a headset, the user display comprised within the headset, receiving an input from a controller comprising at least one sensor indicating user movement within the initial view, and accessing memory to identify an assigned status of a selected container of one or more containers. Responsive to an input from the controller, the processor assigns the selected container to be controlled by movement of the controller, continuously generating a fluid flow pattern utilizing a visualization state machine, wherein a single point mass on a mass spring with a lateral damper is virtually attached to a fixed point in a center of the container. Responsive to receiving an input from the controller that the container moved in a defined direction, swinging the single point mass back and forth along the defined direction then settling the single point mass into an original position, and displaying a two-dimensional liquid top surface as following the orientation of the single point mass, wherein the liquid top surface is continually oriented to face a line of sight from the user display.

Yet another aspect of the present disclosure comprises a virtual reality system for providing a visual inspection simulation, the system comprising a processing device having a processor configured to perform a predefined set of operations in response to receiving a corresponding input front at least one of virtual reality headset and at least one controller, the processing device comprising memory, wherein a three-dimensional initial view of a visual inspection simulation is stored, the initial view comprising at least one container, the processor instructs the initial view to be presented on a user display comprised within the headset, and the at least one controller sends an input to the processor indicating the controller is moving within the initial view. The processor instructs the movement of the controller of the at least one controller be presented on the user display. Responsive to an input from the controller, the processor assigns a selected container of the at least one container to be controlled by movement of the controller, the controller sends an input indicating that the controller is moving the selected container, and the processor generates a continuous fluid flow pattern utilizing a visualization state machine, wherein the visualization state machine comprises a single point mass on a mass spring with a lateral damper virtually attached to a fixed point in a center of the container. The controller sends a signal to the processor that the container moved in a defined direction, and the processor swings the single point mass back and forth along the defined direction then has the single point mass settle into an initial position, wherein the processor instructs the user display to display a two-dimensional liquid top surface as following the orientation of the single point mass, wherein the process instructs the user display to display the liquid to surface to be continually oriented to face a line of sight.

Yet another aspect of the present disclosure comprises a non-transitory computer readable medium storing instructions executable by an associated processor to perform a method for implementing a microscope simulation comprising generating a three-dimensional initial view based upon a view selection input by a user, sending instructions to present the initial view to a user display of a headset, the user display comprised within the headset, receiving an input from a controller comprising at least one sensor indicating user movement within the initial view, and accessing memory to identify an assigned status of a microscope including lateral wheel, longitudinal wheel, objective wheel and focus wheel inputs. Responsive to an input from the controller, instructing the user display to display one of the lateral wheel, the longitudinal wheel, the objective wheel and the focus wheel. Wherein responsive to a slide present on the microscope being assigned bacteria, retrieving bacteria from memory and instructing the user display to display the bacteria on the slide present on the microscope and on a heads-up display displaying a microscope view. Responsive to the controller sending a signal that the controller is moving and interacting with the objective wheel, instructing the user display to display the objective wheel rotating based upon the controller movement and to display the heads-up display displaying a microscope view having an altered magnification and responsive to the controller sending a signal that the controller is moving and interacting with the focus wheel, instructing the user display to display the focus wheel rotating based upon the controller movement and to display the heads-up display displaying the microscope view having an altered blurriness, wherein the slide and the bacteria are presented as having the altered blurriness.

Yet another aspect of the present disclosure comprises a virtual reality system for providing a microscope simulation, the system comprising a processing device having a processor configured to perform a predefined set of operations in response to receiving a corresponding input front at least one of virtual reality headset and at least one controller, the processing device comprising memory, wherein a three-dimensional initial view of a microscope simulation is stored, the initial view comprising a microscope. The processor instructs the initial view to be presented on a user display comprised within the headset, the at least one controller sends an input to the processor indicating the controller is moving within the initial view, and the processor instructs the movement of the controller of the at least one controller be presented on the user display. Responsive to an input from the controller, the processor instructs the user display to display one of the lateral wheel, the longitudinal wheel, the objective wheel and the focus wheel, wherein responsive to the processor having assigned a slide present on the microscope no bacteria, the processor retrieves a blank slide from memory and instructs the user display to display the slide present on the microscope and on a heads-up display displaying a microscope view. Responsive to the controller sending a signal that the controller is moving and interacting with the objective wheel, the processor instructs the user display to display the objective wheel rotating based upon the controller movement and to display the heads-up display displaying the microscope view having an altered magnification, and responsive to the controller sending a signal that the controller is moving and interacting with the focus wheel, the processor instructs the user display to display the focus wheel rotating based upon the controller movement and to display the heads-tip display displaying the microscope view having an altered blurriness, wherein the slide is presented as having the altered blurriness.

BRIEF DESCRIPTION OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which:

FIG. 3H1 illustrates a view of a microscope simulation utilizing an oil dropper interactive functionality generated by an example virtual reality system, according to one example embodiment of the present disclosure;

FIG. 3L1 illustrates a microscope view corresponding to a view of a slide, wherein the view of the slide is at an initial position on a microscope of a microscope simulation generated by an example virtual reality system, according to one example embodiment of the present disclosure;

FIG. 3L2 illustrates a microscope view corresponding to a view of a slide, wherein the view of the slide has been altered to a maximum forward position through use of the lateral wheel present on a microscope of a microscope simulation generated by an example virtual reality system, according to one example embodiment of the present disclosure;

FIG. 3L3 illustrates a view of a slide, wherein the view of the slide has been altered to a maximum forward position through use of the lateral wheel present on a microscope of a microscope simulation generated by an example virtual reality system, according to one example embodiment of the present disclosure;

FIG. 3L4 illustrates a microscope view corresponding to a view of a slide, wherein the view of the slide has been altered to a maximum rear position through use of the lateral wheel present on a microscope of a microscope simulation generated by an example virtual reality system, according to one example embodiment of the present disclosure;

FIG. 3L5 illustrates a view of a slide, wherein the view of the slide has been altered to a maximum rear position through use of the lateral wheel present on a microscope of a microscope simulation generated by an example virtual reality system, according to one example embodiment of the present disclosure;

FIG. 3M illustrates a microscope view corresponding to a view of a slide wherein the view of the slide has been altered through use of the longitudinal wheel present on a microscope of a microscope simulation generated by an example virtual reality system, according to one example embodiment of the present disclosure;

FIG. 3M1 illustrates a microscope view corresponding to a view of a slide wherein the view of the slide has been altered to a maximum left position through use of the longitudinal wheel present on a microscope of a microscope simulation generated by an example virtual reality system, according to one example embodiment of the present disclosure;

FIG. 3M2 illustrates a view of a slide wherein the view of the slide has been altered to a maximum left position through use of the longitudinal wheel present on a microscope of a microscope simulation generated by an example virtual reality system, according to one example embodiment of the present disclosure;

FIG. 3M3 illustrates a microscope view corresponding to a view of a slide wherein the view of the slide has been altered to a maximum right position through use of the longitudinal wheel present on a microscope of a microscope simulation generated by an example virtual reality system, according to one example embodiment of the present disclosure;

FIG. 3M4 illustrates a view of a slide wherein the view of the slide has been altered to a maximum right position through use of the longitudinal wheel present on a microscope of a microscope simulation generated by an example virtual reality system, according to one example embodiment of the present disclosure;

FIG. 5O1 illustrates a-loop containing a source colony in-a streaking simulation generated by an example virtual reality system, according to one example embodiment of the present disclosure;

FIG. 5P1 illustrates a streaking simulation including a streaking plate having a streaking cap removed, a source plate, and a loop generated by an example virtual reality system, according to one example embodiment of the present disclosure;

Figure 1:
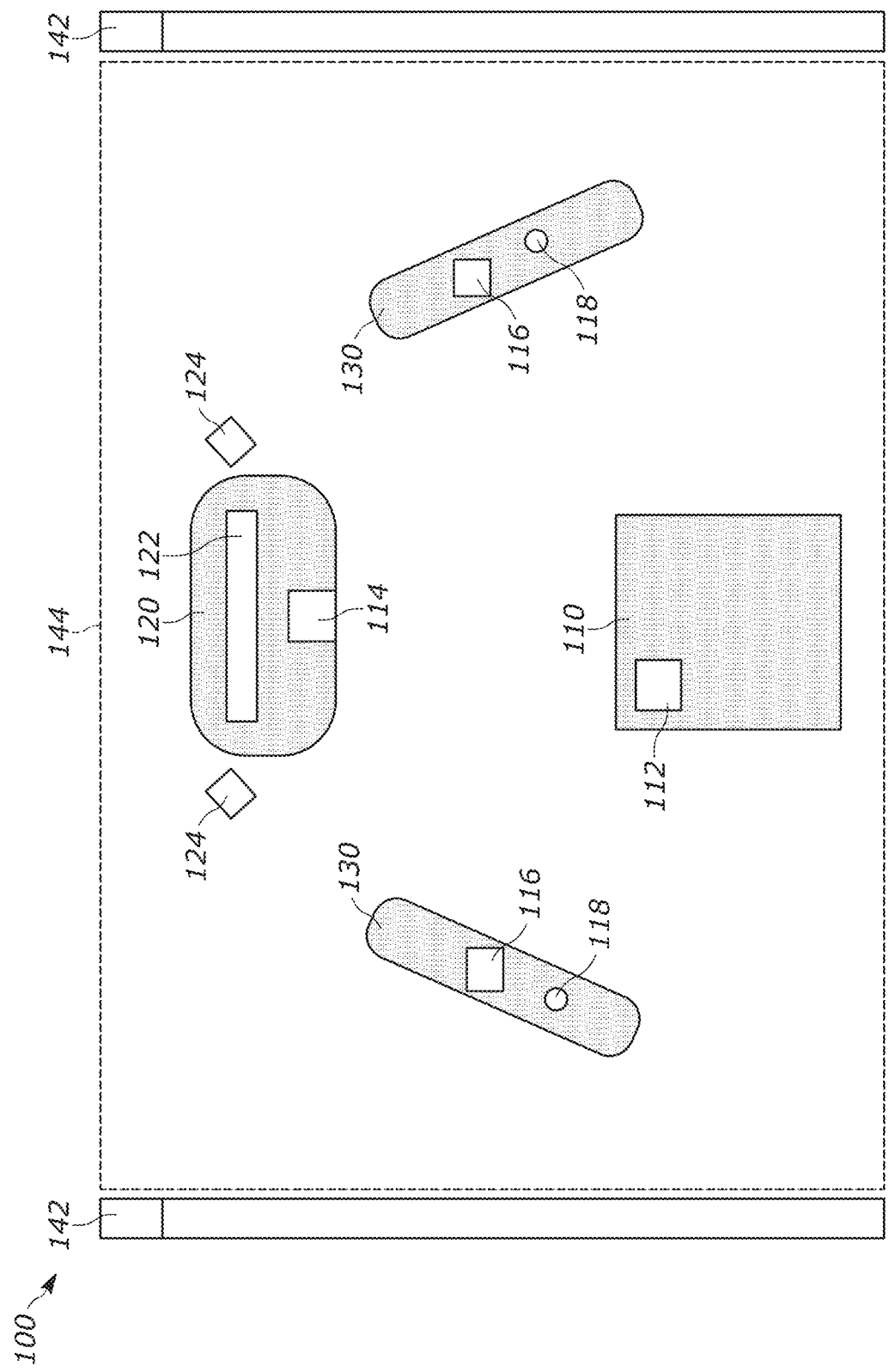
FIG. 1 illustrates an example virtual reality system, according to one example embodiment of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Referring now to the figures generally wherein like numbered features shown therein refer to like elements throughout unless otherwise noted. The present disclosure generally relates to an apparatus and methods for virtual reality training, and more particularly to methods and devices utilizing a processor device, visual outputs, sensor devices and special sensors combination for use in facilitating virtual reality simulations including a microscope simulation, a bacteria streaking simulation, and/or a visually inspecting containers simulation.

FIG. 1 illustrates a schematic diagram of a virtual reality system 100, in accordance with one of the exemplary embodiments of the disclosure. The virtual reality system 100 includes a-processing device 110, a virtual reality headset, "headset 120", and at least one controller 130, where the processing device 110 is connectable and/or connected to the virtual reality headset 120 and the controller 130.

In one example embodiment, the processing device 110 includes a computing device (e.g. a database server, a file server, an application server, a computer, or the like) with computing capability and/or a processor 112. The processor comprises, a field programmable array (FPGA), a programmable logic device (PLD), an application specific integrated circuit (ASIC), a North Bridge, a South Bridge and/or other similar device or a combination thereof. The processor 112, may for example, comprise central processing unit (CPU), a programmable general purpose or special purpose microprocessor, a digital signal processor (DSP), a graphics processing unit (GPU), and/or other similar device or a combination thereof.

The processing device 110 would generate images, audio, text, etc. that replicate a environments found in the real world, and/or environments generated to be perceived as the real world. The processing device 110 is in two-way communication with the virtual reality headset 120 and the at least one controller 130, wherein the headset and controller provide inputs to the processing device 110 that provides data about the user's actions and motions. The processing device 110 provides instructions to generate visual, audio, and/or text responsive to the inputs received, such that the user navigates and interacts with the virtual world. In one example embodiment, the processing device 110 is integrated with the virtual reality headset 120. In another example embodiment, the processing device 110 is in wired and/or wireless connection with the virtual reality headset 120.

It would be appreciated by having ordinary skill in the art that the processing device 110 would include a data storage device in various forms of non-transitory, volatile, and non-volatile memories which would store buffered or permanent data as well as compiled programming codes used to execute functions of the processing device 110. In another example embodiment, the data storage device can be external to and accessible by the processing device 110, the data storage device may comprise an external hard drive, cloud storage, and/or other external recording devices.

In one example embodiment, the processing device 110 is a remote computer system. The computer system includes desktop, laptop, tablet hand-held personal computing device, IAN, WAN, WW, and the like, running on any number of known operating systems and are accessible for communication with remote data storage, such as a cloud, host operating computer, via a world-wide-web or Internet. In one example embedment, the controller 130 and VR (virtual reality) headset 120 both contain transceivers for sending and receiving instructions.

In another example embodiment, the processing device 110 comprises a processor, a data storage, computer system memory that includes random-access-memory ("RAM"), read-only-memory ("ROM") and/or an input/output interface. The processing device 110 executes instructions by non-transitory computer readable medium either internal or external through the processor that communicates to the processor via input interface and/or electrical communications, such as from a secondary device (e.g., smart phone, tablet, or other device) the controller 130 and/or the headset 120. In yet another example embodiment, the processing device 110 communicates with the Internet, a network such as a LAN, WAN, and/or a cloud, input/output devices such as flash drives, remote devices such as a smart phone or tablet, and displays.

The virtual reality headset 120 would be a head-mounted display or goggles 122 with a build in head-tracking system. An example headset 120 made by Facebook part #Quest, which is incorporated by reference in its entirety for all purposes. The virtual reality headset 120 includes the integrated display 122, a headset motion sensor 114, a communication interface, and/or a user speakers 124, and a built-in processor for executing or reading instructions from memory, or an input for providing instructions to an output.

The display 122 may comprise one of a liquid crystal display (LCD), a light-emitting diode (LED) display, or the like. The motion sensor 114 may comprise a combination of an accelerometer (e.g. G-sensor), a gyroscope (e.g. gyrosensor), and/or a sensor that detects the linear and/or rotational movement (e.g. rotational angular velocity or rotational angle) of the headset 120. In another example embodiment, the motion sensor includes one or more locators 142 that generate a motion sensing grid 144, wherein motion of the controller 130 and/or the headset 120 is monitored, and identified by the one or more sensors. The controller 130 and/or the headset 120 include one or more sensed volumes, such that the motion sensing grid senses linear and/or rotational movement. The locator 142 includes, for example, a laser or an infrared transmitter and receiver. The locator 142 maps where the virtual reality headset 120 and the controller 130 are in three dimensional space. Further, the locators 142 via instruction from the processor 112 define boundaries of the virtual space to prevent the user from bumping into walls or collisions with physical objects while in the virtual world.

In one example embodiment, the locator 142 comprises base stations including, for example, a spinning laser sheet. Sensors 114, 116 on the headset 120 and controllers 130 detect transmit to the processor 112 when (e.g., a specific time) the laser sheet passes various points on the headset 120 and/or the controller 130. The processor 112, utilizing a time the various points were detected, triangulates position and orientation of the controller 130 and/or headset 120 from the times. In another example embodiment, the sensor 114 of the headset 120 (e.g., an Oculus Rift S of an Oculus Quest headset) comprises onboard cameras that transmit data to the processor 112, or comprising processing power themselves to calculate position and orientation via photogrammetry. In yet another example embodiment, the locator 142 comprises one or more cameras that detect lights that are projected from the headset 120 and controllers.

In the illustrated example embodiment, the headset 120 outputs headset motion data to the processing device 110 (e.g., via the locator 142, and/or motion sensors) and the processor 112 of the processing device instruct the headset to display images on the user display 122 that correlate the headset motion data (e.g., the user turns their head left, and the display alters to show a volume leftward of the user's original gaze).

In the illustrated example embodiment of FIG. 1, the controller 130 comprises a handheld controller. In one example embodiment, the controller 130 is equipped with a handheld motion sensor 116, a tactile element 118, for example, a mouse, a joystick, a trackball, a touch pad, and/or buttons that permits the user to interact with environment, objects, or avatars in the virtual world (the virtual world is what is being displayed in the headset 120 based upon movement of the headset, the controller, and based upon instructions processed by processor 112, and or controller 130, these instructions are received by their respective inputs and processed by respective processor to provide non-transitory instructions to the respective devices 120, 130). In one example embodiment, such instructions are non-transitory, such as computer readable media, that can be transmitted to the devices of the system 100 to be processed on the respective processor of the respective devices 120, 130. The controller 130 communicates with the processing device 110, the locators 142, and/or the headset 120 via any wireless standard and/or is in wired communication with the processing device 110. It would be appreciated by one having ordinary skill in the art that handheld motion sensor includes sensors 116 located on the controller 130, and/ok sensible elements that are sensed by other devices, such as the locator 142.

Figure 2:
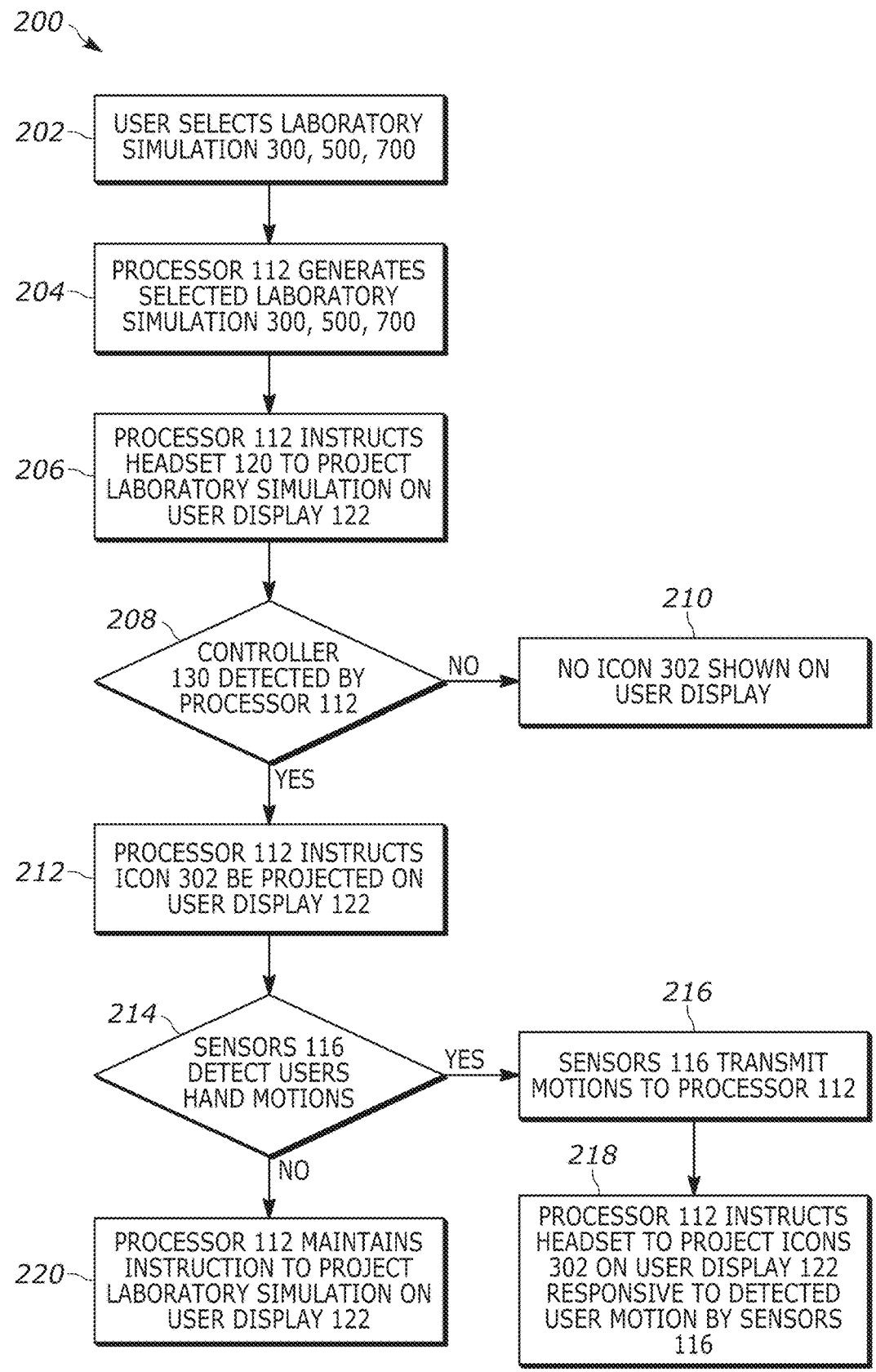
FIG. 2 is a schematic diagram of a method of using an example virtual reality system, according to one example embodiment of the present disclosure.

As illustrated in FIG. 2, a method 200 of use of the virtual reality system 100 is illustrated. At 202, a user, utilizing the virtual reality system 100 selects a laboratory simulation 300, 500, 700. In this example embodiment, the user has access to a plurality of laboratory simulations which will be discussed in greater detail below. The user may select the laboratory simulation 300, 500, 700 utilizing the controller 130 and/or the tactile element 118 of the controller, the processing unit 110 (e.g., a mouse, keyboard, or the like in communication with the processing unit), and/or through eye and/or head motion sensed by the headset 120. At 204, the processor 112 generates the selected laboratory simulation 300, 500, 700. In this example embodiment, the processor 112 identifies a simulation stored on the processor, and/or stored at a remote location, and configures the laboratory simulation to be projected on the attached headset 120.

At 206, the processor 112 sends instructions to the headset 120 to project the selected laboratory simulation 300, 500, 700 on the user display 122, to generate audio to be emitted from the user speakers 124, and/or rumbling, motion to be actualized at the headset 120 and/or the controller 130. In this example embodiment, the user holds, or otherwise controls the motion of the controller 130. At 208, a presence of the controller 130 in a working volume (e.g., the motion sensing grid 144) is searched for. At 210, responsive to no controller 130 being detected, the processor 112 instructs that no icon 302 be shown on the user display 122 (see FIG. 3A). At 212, responsive to the controller 130 being detected, the processor 112 instructs that the icon 302 be shown on the user display 122 (see, for example, FIG. 3B-3E). In one example embodiment, the icon 302 comprises a hand, and/or hands, which mimic the user's hands in the virtual space or virtual world. At 214, the sensor 116 of the controller is activated to detect the user's hand motion. The sensor 116 may be detected by the locators 142. The user's hand motions, including lateral, longitudinal, rotational, axial, etc. is detected by the sensor 116. The sensor 114 of the headset 120 remains active while the user is in the virtual space.

At 216, responsive to the sensors 114, 116 detecting the motion of the user, the sensors 114, 116, the locators 142, and/or both transmit the motion to the processor 112. At 218, the processor 111 instructs the headset 120 to project the icons 302 as moving in the same manner as detected by the sensors 116, and/or the locators 142 and/or alter the user's view on the user display 122 based upon the motion detected from the sensor 114. In this example embodiment, the icons 302 will move up or down, side to side, rotationally, etc. relative to the user if the controller 130 is detected as moving up and down, side to side, in and out, and/or rotationally. At 220, responsive to the sensor 116 not detecting the motion of the user, the sensors 114, 116, the locators 142, and/or all of them transmit that there is no motion to the processor 112. The processor 112 maintains instructions to project the selected laboratory simulation 300, 500, 700 on the user display 122. The selected laboratory simulation 300, 500, 700 includes the icons 302 when the controller 130 is detected, as at 212, or does not include the icons 302 when the controller is not detected, as at 210.

Microscope Simulation 300

Figure 3A:
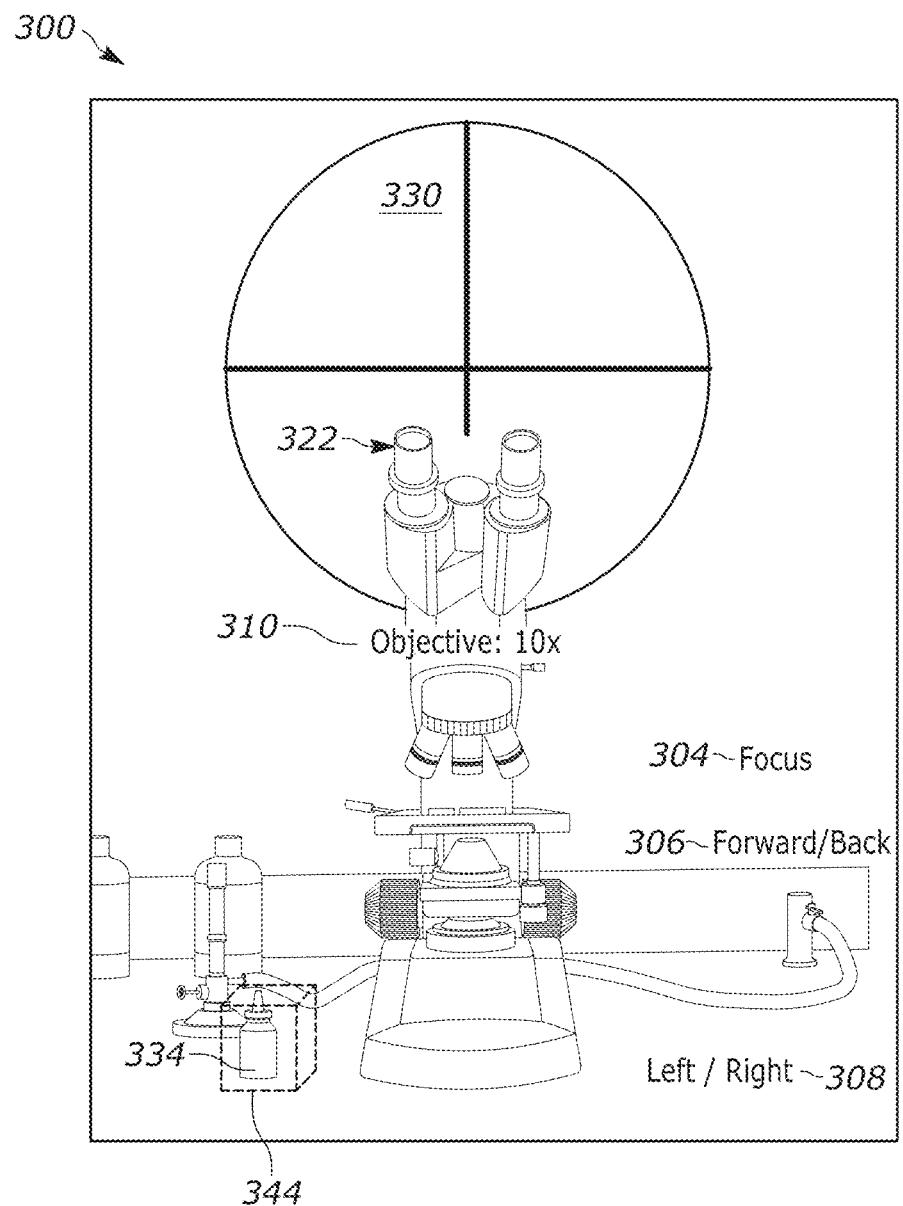
FIG. 3A illustrates a microscope simulation generated by an example virtual reality system, according to one example embodiment of the present disclosure.
Figure 3B:
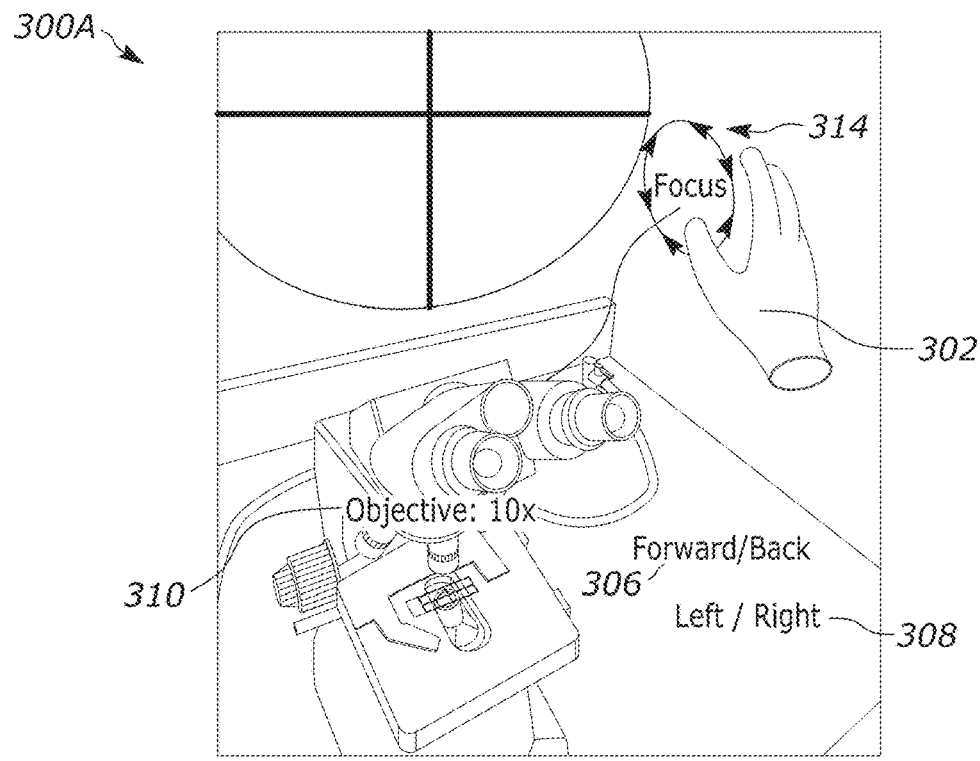
FIG. 3B illustrates a microscope simulation utilizing a focus interactive functionality generated by an example virtual reality system, according to one example embodiment of the present disclosure.
Figure 3C:
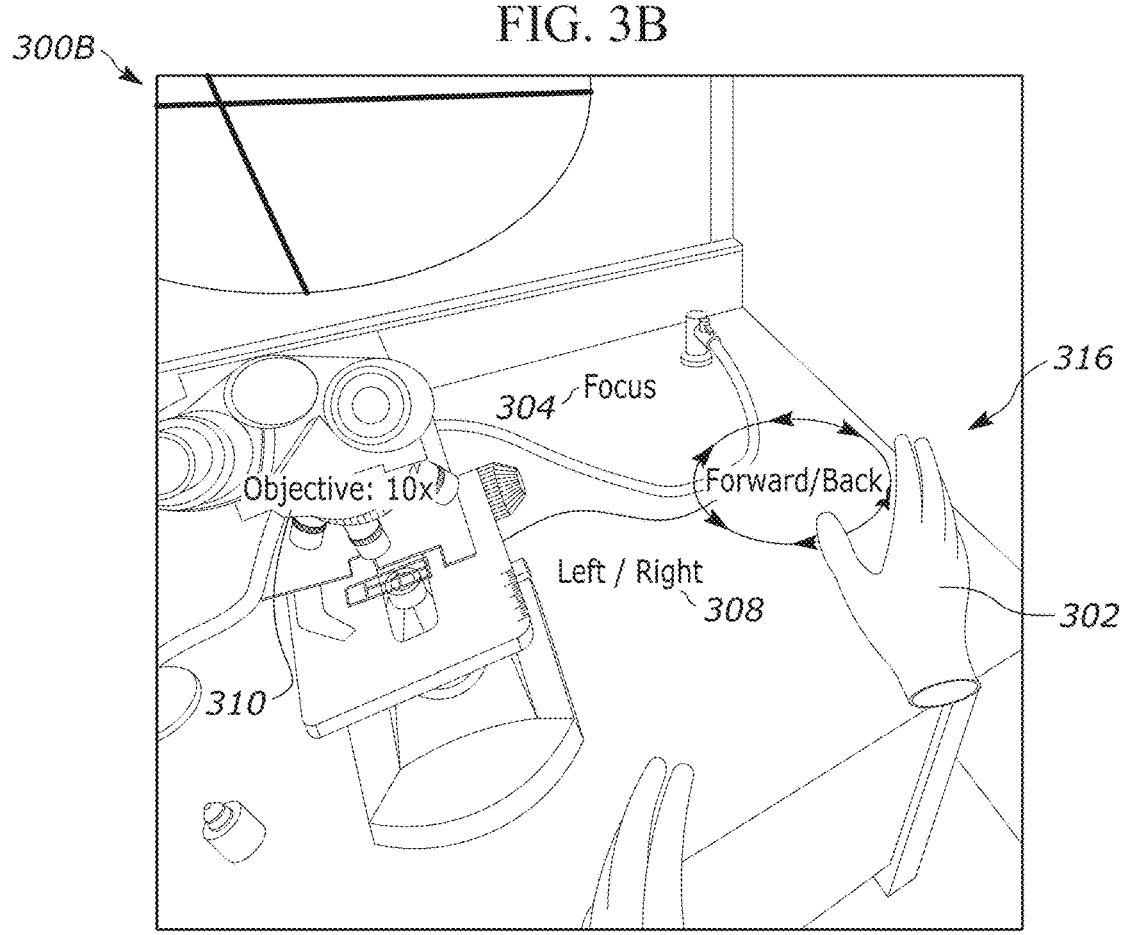
FIG. 3C illustrates a microscope simulation utilizing a lateral interactive functionality generated by an example virtual reality system, according to one example embodiment of the present disclosure.
Figure 3D:
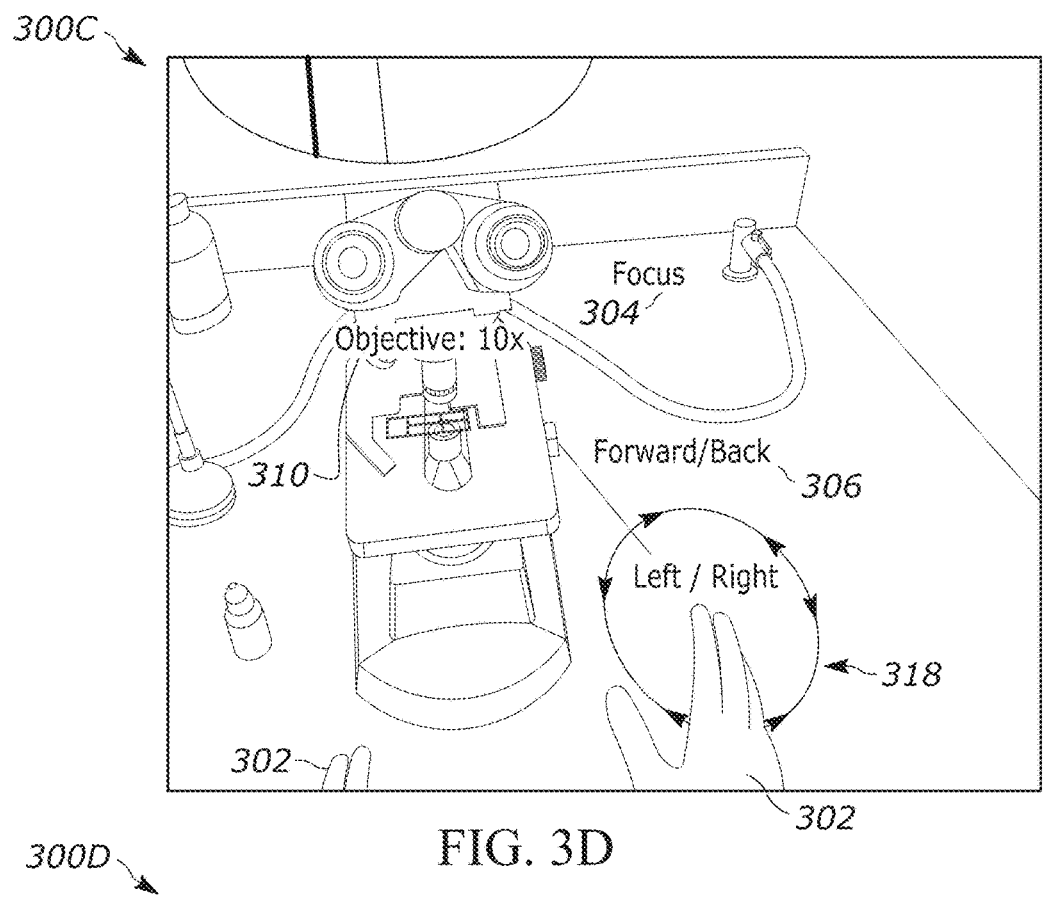
FIG. 3D illustrates a microscope simulation utilizing a longitudinal interactive functionality generated by an example virtual reality system, according to one example embodiment of the present disclosure.
Figure 3E:
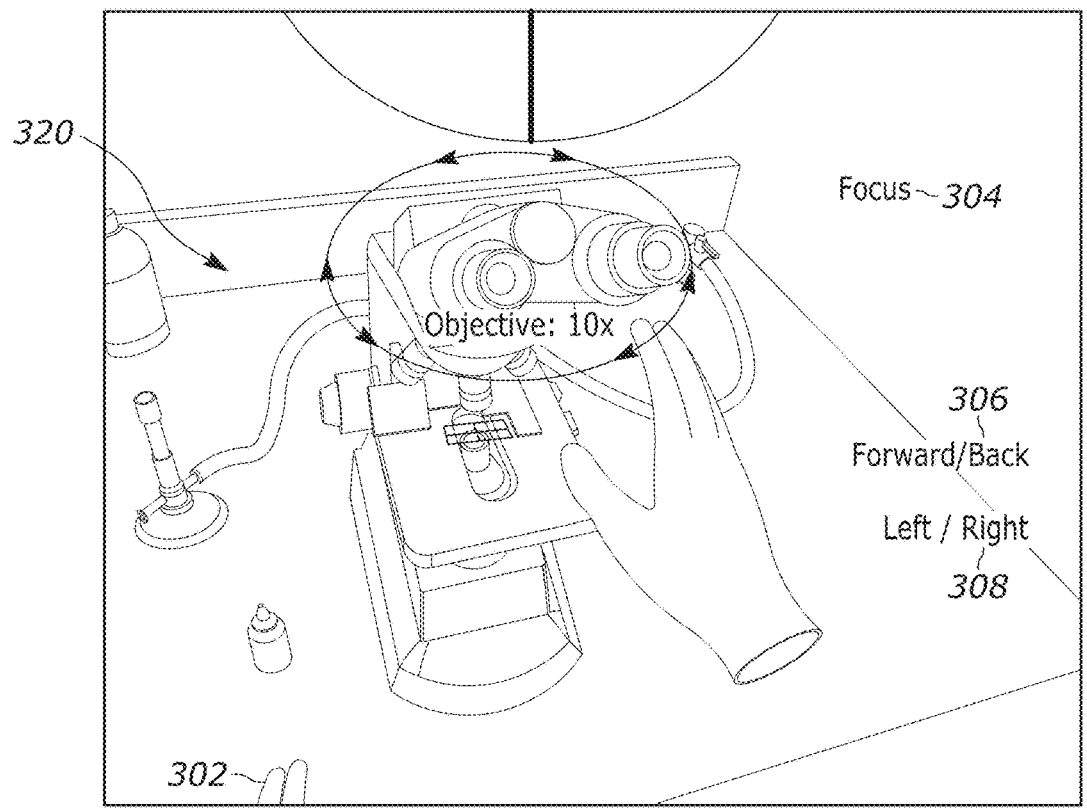
FIG. 3E illustrates a microscope simulation utilizing an objective interactive functionality generated by an example virtual reality system, according to one example embodiment of the present disclosure.
Figure 3F:
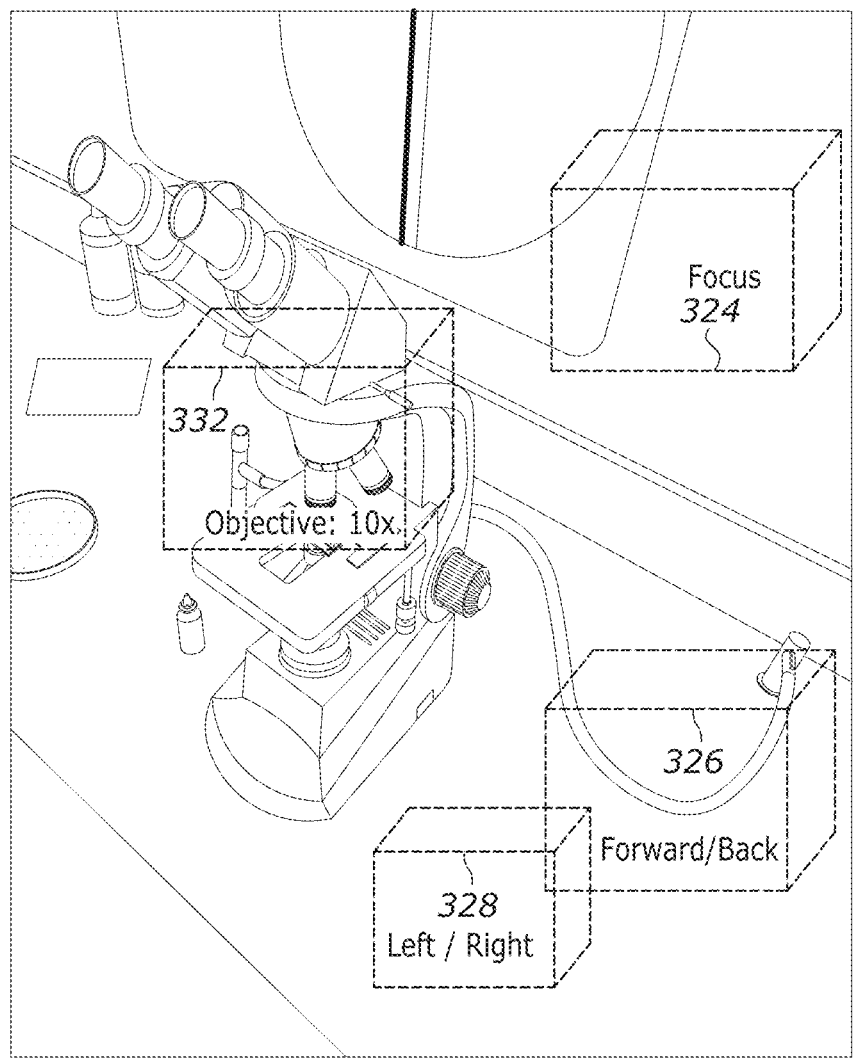
FIG. 3F illustrates a microscope simulation utilizing an activation volume interactive functionality generated by an example virtual reality system, according to one example embodiment of the present disclosure.
Figure 3G:
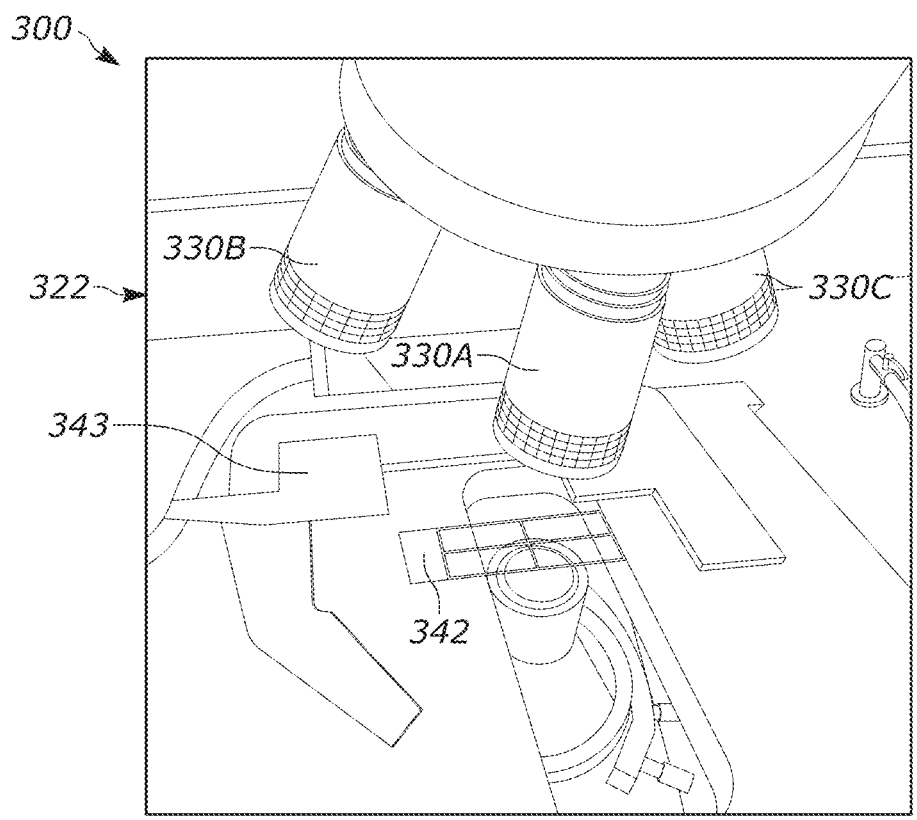
FIG. 3G illustrates a closeup view of an objective lens element of microscope simulation generated by an example virtual reality system, according to one example embodiment of the present disclosure.
Figure 3H:
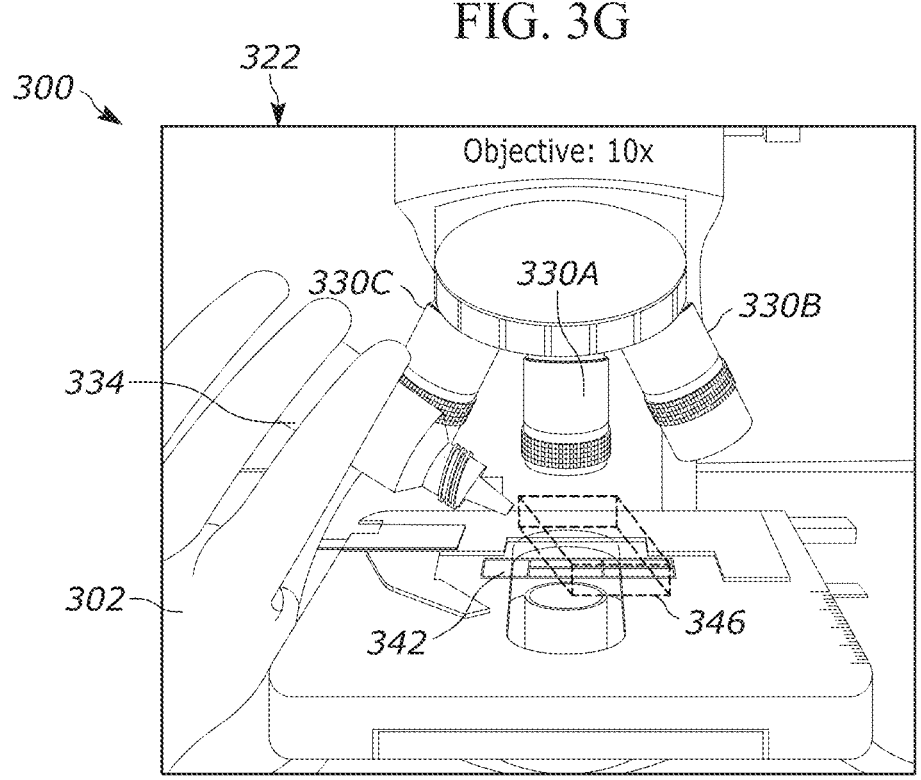
FIG. 3H illustrates a closeup view of an objective lens element of microscope simulation utilizing an oil dropper interactive functionality generated by an example virtual reality system, according to one example embodiment of the present disclosure.
Figure 4A:
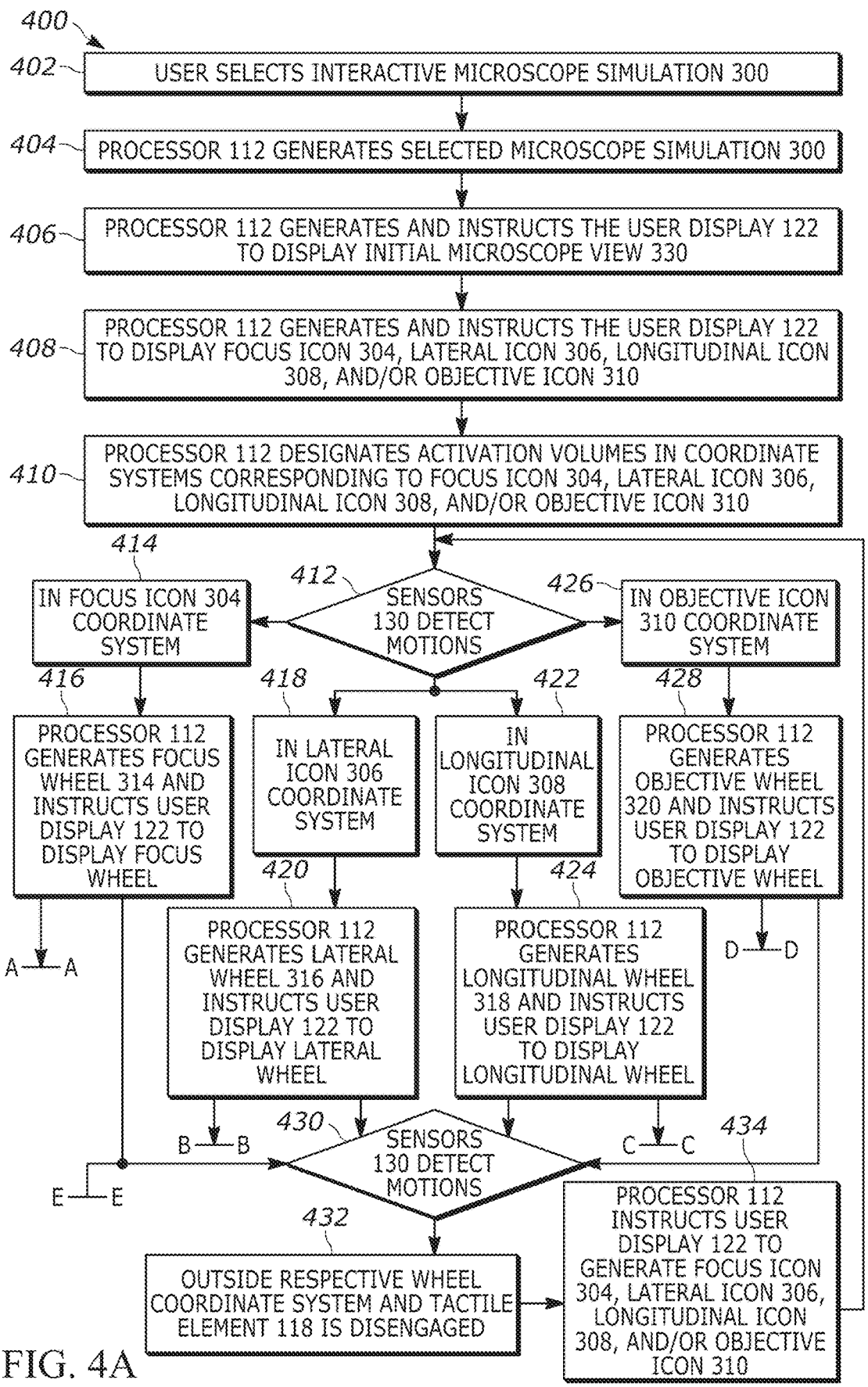
FIG. 4A is a schematic diagram of a method of using a selected microscope simulation generated by an example virtual reality system, according to one example embodiment of the present disclosure.

As illustrated in FIG. 4A, a method 400 of use of the virtual reality system 100 with the interactive microscope simulation 300 is illustrated. At 402, the processor 112 receives a signal indicating the user has selected the interactive microscope simulation 300 (see FIG. 3A). At 404, the processor 112 generates the microscope simulation 300, including generating an image of a microscope 322 and instructs the user display 122 to display the microscope simulation. At 406, the processor 112 generates and instructs the user display to display an initial microscope view 330 by calculating Equations 1-11, discussed below. A microscope view comprises a heads-up display that illustrates what a user would view when looking into a lens of a microscope in the real world. The initial microscope view comprises the view prior to user input, and subsequent altered microscope views comprise the view including the user input. In another embodiment, the sensor 116 sends a signal to the processor 112 that the controller 130 is within a wheel volume. The wheel volume comprises a Cartesian coordinate system defining a microscope activation distance (e.g. between 6 inches to 12 inches) of the virtual reality microscope 322. The microscope activation distance defines a three-dimensional volume that extends along x, y, and z axes. At 408, the processer 112 generates and instructs the user display 122 to display a focus icon 304, a lateral icon 306, a longitudinal icon 308, an objective icon 310, and/or an oil dropper 334 (see, for example, FIG. 3A). Steps 404-410 may be performed in any order, and/or may be performed simultaneously. In another example embodiment, the processer 112 instructs the user display 122 to display the focus icon 304, the lateral icon 306, the longitudinal icon 308, the objective icon 310, and/of the oil dropper 334 responsive to the controller 130 being detected within the microscope activation distance. At 410, the processor 112 designates wheel activation volumes 324, 26, 328, 330 and an oil activation volume 344 (see FIGS. 3F, 3A) in Cartesian coordinate systems corresponding to the focus icon 304, the lateral icon 306, the longitudinal icon 308, the objective icon 310 and/or the oil dropper 334. In this example embodiment, the wheel activation volumes 324, 326, 328, 330 comprise three dimensional spatial coordinate volumes radiating out along x, y, and z axes (hereinafter "volume" unless otherwise defined) from a central location (coordinates 0,0,0) wherein the respective icon is located, or a center point of the respective icon. In this embodiment, the wheel activation volumes 324, 326, 328, 330 extend between 1 inch to about 7 inches along the x axis, between 1 inch to about 7 inches along the y axis, and/or between 1 inch to about 7 inches along the z axis, wherein the volume defined within comprises the respective wheel activation volumes. Inches in vertical space are based upon perceived distance by the user. At 412 the sensor 116 detects motion.

Focus Wheel 314

At 414, the sensor 116 detects motion in a focus wheel volume 324 defined by the focus icon 304 (FIGS. 3A, 3F). At 416, responsive to the sensor 116 detecting motion in the focus wheel volume 324, the processor generates a focus wheel 314 and instructs the user display 122 to display the focus wheel 314 (see FIG. 3B). In this example embodiment, the processor 112 instructs the user display 122 to continue to display the icons 304, 406, 308, 310, and/or the oil dropper 334 when displaying the focus wheel 314. In another example embodiment, the processor 112 instructs the user display 122 to remove the icons 304, 406, 308, 310, aid/or the oil dropper 334 when displaying the focus wheel 314.

Figure 4B:
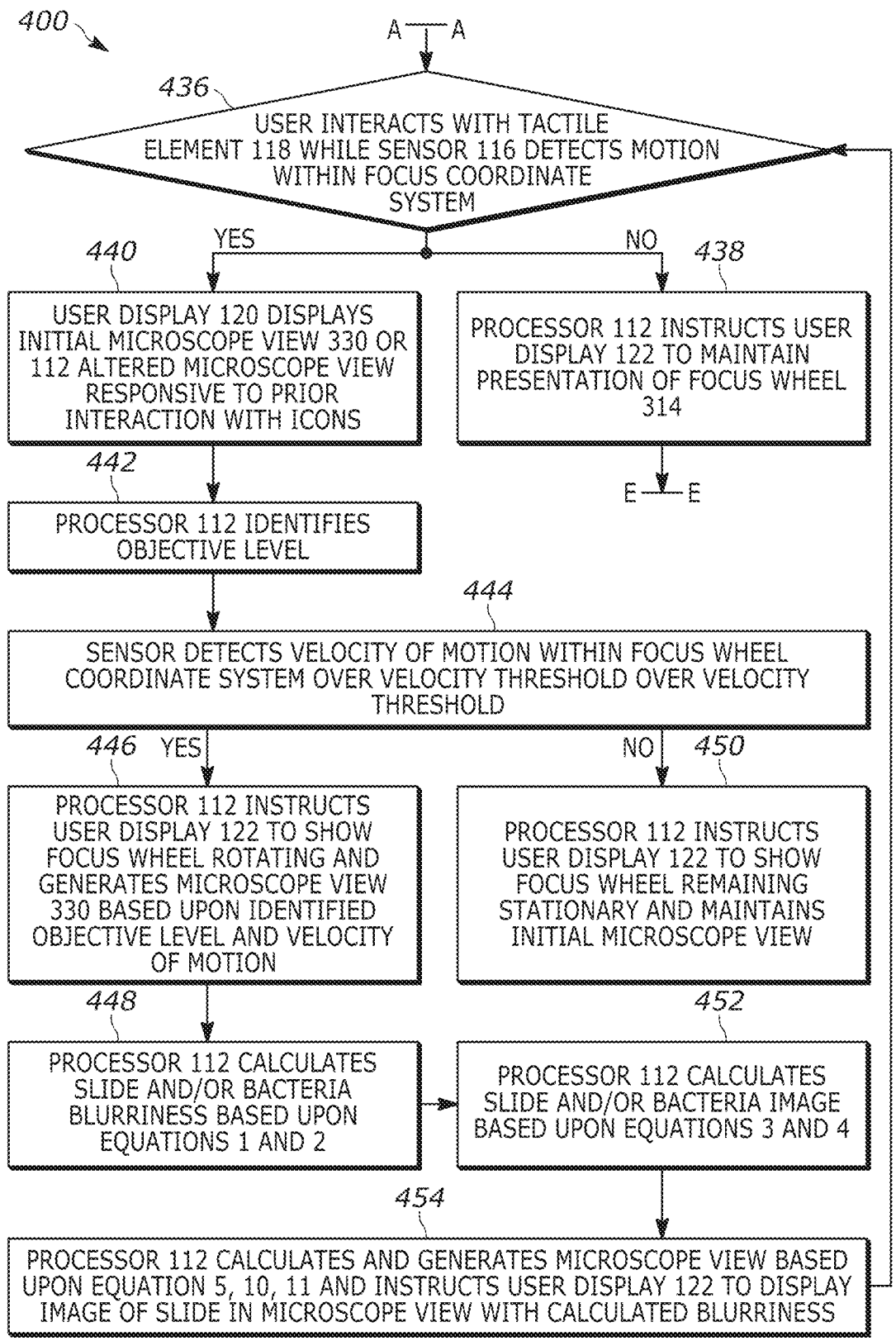
FIG. 4B is a schematic diagram of a method of using A focus function in a selected microscope simulation generated by an example virtual reality system, according to one example embodiment of the present disclosure.

As continued in example method 400 in FIG. 4B, continued from section line A-A, at 436, the virtual reality system 100 determines if the user is interacting with the tactile element 118 while the sensor 116 detects motion within the focus wheel coordinate system. At 438, responsive to the user not interacting with the tactile element 118 and/or the sensor 116 not detecting motion within the focus wheel coordinate system, the processor instructs the user display 122 to maintain presentation of the focus wheel 314. At 430, 432, as illustrated in FIG. 4A, at section line E-E, responsive to the sensor 130 detecting motion outside the respective wheel coordinate system coordinate system and/or the user disengaging the tactile element 118, the processor 112 instructs the user display 122 to revert to displaying the focus icon 304, the lateral icon 306, the longitudinal icon 308, the objective icon, 310 and/or the oil dropper 334, and removes the presentation of the focus wheel 314.

At 440, the processor generates and instructs the user display 122 to continue to display the initial microscope view 330 and/or an altered microscope view based upon user interaction with other icons (see FIG. 3A, and FIGS. 3K-3N). At 442, the processor 112 identifies an objective level, wherein absent the user having altered the objective level, discussed below, remains at a default objective level (e.g. 10× magnification). At 444, the sensor 116 detects a velocity of a motion within the focus wheel 314 coordinate system. At 450, responsive to the velocity of a motion within the focus wheel 314 coordinate system being below a velocity threshold (e.g., 0), the processor 112 instructs the user display 122 to show the focus wheel 314 remaining stationary and instructs the user display 122 to continue to show the microscope view 30 displayed at step 440. At 446, responsive to the velocity of a motion within the focus wheel 314 coordinate system being above a velocity threshold (e.g., above 0), the processor 112 instructs the user display 122 to show the focus wheel 314 rotating and generates and instructs the user display 122 to show a microscope view 330 based upon the identified objective level and the velocity/degree of rotation of the motion. If the focus wheel 314 has already rotated 180 degrees either clockwise or counterclockwise from its initial position, the processor 112 instructs the user display 122 to stop showing the focus wheel moving. In this example embodiment, the initial position is equal to 0.5. A rotation clockwise of 180 degrees is equal to 1, and rotation counter clockwise of 180 degrees is equal to 0.0. At 448, the processor 112 calculates a slide blurriness and a bacteria blurriness utilizing Equations 1 and 2 below. The slide blurriness and the bacteria blurriness are calculated utilizing d variable: no_oil multiplier, and the degree of the rotation of the focus wheel 314, based upon the following Equations:

$$\text{slide\_blurriness} = (1-(1-\text{abs}(\text{focus\_wheel}-\text{SLIDE\_FOCUS LEVEL}))*\text{no\_oil\_multiplier})*\text{objective\_level} \quad \text{Equation 1:}$$

$$\text{bacteria\_blurriness} = (1-(1-\text{abs}(\text{focus\_wheel}-\text{BACTERIA\_FOCUS\_LEVEL}))*\text{no\_oil\_multiplier})*\text{objective level} \quad \text{Equation 2}$$

Wherein, the focus_wheel is the degree of rotations of the focus wheel 314 that the sensor 116 transmits to the processor 112, varying between 0.0 and 1.0 corresponding to 0 to 360 degrees of rotation, SLIDE_FOCUS_LEVEL is a constant (see Table 1, below), no_oil_multiplier is a value of 1 or 0.9, wherein 1 indicates the user has applied oil or the objective is not set to 100×, and 0.9 indicates the user has not applied oil to the slide and the objective is at 100×, and the objective_level is the default or input objective level (e.g. 10×, 25×, 50×, 100× magnification) wherein values for the variable levels are listed in Table 1, below. The objective value is stored in memory, and the processor 112 accesses the memory based upon any alterations made within a session. The processor 112 applies the stored objective level to Equations 1 and 2. Abs is the absolute value. Slide blurriness and bacteria_blurriness are floating point numbers with a minimum value of 0.0, which results in a clear image in later calculations of the Microscope View 330. As the blurriness variables increase, the resulting images become blurrier.

TABLE 1

| Constant Name | Assigned Value |
|---|---|
| SLIDE_FOCUS_LEVEL | .7 |
| BACTER1A_FOCUS_LEVEL | .85 |
| OBJECTIVE_LEVEL_10X | .1 |
| OBJECTIVE_LEVEL_40X | .4 |
| OBJECTIVE_LEVEL_75X | .8 |
| OBJECTIVE_LEVEL_100X | 1.2 |

Several source images are utilized by processor 112 to generate the final microscope view 330. These are listed in Table 2.

TABLE 2

| Image Name | FIG. |
|---|---|
| Bacteria_image_source | 3O |
| Slide_image_source | 3P |
| vignette_mask | 3Q |
| targeting_crosshair_image | 3R |
| Kernel_image | 3S |

Further, variables are defined in Table 3, below:

TABLE 3

| Variable | type |
|---|---|
| no_oil_multiplier | float |
| focus_wheel | float |
| lateral_wheel | float |
| longitudinal_wheel | float |
| objective_wheel | 10X, 40X, 75X, 100X (set of names) |
| slide_blurriness | float |
| bacteria_blurriness | float |
| slide_image_t | image |
| slide_image_z | image |
| slide_image_b | image |
| bacteria_image_t | image |
| bacteria_image_z | image |
| bacteria_image_b | image |
| microscope_view_full | image |
| stage_x | float |
| stage_y | float |
| objective_magnification | Float = {10.0, 40.0, 75.0, 100.0} depending on objective |
| objective_level | Float = {.1, .4, .8, 1.2} depending on objective |

At 452, the processor 112 calculates a slide image and a bacteria image utilizing Equations 3 and 4, below. Note, position information (e.g., input using the lateral or longitudinal wheels 316, 318, discussed below) that the processor 112 has received previously in a single session will be applied first to determine what portion of the slide 342 to display in the microscope view 330. The slide image and bacteria image are calculated using the following Equations:

$$\text{slide\_image}\_b = \text{disc\_blur}(\text{slide\_image}\_z, \text{kernel\_image}, \text{slide\_blurriness}) \quad \text{Equation 3}$$

$$\text{bacteria\_image}\_b = \text{disc\_blur}(\text{bacteria\_image}\_z, \text{kernel\_image}, \text{bacteria\_blurriness}) \quad \text{Equation 4}$$

Wherein, the disc_blur is a standard image processing filter operation involving the convolution of a circular kernel and an image, slide_image_z is derived from Equation 6 and then 8, discussed below, and bacteria_image_z is derived from Equation 7 and then 9, discussed below. At 454, the processor 112 calculates and generates an altered microscope view based upon Equations 5, 10 and 11 below, by first multiplying three (3) images together, and then applying a vignette by setting the alpha channel (transparency) to vignette_mask to then generate the microscope view 330 utilizing the Equations below:

$$\text{Microscope View\_full} = \text{slide\_image}\_b * \text{bacteria\_image}\_b * \text{targeting\_crosshair\_image} \quad \text{Equation 5}$$

$$\text{Microscope\_view\_full.alpha} = \text{vignette\_mask} \quad \text{Equation 10}$$

$$\text{Microscope View 330} = \text{Microscope\_view\_full} \quad \text{Equation 11}$$

Figure 3I:
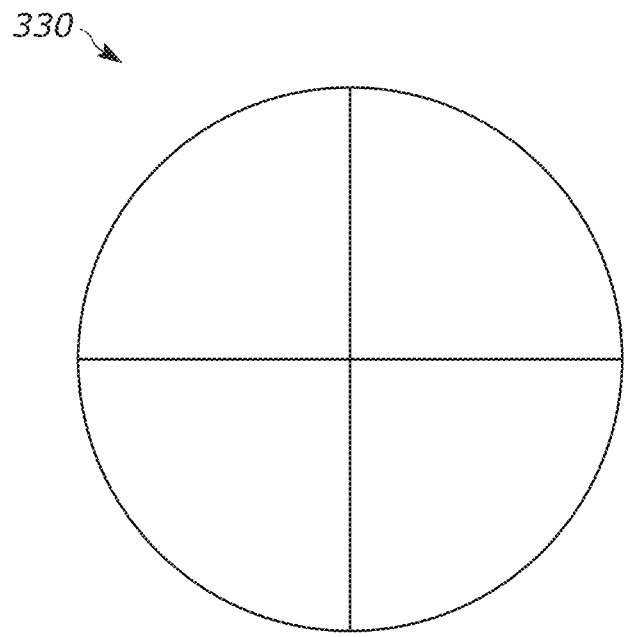
FIG. 3I illustrates a microscope view corresponding to a slide present on a microscope of a microscope simulation generated by an example virtual reality system, according to one example embodiment of the present disclosure.
Figure 3J:
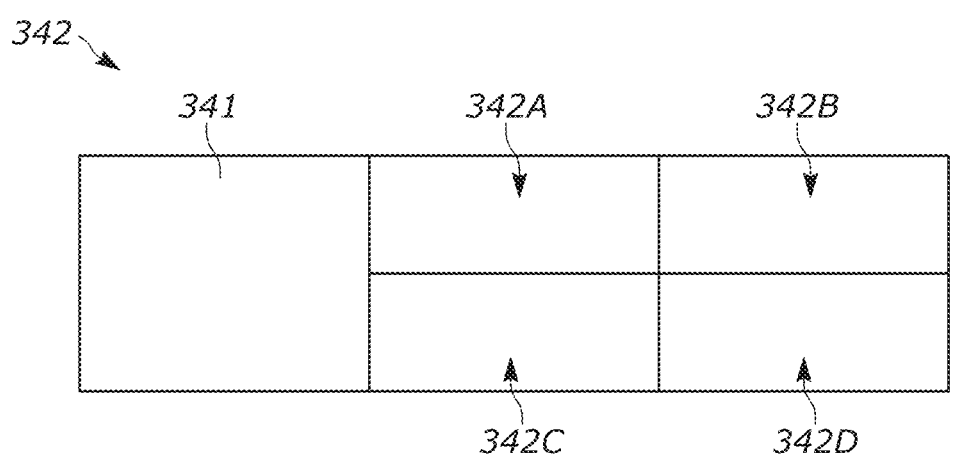
FIG. 3J illustrates a slide present on a microscope of a microscope simulation generated by an example virtual reality system, according to one example embodiment of the present disclosure.
Figure 3L:
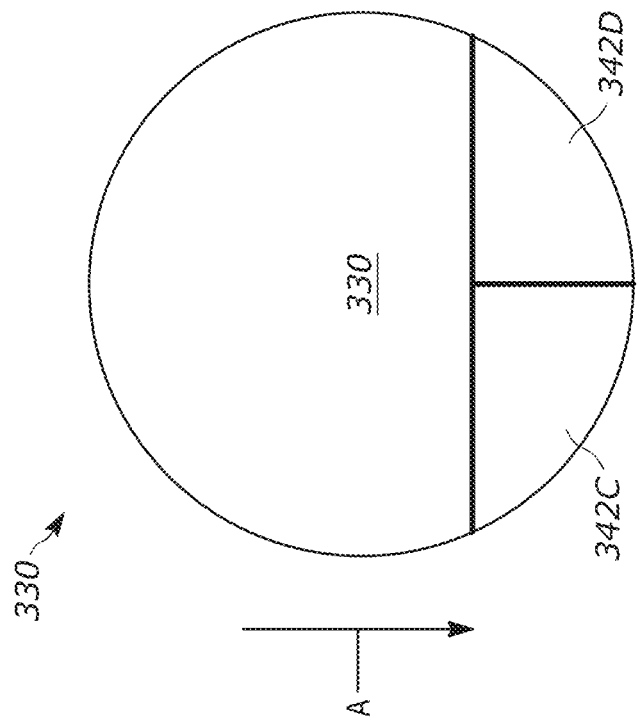
FIG. 3L illustrates a microscope view corresponding to a view of a slide, wherein the view of the slide has been altered through use of the lateral wheel present on a microscope of a microscope simulation generated by an example virtual reality system, according to one example embodiment of the present disclosure.
Figure 3K:
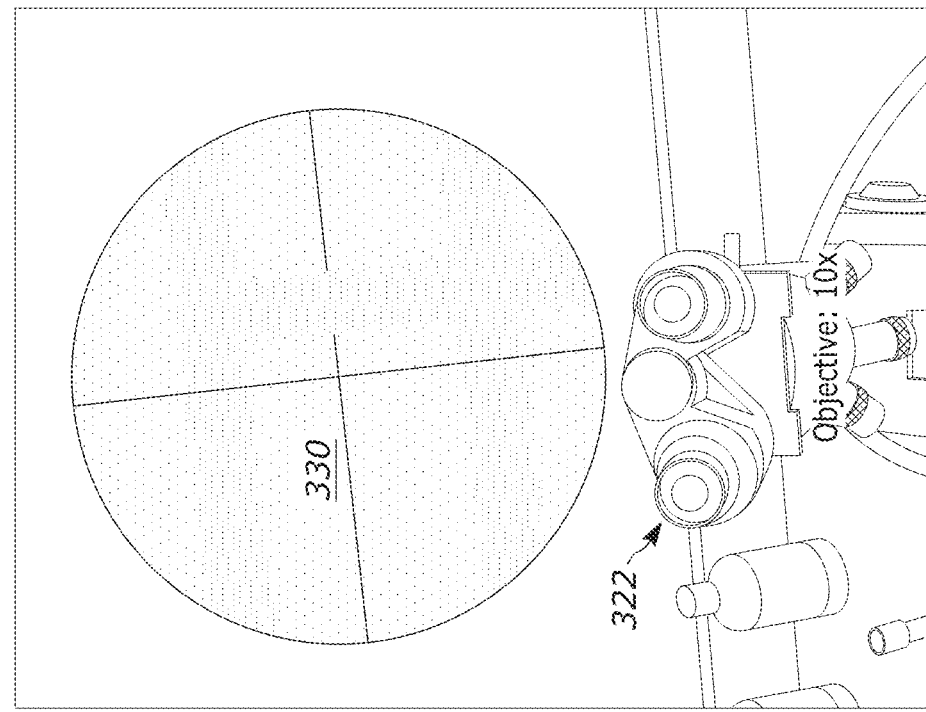
FIG. 3K illustrates a microscope view corresponding to a view of a slide, wherein the view of the slide has been altered through use of the focus wheel present on a microscope of a microscope simulation generated by an example virtual reality system, according to one example embodiment of the present disclosure.
Figure 3N:
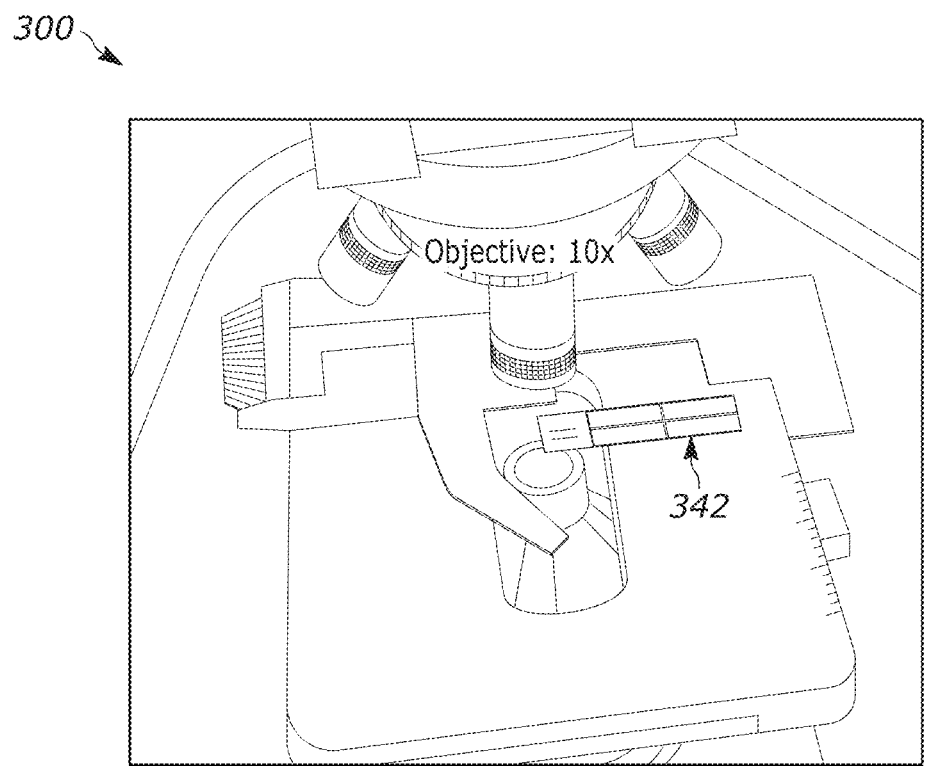
FIG. 3N illustrates a microscope view corresponding to a view of a slide wherein the view of the slide has been-altered through use of the objective wheel present on a microscope of a microscope simulation generated by an example virtual reality system, according to one example embodiment of the present disclosure.
Figure 3N:
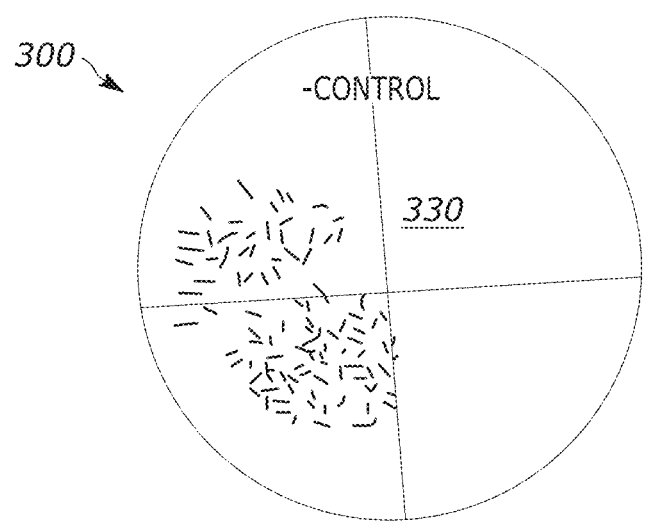
Figure 3O:
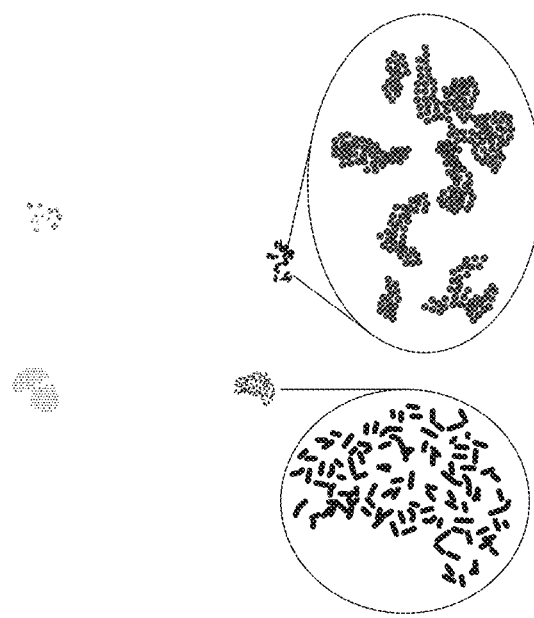
FIG. 3O illustrates a bacteria image source constant, according to one example embodiment of the present disclosure.
Figure 3P:
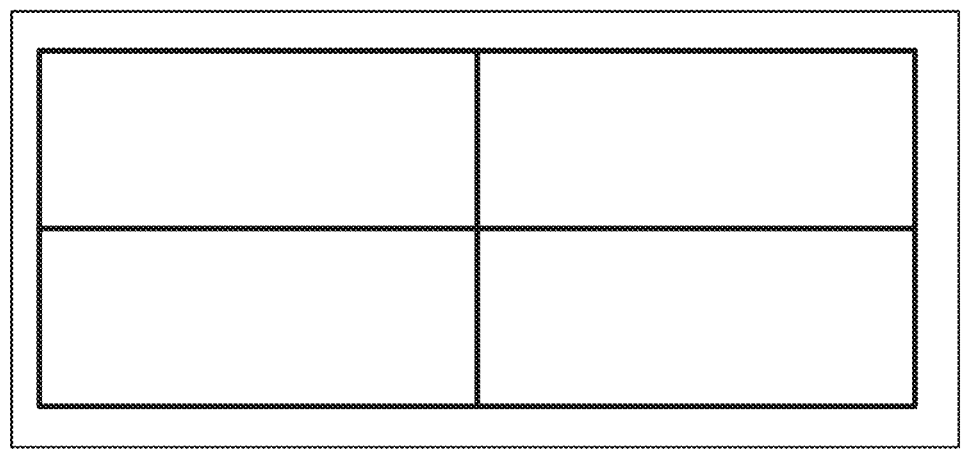
FIG. 3P illustrates a slide image source constant, according to one example embodiment of the present disclosure.
Figure 3Q:
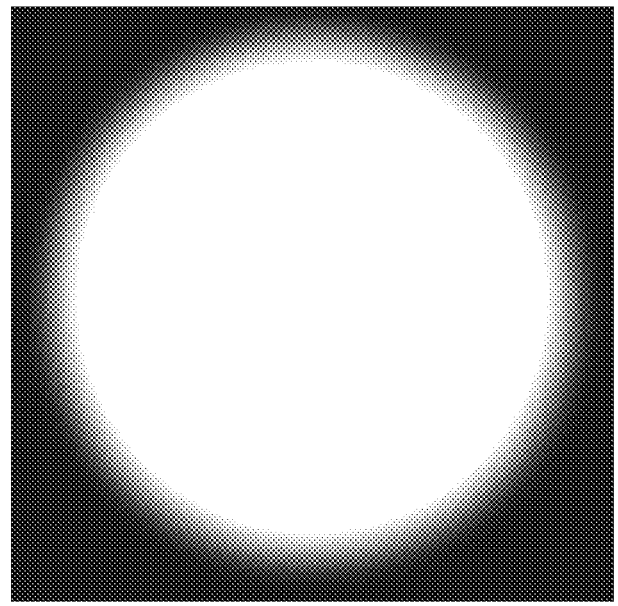
FIG. 3Q illustrates a vignette mask source constant, according to one example embodiment of the present disclosure.
Figure 3R:
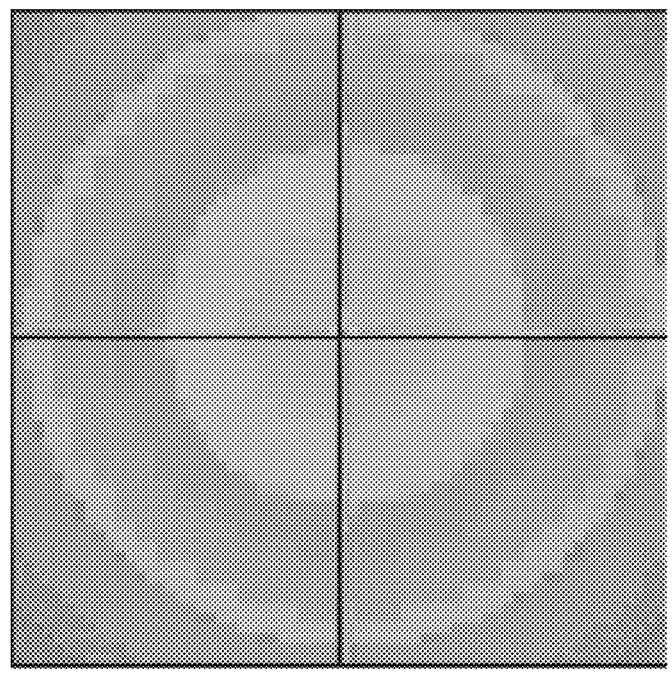
FIG. 3R illustrates a targeting crosshair image constant, according to one example embodiment of the present disclosure.
Figure 3S:
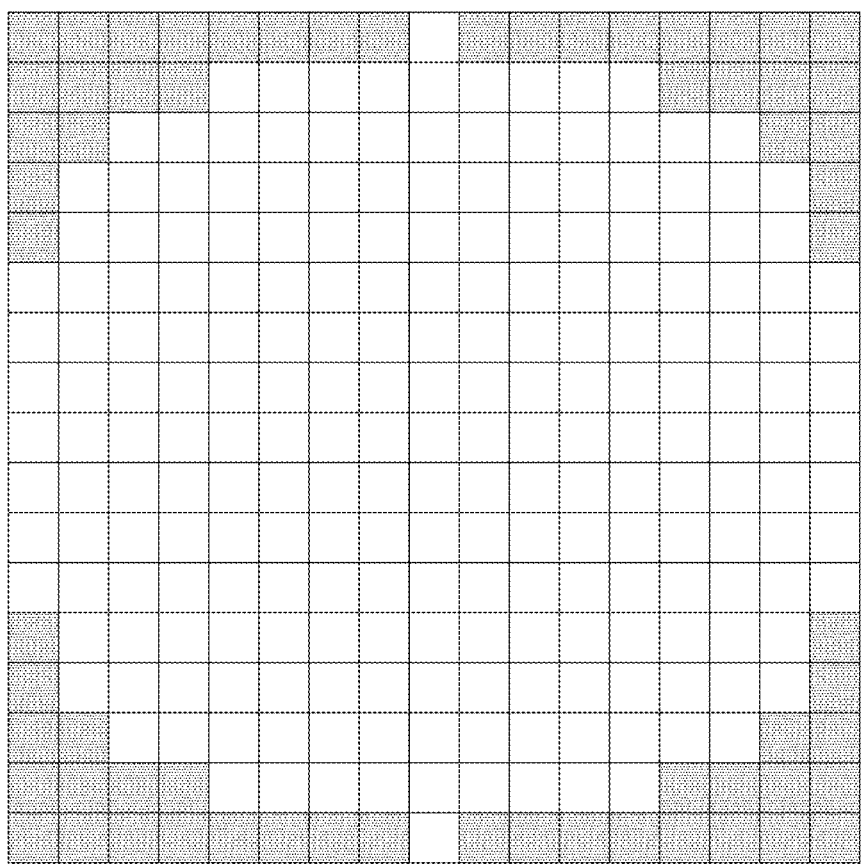
FIG. 3S illustrates a kernel image constant, according to one example embodiment of the present disclosure.

The targeting_crosshair_image is illustrated in FIG. 3R and the vignette_image is illustrated in FIG. 3Q. (see Table 2 above). The processor 112 instructs the user display 122 to display the initial microscope view 330 (see FIG. 3L1) or an adjusted microscope view (see FIGS. 3L2-3L5, 3M1-3M4). The processor 112 instructs the user display 122 to display a slide image in the microscope view 330 with the calculated blurriness. Blurriness is a variable used as part of an input to a disc blur. The disc blur is a standard graphics-processing technique. In the illustrated example embodiment of FIG. 3K, the focus wheel 314 has been utilized by the user to generate an altered microscope view 330 that is blurry. Returning to FIG. 4B of method 400, the method returns to step 436, wherein the user may proceed with additional adjustments of the focus wheel 314 (steps 440-454), or may proceed to another wheel 316, 318, 320 by proceeding with steps 338, 430, 432, and 434, or utilize the oil dropper 334.

Lateral Wheel 316

At 418 of the method 400 illustrated in FIG. 4A, the sensor 116 detects motion in a lateral wheel volume 326 defined by the lateral icon 306 (FIGS. 3A, 3F). In one example embodiment, the sensor 116 detects motion in focus wheel volume 324 prior to the lateral wheel volume 326, and the processor stores and instructs the user display 122 to present an altered microscope view based upon method 400 steps 440-445 (e.g., presents the focus generated by the user interaction with the focus wheel 314). In another example embodiment, such as when the processor 112 has not received inputs based upon method 400 steps 440-445, the processor 112 instructs the user display 122 to display the initial microscope view 330 (see FIG. 3L1). At 420, responsive to the sensor 116 detecting motion in the lateral wheel volume 326, the processor generates a lateral wheel 316 and instructs the user display 122 to display the lateral wheel 316 (see FIG. 3C). In this example embodiment, the processor 112 instructs the user display 122 to continue to display the icons 304, 406, 308, 310, and/or the oil dropper 334 when displaying the lateral wheel 316. In another example embodiment, the processor 112 instructs the user display 122 to remove the icons 304, 406, 308, 310, and/or the oil dropper 334 when displaying the lateral wheel 316.

Figure 4C:
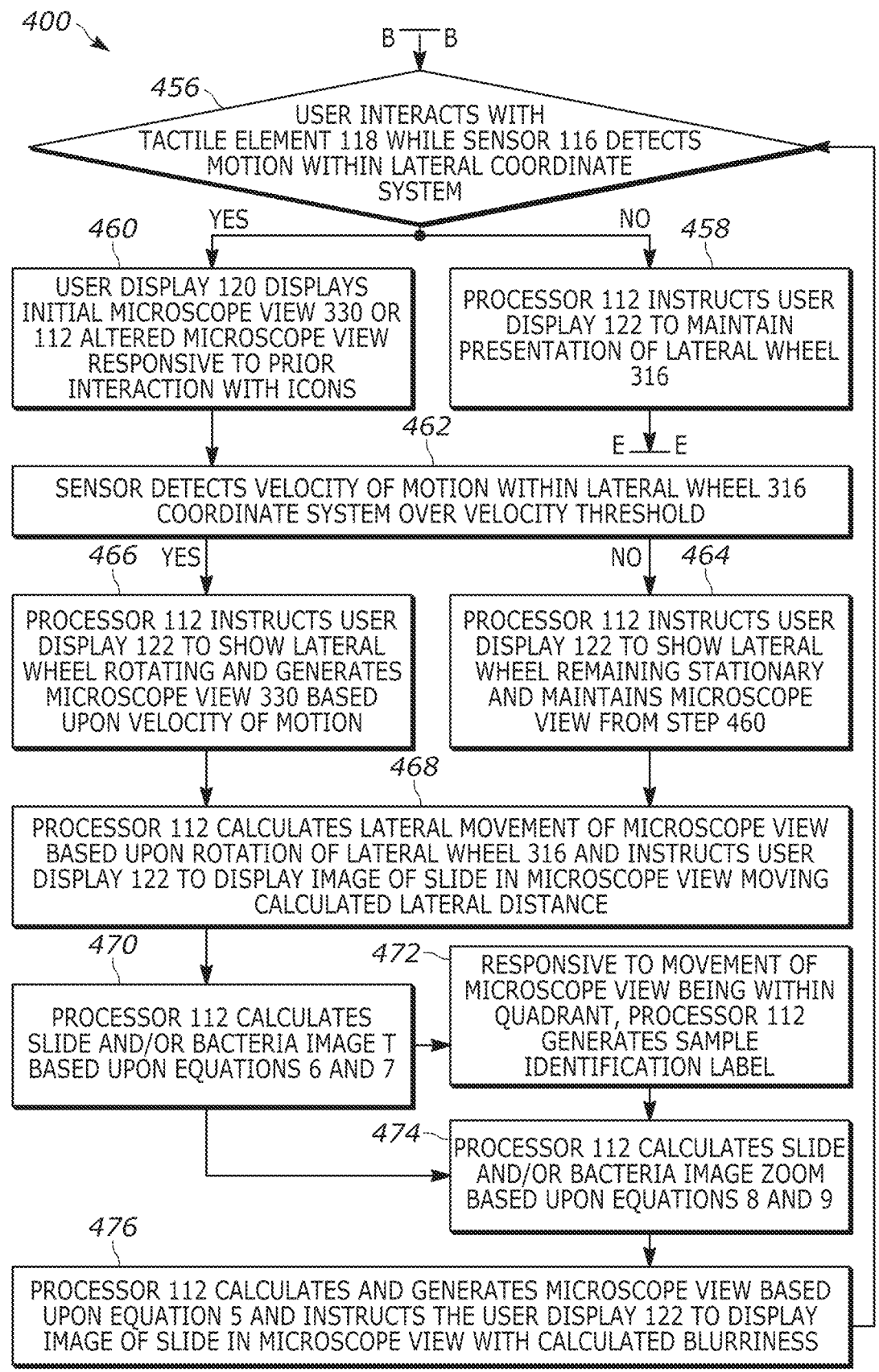
FIG. 4C is a schematic diagram of a method of using a lateral function in a selected microscope simulation generated by an example virtual reality system, according to one example embodiment of the present disclosure.

As continued in example method 400 in FIG. 4C, continued from section line B-B, at 456, the virtual reality system 100 determines if the user is interacting with the tactile element 118 while the sensor 116 detects motion within the lateral coordinate system. At 458, responsive to the user not interacting with the tactile element 118 and the sensor 116 not detecting motion within the lateral wheel coordinate system, the processor 112 instructs the user display 122 to maintain presentation of the lateral wheel 316. At 430, 432, as illustrated in FIG. 4A, at section line E-E, responsive to the sensor 116 detecting motion outside the respective wheel coordinate system coordinate system and the user disengaging the tactile element 118, the processor 112 instructs the user display 122 to revert to displaying the focus icon 304, the lateral icon 306, the longitudinal icon 308, the objective icon 310 and/or the oil dropper 334.

At 460, the processor generates and instructs the user display 122 to continue to display the initial microscope view 330 and/or an altered microscope view based upon user interaction with other icons (see FIG. 3A, and FIGS. 3K-3N).

At 462, the sensor 116 detects a velocity of a motion within the lateral wheel coordinate system. At 466, responsive to the velocity/degree of rotation of a motion within the lateral wheel 316 coordinate system coordinate system being above a velocity threshold, the processor 112 instructs the user display 122 to show the lateral wheel 316 rotating and generates and instructs the user display 122 to show a microscope view 330 based upon the velocity/degree of rotation of the motion. The processor 112 also instructs the user display 122 to show a microscope stage 343 and slide 342 moving towards or away from the user (see FIGS. 3G, 3L2-3L5). At 464, responsive to the velocity of a motion within the lateral wheel 316 coordinate system being below a velocity threshold, the processor 112 instructs the user display 122 to show the lateral wheel 316 remaining stationary and instructs the user display 122 to continue to show the microscope view 330 displayed at step 460. At 468, the processor 112 calculates a lateral movement of the microscope view based upon the rotation of the lateral wheel 314 and instructs the user display 122 to display images of the slide 342 in the microscope view 330 moving a calculated lateral distance through the following equations. At 470, the processor 112 calculates a lateral movement of the microscope view utilizing Equations 6 and 7 below. The images slide_image_t and a bacteria_image_t are calculated are calculated using the following Equations:

$$\text{slide\_image\_}t=\text{translate}(\text{slide\_image\_source},\text{stage\_}x, \text{stage\_}y) \quad \text{Equation 6:}$$

$$\text{bacteria\_image\_}t=\text{translate}(\text{bacteria\_image\_source}, \text{stage\_}x,\text{stage\_}y) \quad \text{Equation 7:}$$

slide_image_t and bacteria_image_t are calculated utilizing a function translate which shifts and crops the source image. Stage_y is a variable that depends on the velocity/degree of rotation of the motion of the lateral wheel 316, wherein if stage_y is greater than 1, stage_y equals 1, and if stage_y is less than 0, stage_y equals 0. In an example embodiment, stagey starts at 0.5, and one rotation clockwise corresponds to stage_y=1.0, and one rotation counter-clockwise corresponds to stage_y=0.0. Stage_x remains constant, and is dependent upon movement of the longitudinal wheel 318.

At 472, responsive to the movement of the microscope view 330 being within a single quadrant 342a, 342b, 342c, 342d of the slide 342 (see FIGS. 3I, and 3N), the processor 112 generates and instructs the user display 122 to display a sample identification label (e.g., identifying the gram stain and/or shape, cocci or rod, of the bacteria present in the quadrant or the quadrant identification, e.g., Control +, Sample 1). In the illustrated example embodiment of FIG. 3N, the microscope view 330 is within a single quadrant. Responsive to the movement of the microscope view 330 being outside a single quadrant 342a, 342b, 342c, 342d of the slide 342, the processor 112 does not generate or instruct the user display 122 to display the sample identification label.

At 474, the processor 112 calculates a zoom or a magnification of the image seen through microscope view utilizing Equations 8 and 9 below. Slide_image_z and bacteria_image_z are calculated using the following Equations:

$$\text{slide\_image\_}z=\text{zoom}(\text{slide\_image\_}t,\text{stage\_}x,\text{stage\_}y, \text{objective\_magnification}) \quad \text{Equation 8:}$$

$$\text{bacteria\_image\_}z=\text{zoom}(\text{bacteria\_image\_}t,\text{stage\_}x, \text{stage\_}y,\text{objective\_magnification}) \quad \text{Equation 9:}$$

The slide_image_z and the bacteria_image_z are calculated utilizing a function zoom, which scales the image based on the current objective level about the current stage_y and stage_x locations Stage_y is the same variable as described above with regard to Equations 6 and 7. Stage_x remains constant, and is dependent upon movement of the longitudinal wheel 318. The objective_magnification corresponds to the current-objective set on the microscope, and is 10.0 for 10×, 40.0 for 40×, 75.0 for 75×, and 100.0 for 100×.

At 476, the processor 112 calculates the slide_image_b and bacteria_image_b busing Equations 3 and 4 above, then calculates the microscope view 330 utilizing Equations 5, 10, and 11 above, and instructs the user display 122 to display the microscope view 330 that corresponds to the lateral movement instigated by the motion of the user and the lateral wheel 316. In the illustrated example embodiment of FIG. 3L, the lateral wheel 316 has been utilized by the user to generate an altered microscope view 330 wherein the slide 342 has been moved along direction A, such that only top portions of quadrants 342c, 142d are visible. In the illustrated example embodiment of FIGS. 3L2-3L3, the lateral wheel 316 has been utilized by the user to generate an altered microscope view 330 wherein the slide 342 has been moved along direction A a maximum distance. In the illustrated example embodiment of FIG. 3L4-3L5, the lateral wheel 316 has been utilized by the user to generate an altered microscope view 330 wherein the slide 342 has been moved along direction C a maximum distance. The method 400 returns to 456, wherein the user may proceed with adjusting the lateral wheel 316 again (steps 460-476), or may proceed to another wheel 314, 318, 320, or the oil dropper 334 by proceeding with steps 458, 430, 432, and 434.

Longitudinal Wheel 318

At 422 of the method 400 illustrated in FIG. 4A, the sensor 116 detects motion in a longitudinal wheel volume 328 defined by the longitudinal icon 308 (FIGS. 3A, 3F). In one example embodiment, the sensor 116 detects motion in the focus wheel volume 324 and/or the lateral wheel volume 326 prior to the longitudinal wheel volume 328, and the processor stores and instructs the user display 122 to present an altered microscope view based upon method 400 steps 440-445 and/or 460-476 (e.g., any focus or lateral inputs by the user are reflected in the microscope view). In another example embodiment, such as when the processor 112 has not received inputs based upon method 400 steps 440-445 and 460-476, the processor 112 instructs the user display 122 to display the initial microscope view 330.

At 422, the sensor 116 detects motion in a longitudinal wheel volume 328 defined by the longitudinal icon 308 (FIGS. 3A, 3D). At 424, responsive to the sensor 116 detecting motion in the longitudinal wheel volume 328, the processor generates a longitudinal wheel 318 and instructs the user display 122 to display the longitudinal wheel 318 (see FIG. 3D).

Figure 4D:
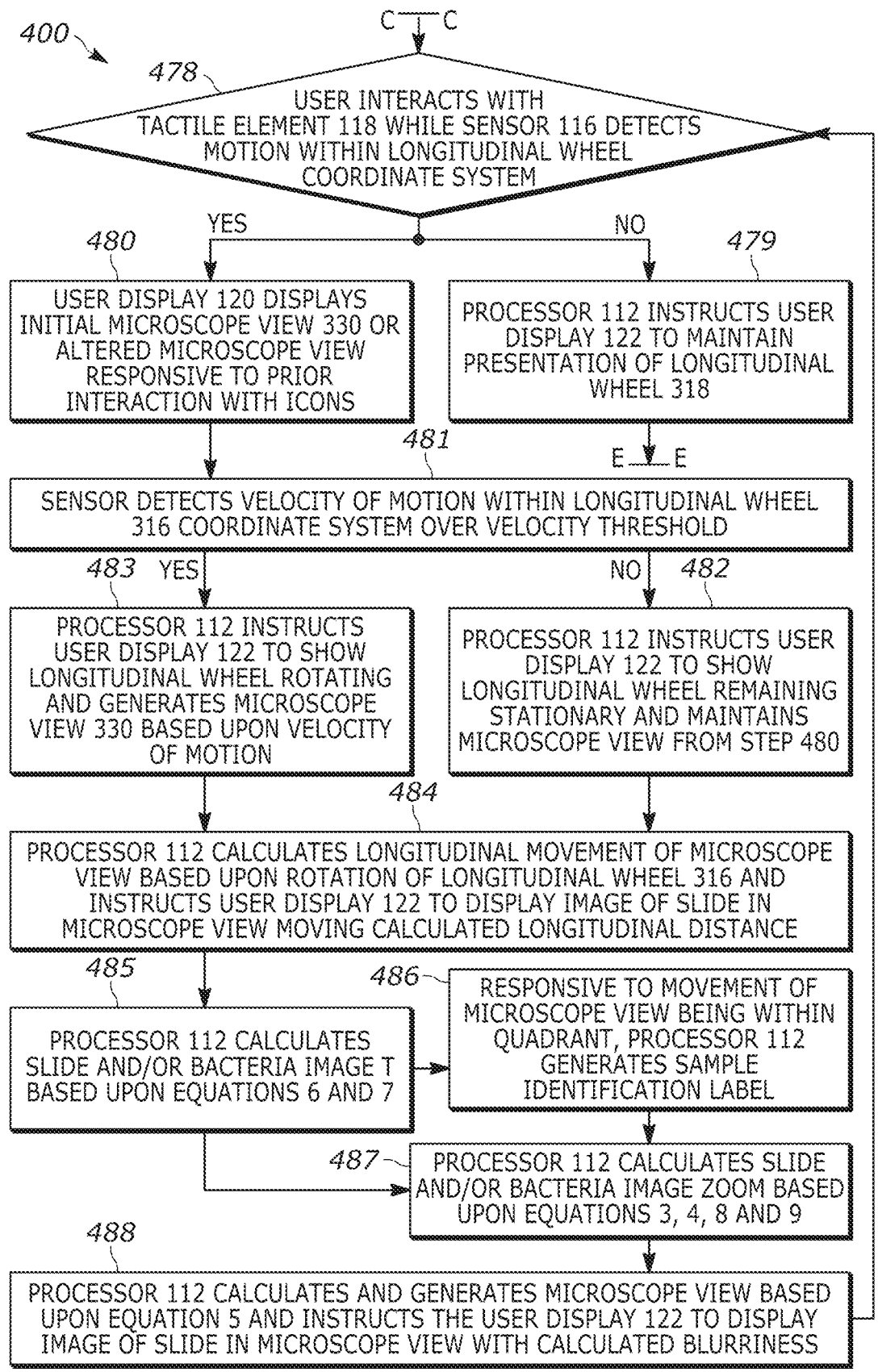
FIG. 4D is a schematic diagram of a method of using a longitudinal function in a selected microscope simulation generated by an example virtual reality system, according to one example embodiment of the present disclosure.

As continued in example method 400 in FIG. 4D, continued from section line C-C, at 478, the virtual reality system 100 determines if the user is interacting with the tactile element 118 while the sensor 116 detects motion within the longitudinal wheel coordinate system. At 479, responsive to the user not interacting with the tactile element 118 and the sensor 116 not detecting motion within the longitudinal wheel coordinate system, the processor 112 instructs the user display 122 to maintain presentation of the longitudinal wheel 318. In this example embodiment, the processor 112 instructs the user display 122 to continue to display the icons 304, 406, 308, 310, and/or the oil dropper 334 when displaying the longitudinal wheel 318. In another example embodiment, the processor 112 instructs the user display 122 to remove the icons 304, 406, 308, 310, and/or the oil dropper 334 when displaying the longitudinal wheel 318. At 430, 432, as illustrated in FIG. 4A, at section line E-E, responsive to the sensor 116 detecting motion outside the respective wheel coordinate system and/or the user disengaging the tactile element 118, the processor 112 instructs the user display 122 to revert to displaying the focus icon 304, the lateral icon 306, the longitudinal icon 308, the objective icon 310 and/or the oil dropper 334 (see FIG. 3A).

At 480, the processor generates and instructs the user display 122 to continue to display the initial microscope view 330 (see FIG. 3L1) and/or an altered microscope view (see FIGS. 3M1-3M4) based upon user interaction with other icons (see FIG. 3A, add FIGS. 3K-3N). At 481, the sensor 116 detects a velocity/degree of rotation of a motion within the longitudinal wheel 318 coordinate system. At 483, responsive to the velocity of d motion within the longitudinal wheel 318 coordinate system being above a velocity threshold, the processor 112 instructs the user display 122 to show the longitudinal wheel 318 rotating and generates and instructs the user display 122 to show a microscope view 330 based upon the velocity/degree of rotation of the motion. At 482, responsive to the velocity/degree of rotation of the motion within the longitudinal wheel 318 coordinate system being below a velocity threshold, the processor 112 instructs the user display 122 to show the longitudinal wheel 318 remaining stationary and instructs the user display 122 to continue to show the microscope view 330 displayed at step 480. The processor 112 also instructs the user display 122 to show a microscope stage 343 and slide 342 moving left or right (see FIGS. 3G, 3M1-3M4). At 494, the processor 112 calculates a longitudinal movement of the microscope view based upon the rotation bf the longitudinal wheel 318 and instructs the user display 122 to display images of the slide 342 in the microscope view moving a calculated longitudinal distance through the following equations. At 485, the processor 112 calculates a longitudinal movement of the microscope view (e.g., translated images slide_image_t and bacteria_image_t) utilizing Equations 6 and 7 above.

The slide_image_t and a bacteria_image_t are calculated in the same manner described above with regard to the lateral movement calculated using Equations 6 and 7 above, except that stage_x is a variable that depends on the velocity of the motion of the longitudinal wheel 318. In an example embodiment, stage_x starts at 0.5, and one rotation clockwise corresponds td stage_x=1.0, and one rotation counter-clockwise corresponds to stage_x=0.0. Stage_y remains constant, and is dependent upon movement of the lateral wheel 316.

At 486, responsive to the movement of the microscope view 330 being within a single quadrant 342a-342d of the slide 342 (see FIG. 3J), the processor 112 generates and instructs the user display 122 to display the sample identification label (see FIG. 3N). Responsive to the movement of the microscope view 330 being outside the single quadrant 342a-342d of the slide 342, the processor 112 does not generate or instruct the user display 122 to display the sample identification label. At 487, the processor 112 calculates a zoom of the microscope view utilizing Equations 8 and 9 as described above at step 474 illustrated in FIG. 4C.

Stage_x is the same variable as described above with regard to Equations 6 and 7. Stage_y remains constant, and is dependent upon movement of the lateral wheel 316. At 487, the processor 112 calculates the slide_image_b and bacteria_image_b using Equations 3 and 4 above, then calculates the Microscope View 330 utilizing Equations 5, 10, and 11 above, and instructs the user display 122 to display the microscope view 330 that corresponds to the longitudinal movement instigated by the motion of the user and the longitudinal wheel 318. In the illustrated example embodiment of FIG. 3M, the longitudinal wheel 318 has been utilized by the user to generate an altered microscope view 330 wherein the slide 342 has been moved along direction B, such that only side portions of quadrants 342a, 342c are visible. In the illustrated example embodiment of FIGS. 3M1-M2, the longitudinal wheel 318 has been utilized by the user to generate an altered microscope view 330 wherein the slide 342 has been moved along direction D a maximum distance. In the illustrated example embodiment of FIGS. 3M3-M4, the longitudinal wheel 318 has been utilized by the user to generate an altered microscope view 330 wherein the slide 342 has been moved along direction B a maximum distance.

The method 400 returns to 478, wherein the user may proceed with adjusting the longitudinal wheel 318 again or by proceeding with steps 479, 430, 432, and 434 the user may proceed to the focus wheel 314 (steps 436-454) or the lateral wheel 316 (steps 460-476), or may proceed to objective wheel 320 or oil dropper 334.

Objective Wheel 320

At 426, the sensor 116 detects motion in an objective wheel volume 332 defined by the objective icon 310 (see FIGS. 3A, 3F). At 428, responsive to the sensor 116 detecting motion in the objective wheel volume 332, the processor generates an objective wheel 320 and instructs the user display 122 to display the objective wheel 320 (see FIG. 3E).

Figure 4E:
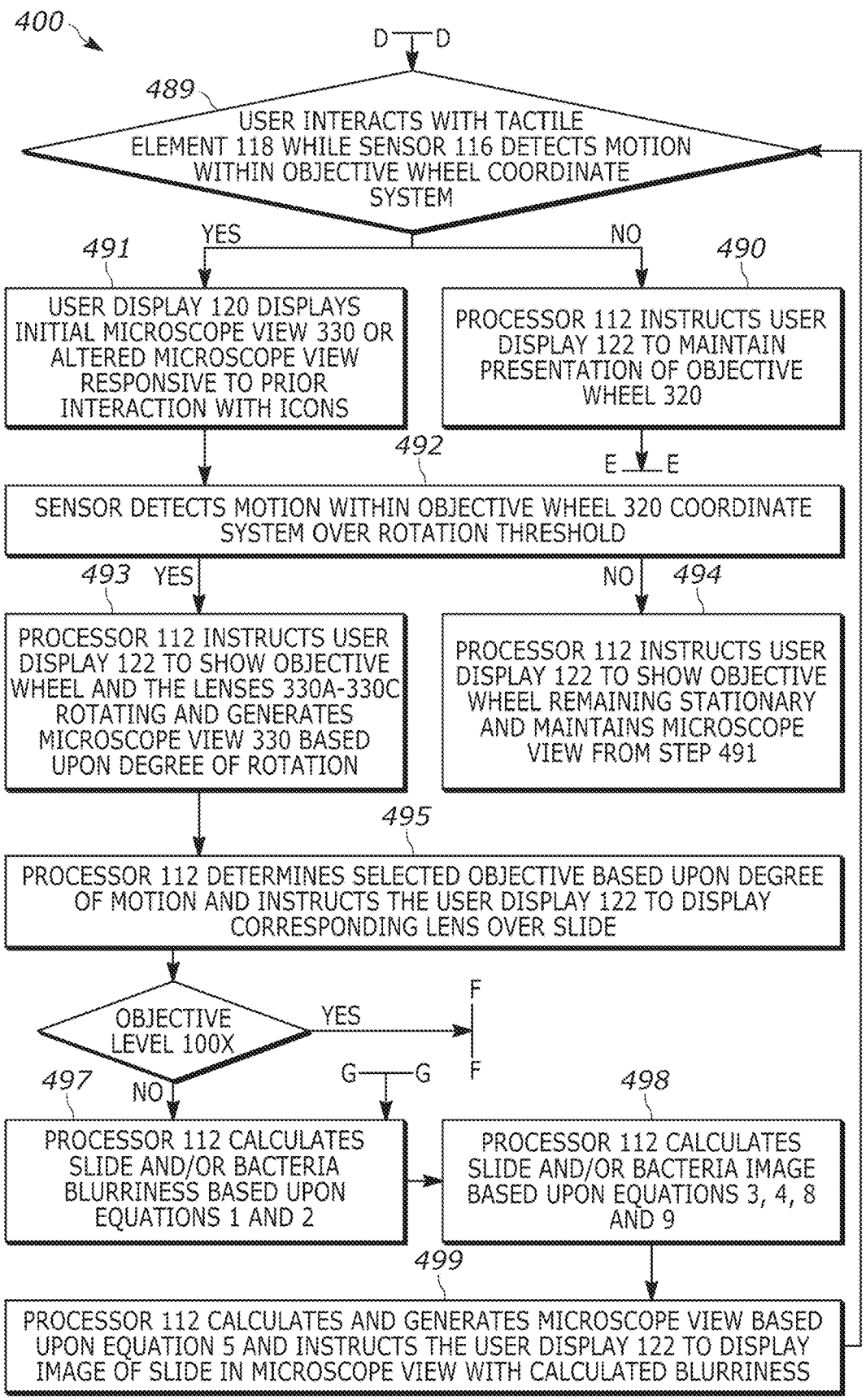
FIG. 4E is a schematic diagram of a method of using an objective function in a selected microscope simulation generated by an example virtual reality system, according to one example embodiment of the present disclosure.

As continued in example method 400 in FIG. 4E, continued from section line D-D, at 489, the virtual reality system 100 determines if the user is interacting with the tactile element 118 while the sensor 116 detects motion within the objective wheel coordinate system. At 490, responsive to the user not interacting with the tactile element 118 and/or the sensor 116 not detecting motion within the objective wheel coordinate system, the processor instructs the user display 122 to maintain presentation of the objective wheel 320. In this example embodiment, the processor 112 instructs the user display 122 to continue to display the icons 304, 406, 308, 310, and/or the oil dropper 334 when displaying the objective wheel 320. In another example embodiment, the processor 112 instructs the user display 122 to remove the icons 304, 406, 308, 310, and/or the oil dropper 334 when displaying the objective wheel 320. At 430, 432, as illustrated in FIG. 4A, at section line E-E, responsive to the sensor 116 detecting motion outside the respective wheel coordinate system and the user disengaging the tactile element 118, the processor 112 instructs the user display 122 to revert to displaying the focus icon 304, the lateral icon 306, the longitudinal icon 308, the objective icon 310, and/or the oil dropper 334.

At 491, the processor generates and instructs the user display 122 to continue to display the initial microscope view 33b and/or an altered microscope view based upon user interaction with other icons (see FIG. 3A, and FIGS. 3K-3N). At 492, the sensor 116 detects a motion within the objective wheel coordinate system. At 493, responsive to the motion within objective wheel 320 coordinate system being above a rotation threshold, the processor 112 instructs the user display 122 to show the objective wheel 320 and lenses 330A-330C (see FIGS. 3G-3H) rotating, and the processor generates and instructs the user display 122 to show a microscope view 330 based upon the degree of the rotation motion. In the example embodiment of FIGS. 3G and 3H, a first lens 330A corresponds to a first objective level (e.g., 10×), a second lens 3301 corresponds to a second objective level (e.g., 40×), and a third lens 330C corresponds to a third objective level (e.g., 100×). It would be appreciated by one having ordinary skill in the art that more or fewer lenses with differing objective levels (e.g. 35×, 55×, 75×, etc.) may be present. At 494, responsive to the motion within objective wheel coordinate system being below the rotation threshold, the processor 112 instructs the user display 422 to show the objective wheel 320 and lenses 330A-330C (see FIGS. 3G-3H) remaining stationary and instructs the user display 122 to continue to show the microscope view 330 displayed at step 491. At 495, the processor 112 determines the selected objective level based upon the degree of motion and instructs the user display 122 to display the corresponding lens 330A-330C over the slide 342.

Figure 4F:
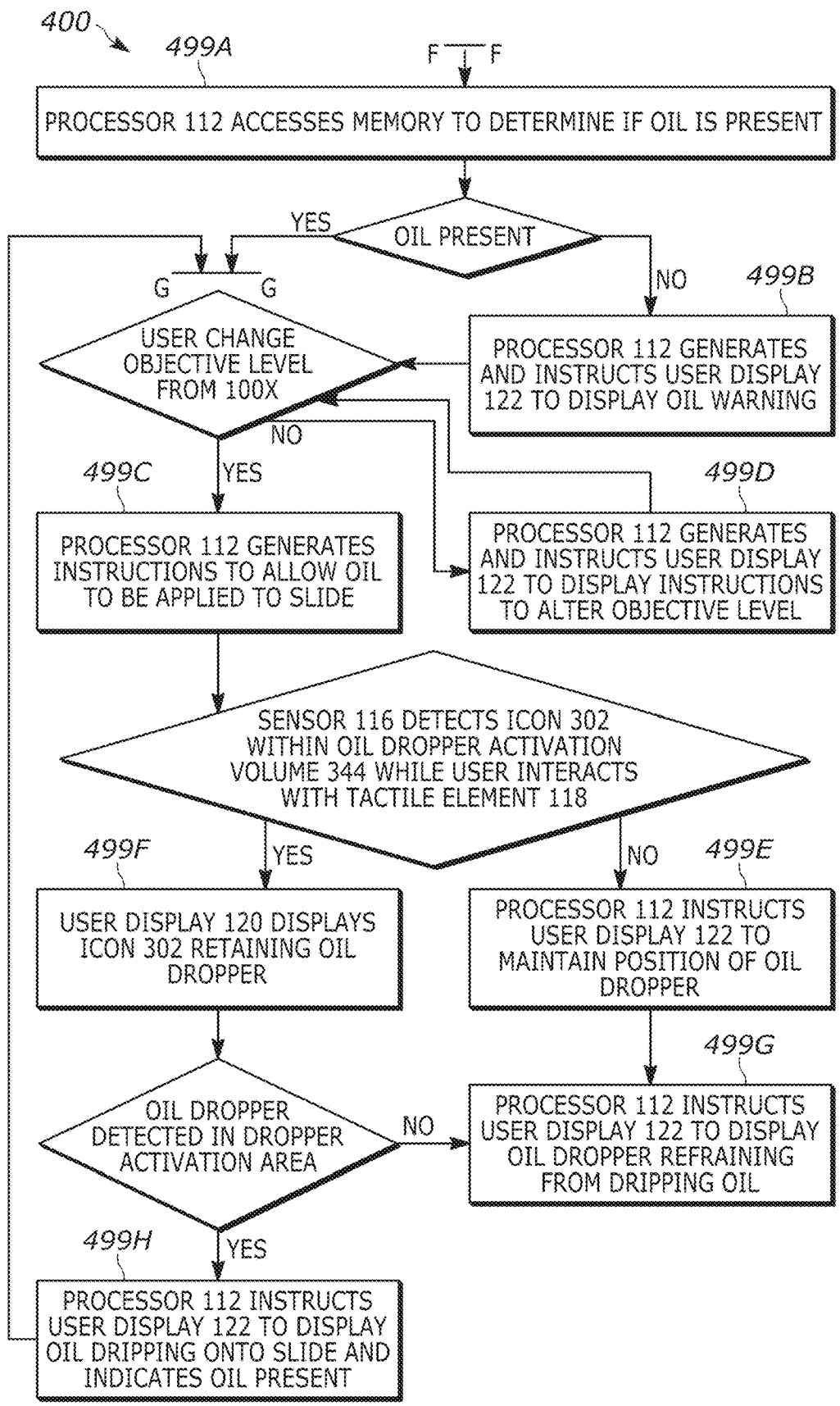
FIG. 4F is a schematic diagram of a method of using an oil function in a selected microscope simulation generated by an example virtual reality system, according to one example embodiment of the present disclosure.

At 499A, as illustrated in FIG. 4F, at section line F-F, responsive to the objective level being over or equal to 100×, the processor 112 accesses memory to determine if oil is present on the slide 342. Responsive to oil being present, the processor 112 sets variable no_oil_multiplier to 1.0 and the processor 112 proceeds to step 497 illustrated at section line G-G on FIG. 4E. At 499B, responsive to oil not being present, the processor 112 sets variable no_oil_multiplier to 0.9 and generates and instructs the user display 122 to display an oil warning 333 (see FIG. 3H1). In one example embodiment, the oil warning 333 is presented to the user on the user display 122, based upon the processor's 112 instruction as the user is attempting td switch the objective level to 100× (e.g., before the microscope objective is altered to 100×). In another example embodiment, the oil warning 333 comprises text stating oil is needed. In yet another example embodiment, the oil warning 333 includes bringing attention to an oil dropper 334 (see FIGS. 3A, 3H), such as by providing attention attracting lights, movement, sound, etc. to the oil dropper. At 499C, responsive to the user changing the objective level from 100×, the processor 112 instructs that oil be permitted to-be applied to the slide 342 No_oil_multiplier is set to 1.0 upon switching from 100×. In another example embodiment, responsive to the user changing the objective level from 100×, the processor 112 generates instructions (e.g., text, visual demonstration, etc.) to apply oil to the slide 342. At 499D, responsive to the user not changing the objective level from 100×, the processor 112 generates instructions (e.g., text, visual demonstration, etc.) to alter the objective level. The processor 112 prohibits the addition of oil if objective is 100×, as there would be no room to add oil when the 100× objective is in place over the slide 342. At 499E, responsive to the sensor 116 not detecting the icon 302 within the oil dropper activation volume 344, and/or the user not interacting with the tactile element 118, the processor 112 instructs the user display 122 to display the oil dropper 334 maintaining its position (e.g., not moving). If the user returns the oil dropper 334 to the oil dropper activation volume 344 and interacts with the tactile element 118, the processor 112 instructs user display 122 to return the oil dropper to the oil dropper's original position.

At 499F, responsive to the sensor 116 detecting icon 302 within the oil dropper activation volume 344, while the user interacts with the tactile element 118, the processor 112 instructs the user display 122 to display the icon retaining the oil dropper 334. The oil dropper activation volume 344 is the same or similar to the wheel activation volumes, wherein the dropper bottle comprises the coordinate points (0,0,0). In this example embodiment, the oil dropper 334 being retained by the icon 302 comprises the oil dropper moving with the icon within the user display 122.

At 499G, responsive to the sensor 116 not detecting the oil dropper 334 within a dropper release volume 346 (see, FIG. 3H), the processor 112 instructs the user display 122 to display the oil dropper 334 retaining the oil (e.g., the oil dropper will not drip oil outside of the dropper activation volume 346). In this example embodiment, the dropper release volume 446 is any area directly over the slide (e.g. any plane that resides over the boundaries of the slide 342). At 499H, responsive to the sensor 116 detecting the oil dropper 334 within the dropper release volume 346 and the user interacting with tactile element 118, the processor 112 instructs the user display 122 to display the oil dropper 334 dripping oil onto the slide 342, and indicating the oil is present.

At 497, as illustrated in FIG. 4E, responsive to the objective level being below 100× or oil being present at step 499a, or step 499F as illustrated in FIG. 4F, and continued at section line G-G on FIG. 4E, the processor 112 calculates a slide blurriness and a bacteria blurriness utilizing Equations 1 and 2 above. The slide blurriness and the bacterial blurriness are calculated utilizing the variable no_oil_multiplier wherein oil is added and present in step 499c, wherein the oil being present equals 1, and no oil is added wherein at 495 the selected objective level was below 100×. At 498, the processor 112 calculates the slide image and the bacteria image utilizing equations 8 and 9, then 3 and 4, above. At 499, the processor 112 calculates and generates an altered microscope view based upon Equation 3, 10, and 11 above, by multiplying three (3) images together, and then setting the alpha channel of the result to the vignette mask, thereby generating the microscope view 330 having the indicated objective level.

In the illustrated example embodiment of FIG. 3N, the objective wheel 320 has been utilized by the user to generate an altered microscope view 330 wherein the slide 342 has been magnified to 100×, such that only a single quadrant 342d-342d is visible.

The method 400 returns to 489, wherein the user may proceed with adjusting the objective wheel 320 again or by proceeding with steps 490, 430, 432, and 434 the user may proceed to the focus wheel 314 (steps 436-454), the lateral wheel 316 (steps 460-476), or the longitudinal wheel 318 (steps 478-488), or the oil dropper 334.

Advantageously, the interactive microscope simulation 300 allows users to train on a microscope without damaging an expensive microscope, and without having to provide the user access to a microscope, when microscopes may be in short supply. Further, the user is presented with the fundamental aspects of the microscope, and the physics of said microscope which are ideal for learning how to operate said microscope in the real world. Additionally, the wheel activation volumes provide the ability for the user to use large motions with the controller 130 to adjust the microscope rather than through the adjustment of small knobs, which could require fine motor skills and would be an impediment to learning.

Streaking Simulation 500

Figure 5A:
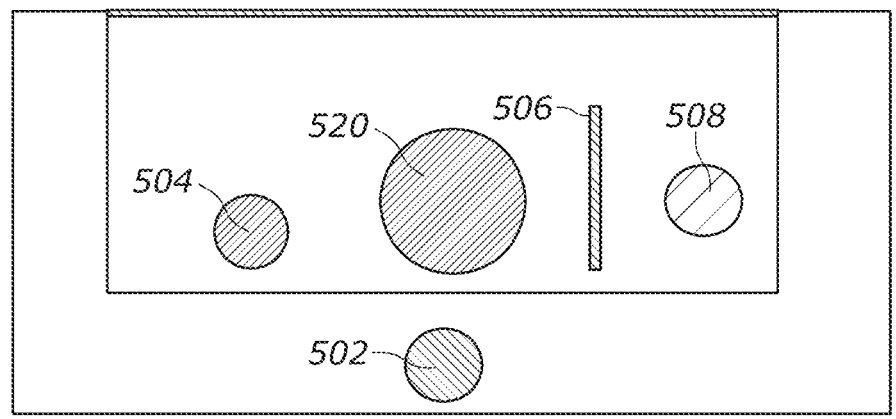
FIG. 5A illustrates a schematic view of a streaking simulation generated by an example virtual reality system, according to one example embodiment of the present disclosure.
Figure 5C:
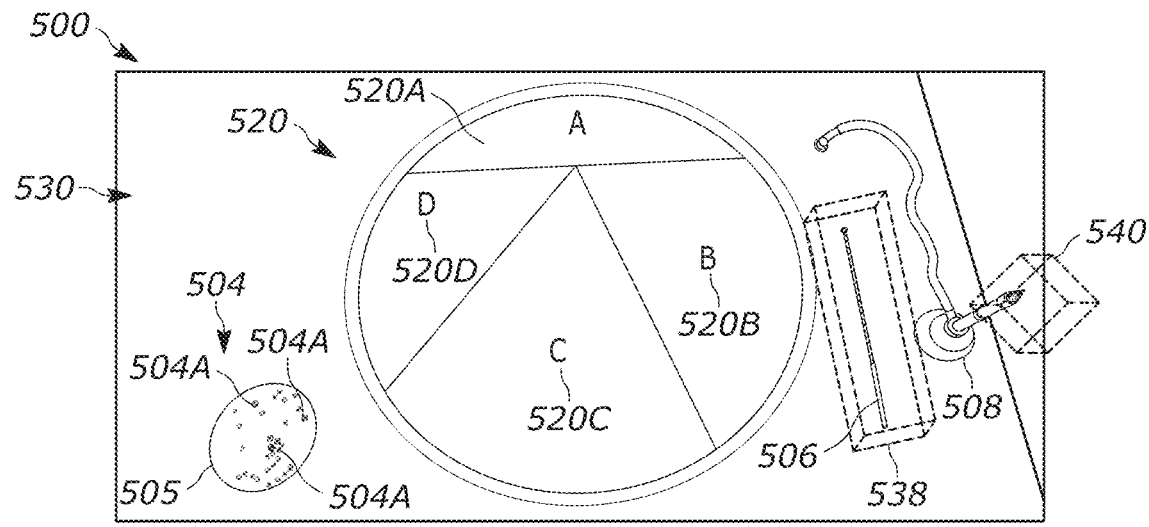
FIG. 5C illustrates a streaking simulation including a streaking plate, a source plate, a heating element and a loop generated by an example virtual reality system, according to one example embodiment of the present disclosure.
Figure 5D:
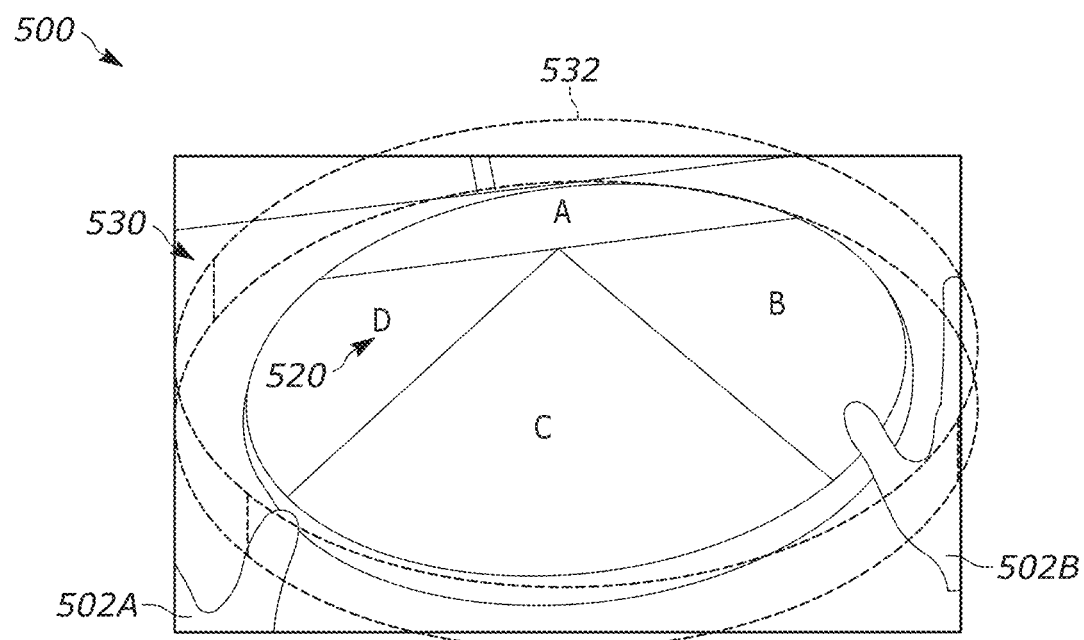
FIG. 5D illustrates a streaking simulation including a streaking plate volume and streaking plate, generated by an example virtual reality system, according to one example embodiment of the present disclosure.
Figure 6A:
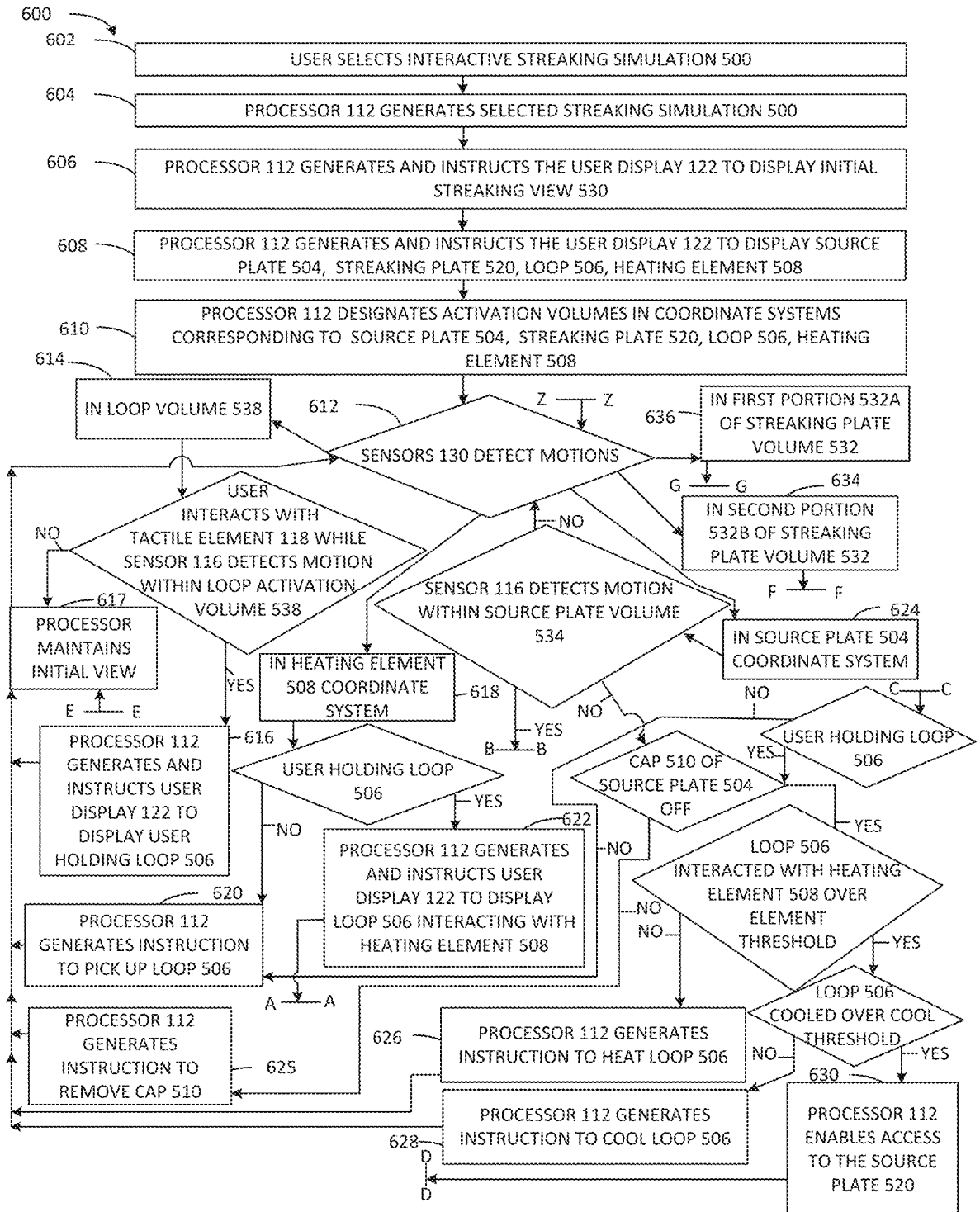
FIG. 6A is a schematic diagram of a method 600 of using a selected streaking simulation generated by an example virtual reality system, according to one example embodiment of the present disclosure.

As illustrated in FIG. 6A, a method 600 of use of the virtual reality system 100 with an interactive streaking simulation 500 is illustrated. At 602, the processor 112 receives a signal indicating the user has selected the interactive streaking simulation 500 (see FIGS. 5A-5U). At 604, the processor 112 generates the interactive streaking simulation 500, including generating a source plate 504, a streaking plate 520, a loop 506, and/or a heating element 508 having a first indicator (e.g., a first appearance that is maintained absence a user input), and instructs the user display 122 to display the streaking simulation 500. At 606, the processor 112 generates and instructs the user display to display an un-streaked plate view 530 (see FIGS. 5A, 5C). A plate view 530 includes an enlarged streaking plate 520 having one or more defined areas. In the illustrated example embodiment of FIG. 5C, the enlarged streaking plate 520 defines four areas/quadrants 520A-530D, wherein the initial plate view 530 illustrates a first quadrant 520A at top portion farthest from the user, a second quadrant 520B at right portion relative to the user, a third quadrant 520AC at bottom portion nearest to the user, and/or a fourth quadrant 520D at left portion relative to the user. The initial plate view 530 comprises the view prior to user input, and subsequent altered initial plate views comprise the views including the user inputs.

Figure 5B:
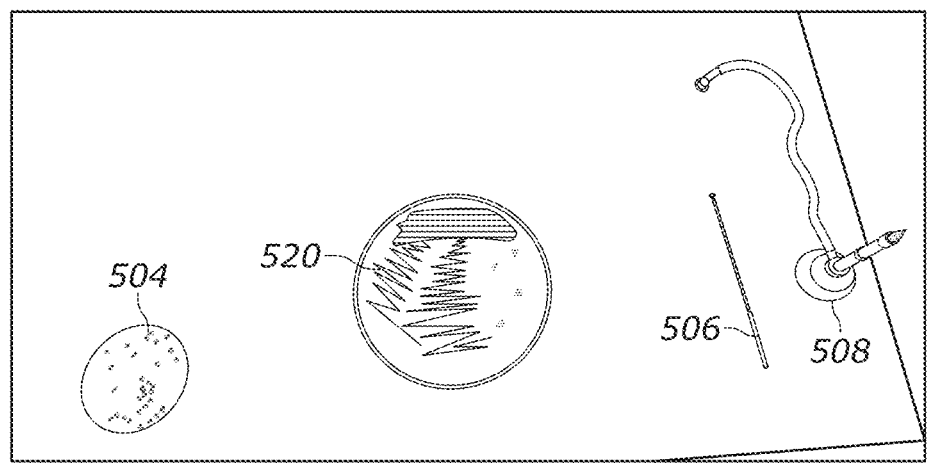
FIG. 5B illustrates a streaking simulation generated by an example virtual reality system, according to one example embodiment of the present disclosure.

At 608, the processer 112 generates and instructs the user display 122 to display the source plate 504, the streaking plate 520, the loop 506, and/or the heating element 508 having the first indicator (see, for example, FIGS. 5A-5C). Steps 604-610 may be performed in any order, and/or may be performed simultaneously.

At 610, the processor 112 designates a first portion 532a or a second portion 532b of a streaking plate volume 532 (see, for example, FIGS. 5D-5H), a source plate volume 534 (see, for example, FIG. 5I), a loop activation volume 538 (see, for example, FIG. 5C), and/or a heating activation volume 540 (see, for example, FIG. 5C), in Cartesian coordinate systems corresponding to the source plate 504, the streaking plate 520, the loop 504 and/or, the heating element 508, respectively.

In another embodiment, the sensor 116 sends a signal to the processor 112 that the controller 130 is within the first portion 532a or the second portion 532b of the streaking plate volume 532 (see, for example, FIGS. 5D-5H). The streaking plate volume comprises a Cartesian coordinate system defining a streaking plate activation distance (e.g. between 6 inches to 12 inches) of the virtual reality streaking plate 520. The streaking plate activation distance defines a three-dimensional volume that extends along x, y, and z axes. In the illustrated example embodiment of FIGS. 5E-5G, the processor 112 receiving the signal the controller 130 is within the first portion 532a, instructs the user display 122 to display a streaking lifting arrow 528. In the illustrated example embodiment of FIG. 5H, the processor 112 receiving the signal the controller 130 is within the second portion 532b, instructs the use display 122 to display streaking mutation arrows 526. In the illustrated example embodiment of FIG. 5I, the processor 112 receiving the signal the controller 130 is within a source plate volume 534, instructs the user display 122 to display source lifting arrow 536.

In another example embodiment, the processer 112 instructs the user display 122 to display, respectively, one of the streaking lifting arrow 528, the streaking rotation arrow 326, and/or the source lifting arrow 536 responsive to the sensor 116 sending a signal to the processor that the controller 130 is within one of the first portion 532a, the second portion 532b, or the source plate volume 534.

In this example embodiment, the volumes 532A, 532B, 534, 538, 540, and/or 542 comprise three dimensional volumes radiating out along x, y, and z axes from a central location (coordinates 0,0,0) wherein the respective icon (e.g., streaking plate 520, source plate 504, loop 506, heating element 508) is located, or a center point of the respective icon. In this embodiment, the volumes 532A, 532B, 534, 538, 540, and/or 542 extend between 1 inch to about 7 inches along the x axis, between 1 inch to about 7 inches along the y axis, and/or between 1 inch to about 7 inches along the z axis, wherein the volume defined within comprises the respective activation volumes. Inches in vertical space is based upon perceived distance by the user. At 12 the sensor 116 detects motion.

Loop 506

At 614, the sensor 116 detects motion in the loop activation volume 538 defined by the loop 506 (FIG. 5C). At 616, responsive to the virtual reality system 100 receiving a signal that the user is interacting with the tactile element 118 while the sensor 116 detects motion within the loop activation volume 538, the processor 112 instruct the user display 12 to display a user icon 502 (e.g., same or similar to the user icon 302 described above) holding the loop 506. In this embodiment, the user icon 502 retains the loop 504 until the processor 112 receives a signal that the user, holding the loop, is interacting with the tactile element 118 while the sensor 116 detects motion within the loop activation volume 538, wherein the processor instructs the user display 122 to show the user relinquishing the loop and the loop returns to its initial position (see FIG. 5B). The processor 112 disallows the user holding the loop 504 or other element with the user icon 502 from picking up any additional items, until the respective item is put down. At 617, responsive to the user not interacting with the tactile element 118 and/or the sensor 116 not detecting motion within the loop activation volume 538, the processor instructs the user display 122 to maintain the initial streaking view 530. Wherein, at 612, the sensor 116 may detect motion in any of the volumes 532A, 532B, 534, 538, 540, and/or 542.

Heating Element 508

Figure 6B:
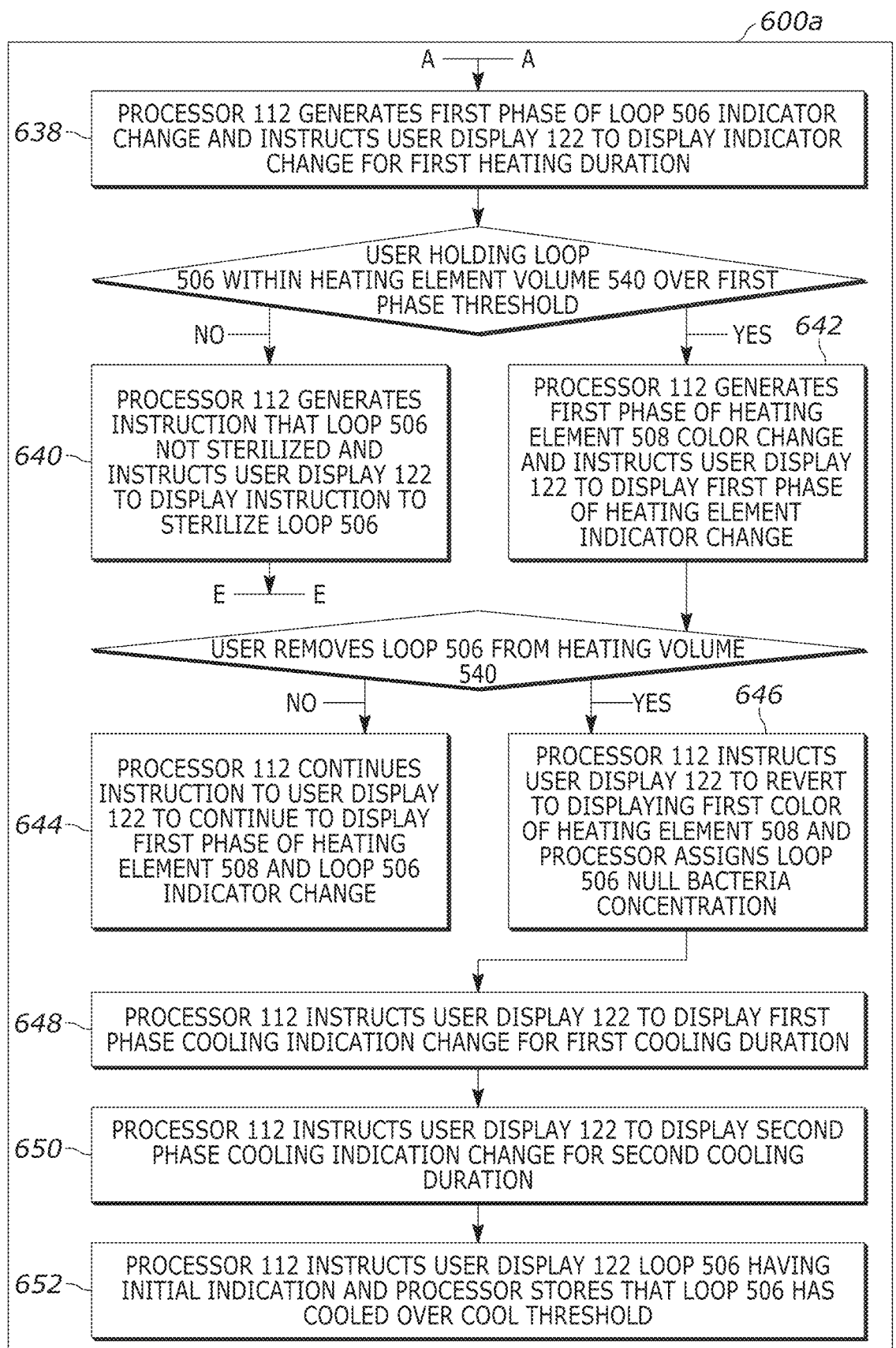
FIG. 6B is a schematic diagram of a method 600 of using a loop sterilization process in a selected streaking simulation generated by an example virtual reality system, according to one example embodiment of the present disclosure.

At 618, the sensor 116 detects motion in the heating activation volume 540 defined by the heating element 508 (FIG. 5C). At 622, responsive to the virtual reality system 100 having stored that the user icon 302 is holding the loop 504, the processor 112 generates and instructs the user display 122 to display the loop 504 interacting with the heating elements 508 (see FIG. 5J). As continued in example method 600 in FIG. 6B is loop sterilization process 600d. The loop sterilization process 600a is continued from section line A-A of FIG. 6A, at 638, the processor generates a first phase 507a of a loop heating indication (e.g., color or texture change, and/or text notice of heating) responsive the sensor 116 detecting the loop 54 in the heating volume 540 for a first heating duration (see FIG. 5K). In one example embodiment, the first heating duration is between 1 seconds and 4 seconds. In another example embodiment, the first heating duration is 2 seconds. The first phase 507a corresponds to a loop temperature, wherein a number from zero to one is assigned to the loop. Zero represents room temperature, while one corresponds to when the loop is in the first phase 507a. At 640, responsive to the user not holding the loop 506 within the heating volume 540 over a first phase threshold, the processor generates an instruction (e.g., text or audible) that the loop 504 has not been sterilized and instructs the user display 122 to display the instruction (e.g., to sterilize loop).

At 617, as illustrated in FIG. 6A, at section line E-E, responsive to the processor 112 determining the loop is not sterilized, the processor instructs the user display 122 to maintain the initial streaking view 530. At 612, responsive to the user failing to sterilize the loop 504, the sensor 116 may detect motion in any of the volumes 532A, 532B, 534, 538, 540, and/or 532.

Figure 5E:
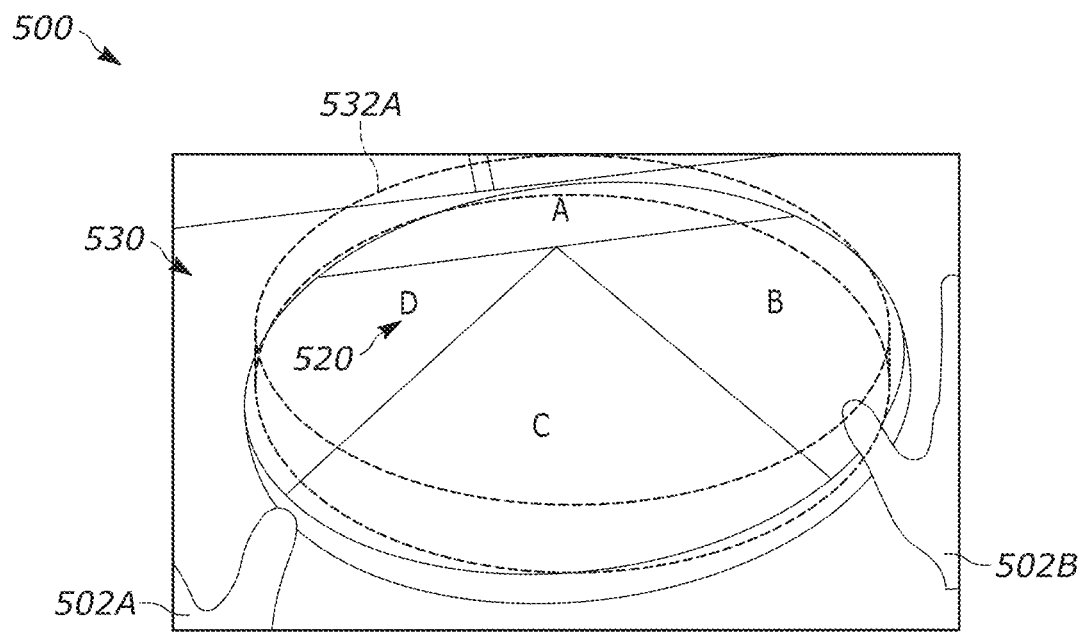
FIG. 5E illustrates a streaking simulation including a first portion of a streaking plate volume and streaking plate, generated by an example virtual reality system, according to one example embodiment of the present disclosure.
Figure 5F:
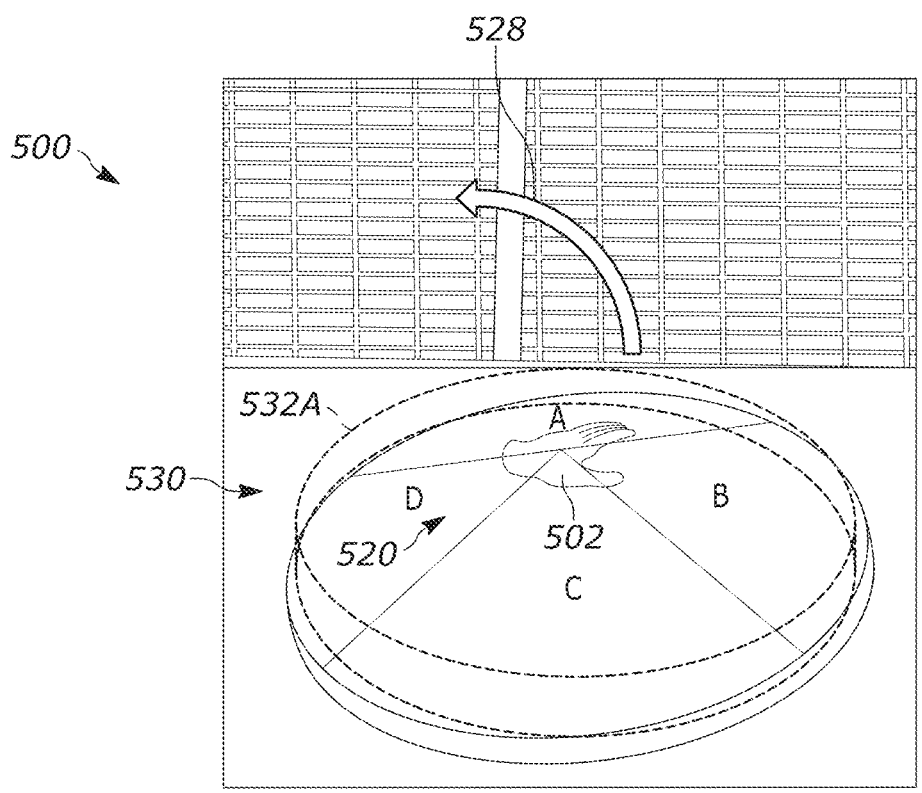
FIG. 5F illustrates a streaking simulation including a view of a lifting arrow generated based upon interaction in a first portion of a streaking plate volume, generated by an example virtual reality system, according to one example embodiment of the present disclosure.
Figure 5G:
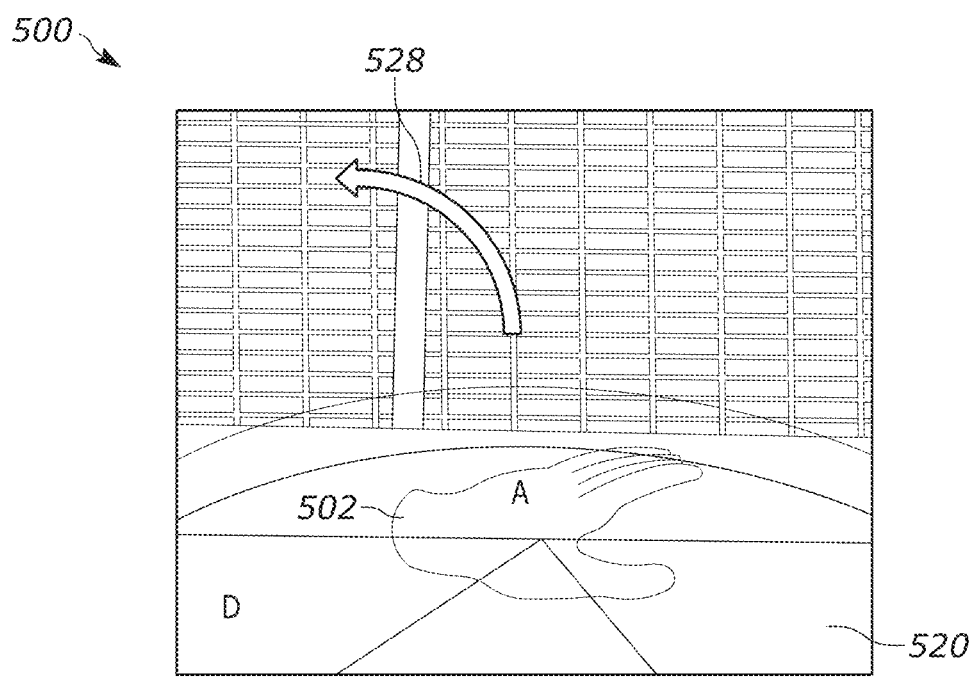
FIG. 5G illustrates a streaking simulation including a magnified view of a lifting arrow generated based upon interaction in a first portion of a streaking plate volume, generated by an example virtual reality system, according to one example embodiment of the present disclosure.
Figure 5H:
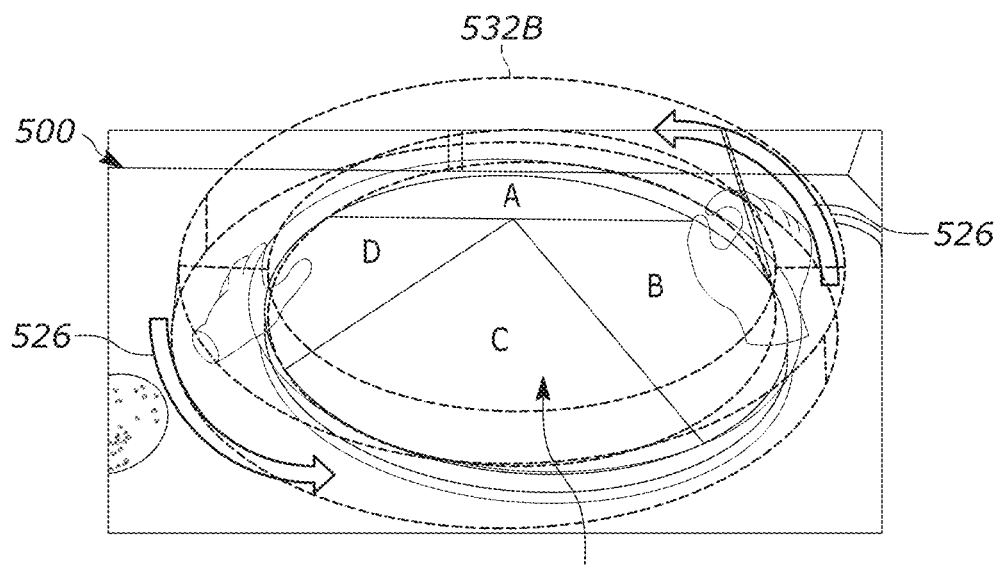
FIG. 5H illustrates a streaking simulation including a second portion of a streaking plate volume hand streaking plate, generated by an example virtual reality system, according to one example embodiment of the present disclosure.
Figure 5I:
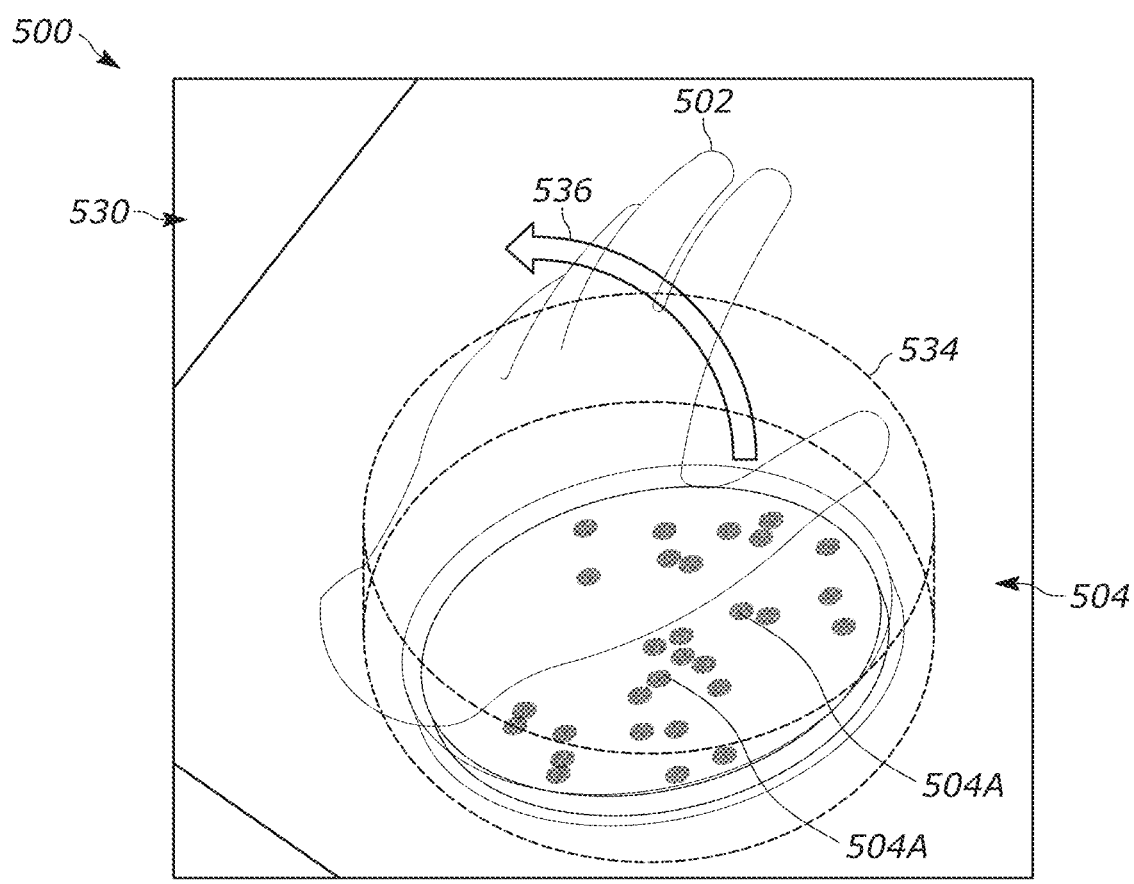
FIG. 5I illustrates a streaking simulation including a source volume and source plate including a source lifting arrow generated based upon interaction in the source volume, generated by an example virtual reality system, according to one example embodiment of the present disclosure.
Figure 5J:
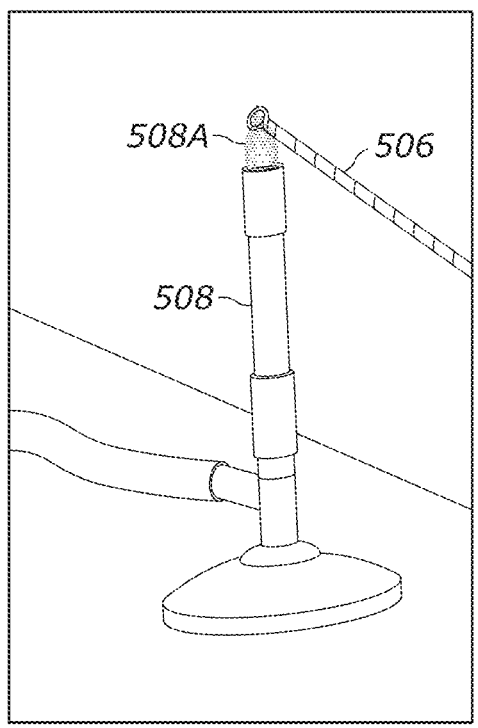
FIG. 5J illustrates a heating element first phase interaction with d loop in a streaking simulation generated by an example virtual reality system, according to one example embodiment of the present disclosure.
Figure 5K:
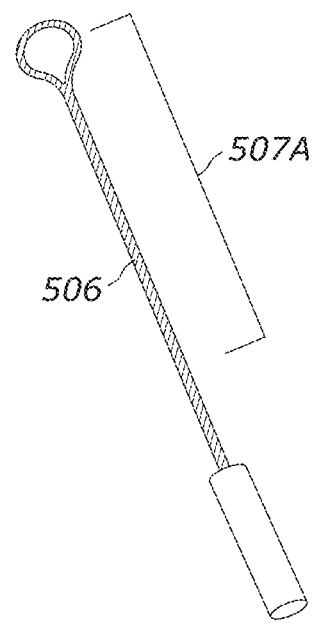
FIG. 5K illustrates a loop in a first heating phase in a streaking simulation generated by an example virtual reality system, according to one example embodiment of the present disclosure.
Figure 5L:
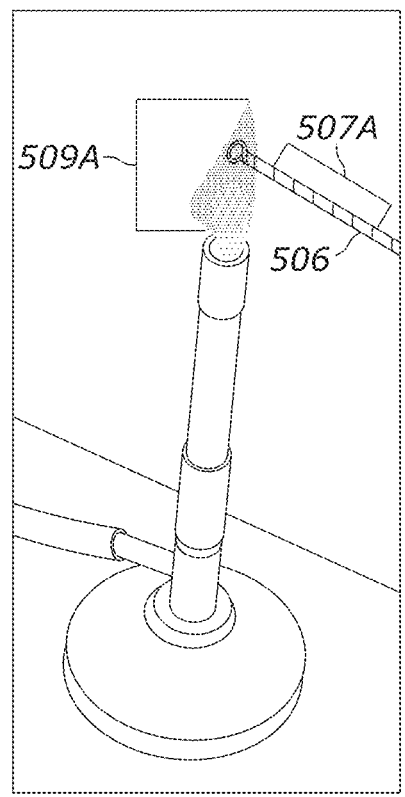
FIG. 5L illustrates a heating element second phase interaction with a loop in first heating phase in a streaking simulation generated by an example virtual reality system, according to one example embodiment of the present disclosure.
Figure 5M:
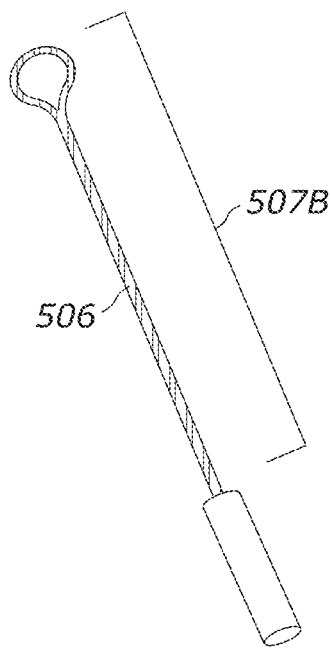
FIG. 5M illustrates a loop in a first cooling phase in a streaking simulation generated by an example virtual reality system, according to one example embodiment of the present disclosure.
Figure 5N:
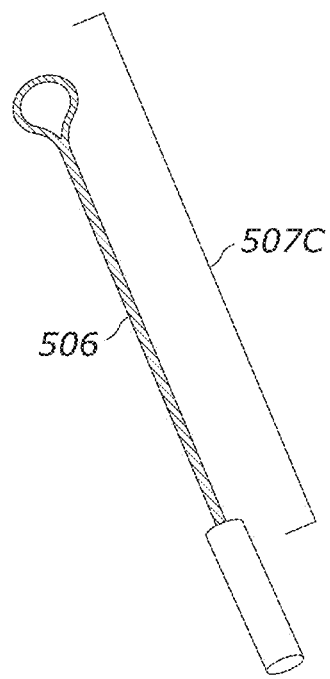
FIG. 5N illustrates a loop in a second cooling phase in a streaking simulation generated by an example virtual reality system, according to one example embodiment of the present disclosure.
Figure 5O:
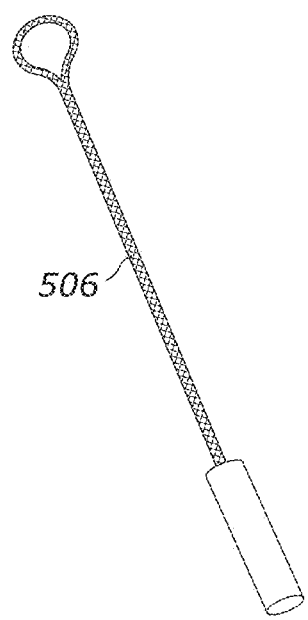
FIG. 5O illustrates a loop in a streaking simulation generated by an example virtual reality system, according to one example embodiment of the present disclosure.

At 642, responsive to the user holding the loop 506 within the heating volume 540 over a first phase threshold, the processor 120 generates a first phase 509a heating element indication (e.g., color or texture change, and/or text notice of heating) (see FIG. 5L). In one example embodiment, the first phase threshold is between 1 seconds and 4 seconds. In another example embodiment, the first phase threshold is 5 seconds. At 644, responsive to the sensor 116 not detecting the user removing the loop 504 from the heating volume 540, the processor 112 instructs the user display 122 to continue to display the loop 504 having the first phase 507a indicator and the heating element 508 having the first phase 509a indicator.

At 646, responsive to the sensor 116 detecting the user removing the loop 504 from the heating volume 540, the processor 112 instructs the user display 122 to revert to displaying an initial indication phase of the heating element 508 (see FIG. 5C) and the processor 112 assigns the loop 506 a null bacteria concentration (e.g., a concentration of 0). At 648, the processor 112 instruct the user display 122 to display a first phase cooling indication change 507b (see FIG. 5M) (e.g., color or texture change, and/or text notice of cooling) after a first cooling duration. In one example embodiment, the first cooling duration is between 1 seconds and 2 seconds. In another example embodiment, the first cooling duration is 1.5 seconds. In one example embodiment, the loop 504 changes color from a hot color, such as bright white, yellow, to a relatively less bright yellow or orange. At 650, the processor 112 instruct the user display 122 to display a second phase cooling indication change 507c (see FIG. 5N) (e.g., color or texture change, and/or text notice of cooling) after a second cooling duration. In one example embodiment, the second cooling duration is between 1 seconds and 4 seconds. In another example embodiment, the first cooling duration is 3.5 seconds. In one example embodiment, the loop 504 changes color from a warm color, such as the relatively less bright yellow or orange, to an even less bright red or orange.

At 652, the processor 112 instruct the user display 122 to display the loop 504 having an initial indication (see FIGS. 5C, 5O) (e.g., color or texture change, and/or text indicates the loop has returned to its initial temperature) after the second cooling duration, wherein the processor stores that the loop has cooled over a cool threshold. It Would be appreciated by one having ordinary skill in the art that durations or limits of the first and second cooling durations and/or the first phase threshold may be altered by inputs to the processor 112.

As illustrated in FIG. 6A, at 617, the processor instructs the user display 122 to maintain the initial streaking view 530. At 612, the sensor 116 may detect motion in any of the volumes 532A, 532B, 534, 538, 540, and/or 542 Wherein absent contaminating acts (e.g., touching the loop 504 to non-sterile areas) the processor 112 stores that the loop 504 has interacted with the heating element 508 over the heating element threshold and cooled over the cool threshold.

Source Plate 504

At 624, the sensor 116 detects motion in the source volume 534 defined by the source plate 504 (FIG. 5I). At 625, responsive to the cap 510 not being off of the source plate 504, the processor 112 generates instructions to remove the cap (e.g., text, visual, and/or audio). In one example embodiment, the cap 510 being on the source plate 504 prevents access to the bacterial colony 504a, and no instruction is generated. At 611, responsive to the user not having removed the cap 7510, the processor 112 instructs the user display 122 to maintain the initial streaking view 530. Wherein, at 612, the sensor 116 may detect motion in any of the volumes 532A, 532B, 534, 538, 540, and/or 532.

Figure 6C:
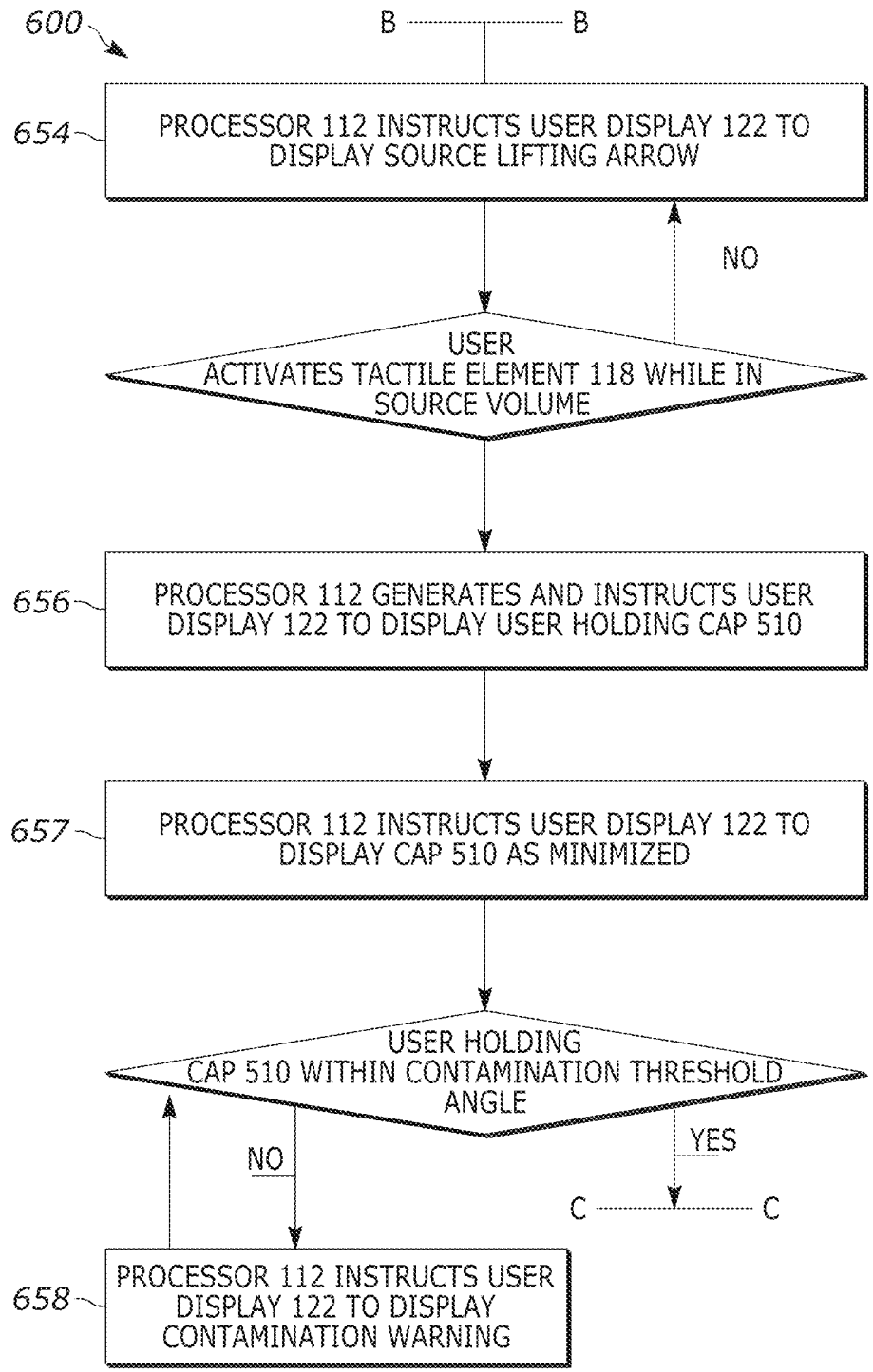
FIG. 6C is a schematic diagram of a method 600 of using removing a cap from a source plate in a selected streaking simulation generated by an example virtual reality system, according to one example embodiment of the present disclosure.

At 654, as illustrated in FIG. 6C, at section line B-B, responsive to the virtual reality system 100 receiving a signal that the sensor 116 detects motion within the source volume 534, the processor 112 instruct the user display 122 to display the source lifting arrow 536 (see FIG. 5I). Absent the virtual reality system 100 receiving a signal that the user has activated the tactile element 118 while the sensor 116 detects a continued presence of the controller 130 within the source volume 534, the processor 112 instructs the user display 122 to continue to display the source lifting arrow 536.

Figure 5P:
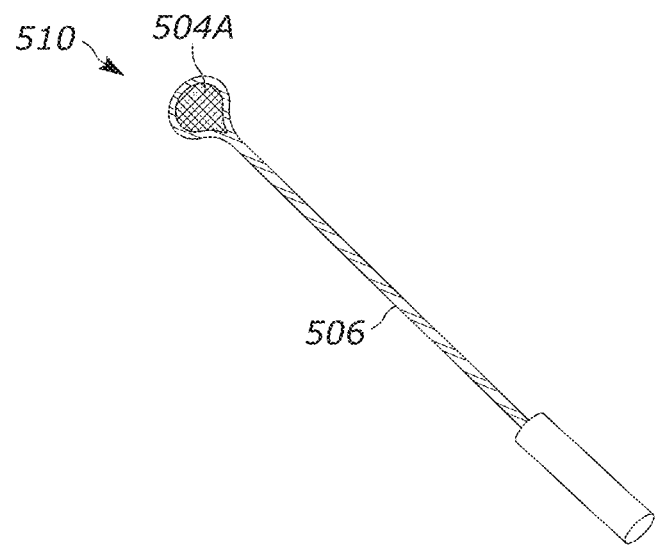
FIG. 5P illustrates a streaking simulation including a streaking plate, a source plate having a cap removed, and a loop generated by an example virtual reality system, according to one example embodiment of the present disclosure.
Figure 5P:
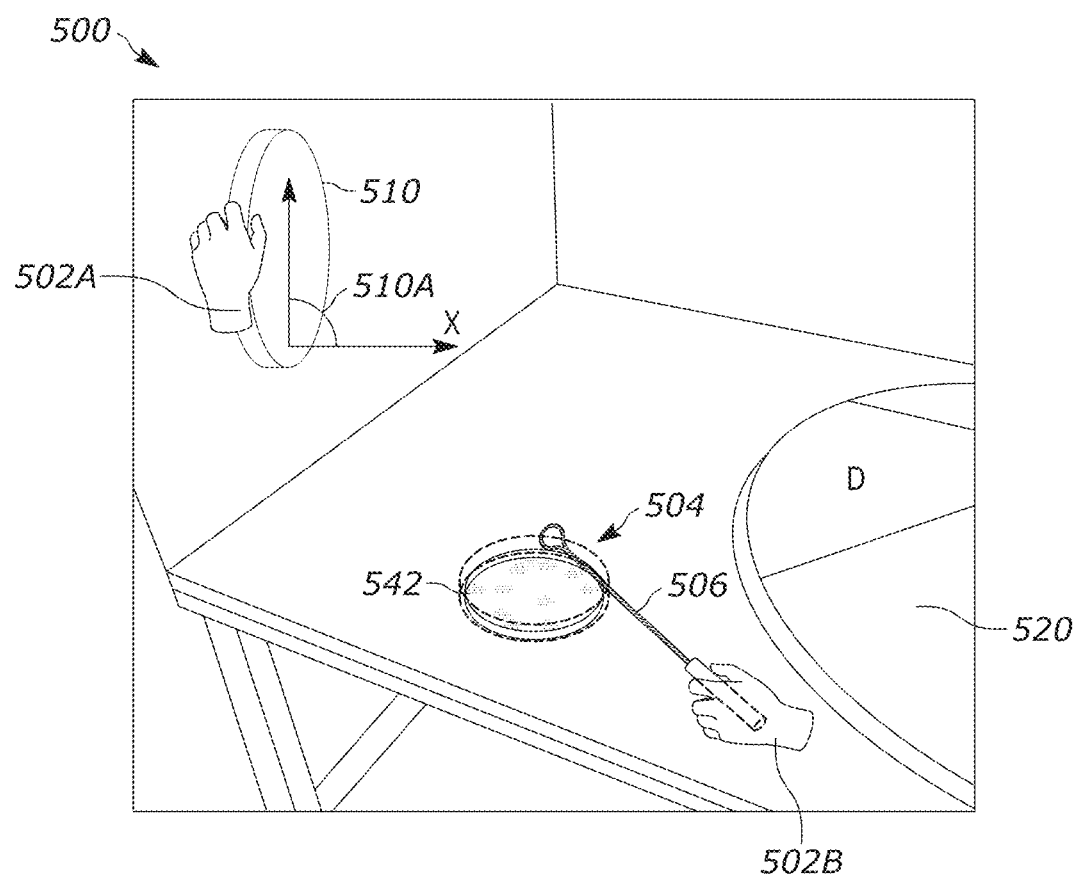

At 656, responsive to the virtual reality system 100 receiving a signal that the user is interacting with the tactile element 118 while the sensor 116 detects motion within the source volume 534, the processor 112 instruct the user display 122 to display the user icon 502 holding the cap 510 (see FIG. 5P). In one example embodiment, responsive to the virtual reality system 100 receiving a signal that the user has continued to actuate the tactile element 118 while the sensor 116 detects the continued presence of the controller 130 within the source volume 534 over a cap lifting duration, the processor 112 instruct the user display 122 to display the user icon 502 holding the cap 510. In one example embodiment, the cap lifting duration is between 1 second to 5 seconds. In yet another example embodiment, responsive to the virtual reality system 100 receiving a signal that the user has continued to actuate the tactile element 118 while the sensor 116 detects a motion of the controller 130 away from the source volume 534 over a velocity threshold, the processor 112 instruct the user display 122 to display the user icon 502 holding the cap 510. In this embodiment, the velocity threshold is between 0.1 foot per second to about 1.5 feet per second. It would be understood by one of ordinary skill in the art that any combination of signals described above could be utilized by the processer 112 to generate instructions to remove the cap 510. At 657, the processor 112 instructs the user display 122 to display the cap 510 as minimized. At 658, responsive to the virtual reality system 106 receiving a signal that the user has moved the cap 510 outside a contamination threshold angle 510a, the processor 122 instructs the user display 122 to display a contamination warning (e.g., text, visual, and/or audio). In this example embodiment, the contamination threshold angle 510a is between 0 degrees to 89 degrees from the x-axis of FIG. 5P. Wherein, responsive to the cap 510 being extended beyond the contamination threshold angle 510a, bacteria in the air may use gravity to land on the inside of said cap 510, which will cause contamination within the source plate 504.

Responsive to the virtual reality system 100 receiving a signal that the user is maintaining the cap 510 within a contamination threshold angle 510*a*, the example method 600 is continued in in FIG. 6A, continued from section line C-C, the processor 122 identifies a status of the loop 504 (e.g., presence in the user icon 502, bacteria count of the loop, and/or temperature of the loop).

At 620, responsive to the processor 112 lacking a stored memory of the user icon 502 holding the loop 504, the processor generates an instruction to pick of the loop (e.g., text, visual, and/or audio). In one example embodiment, no instruction is generated. At 626, responsive to the processor 112 lacking a stored memory that the loop 504 has interacted with the heating element 508 over the heating element threshold (e.g., the loop has been assigned a bacteria count of 0), the processor generates an instruction to heat the loop (e.g., text, visual, and/or audio). At 628, responsive to the processor 112 lacking a stored memory that the loop 504 has cooled from interaction with the heating element 508 over the cool threshold, the processor generates an instruction to cool the loop (e.g., text, visual, and/or audio). From 620, 626, and 628, the method 600 continues to 617, wherein the processor instructs the user display 122 to maintain the streaking view 530. At 612, the sensor 116 may detect motion in any of the volumes 532A, 532B, 534, 538, 540, and/or 532.

At 630, responsive to the processor 112 having the stored memory of the user icon 502 holding the loop 504, the stored memory that the loop 504 has interacted with the heating element 508 over the heating element threshold, and the stored memory that the loop 504 has cooled from interaction with the heating element 508 over the cool threshold, the processor 112 enables access to a top surface 505 supporting one or more bacteria colonies 504*a* of the source plate 520 (see FIG. 5C). In one example embodiment, such as when two controllers 130 are present, the processor 122 receives information from two tactile elements 118 and at least two sensors 116, wherein the processor identifies a location of the first controller 130, and designates a first user icon 502*a* as corresponding to the first controller 130, and a second user icon 502*b* as corresponding to the second controller 130, wherein the first user icon 502*a* may be holding the loop 504 and the second user icon 504*b* may interact with the cap 510, the streaking cap 524, the source lifting arrow 534, streaking lifting arrow 528, the streaking rotation arrow 526, the cap 510, and/or the streaking cap 524 (see FIGS. 5F-5I, 5P-5P1).

Figure 6D:
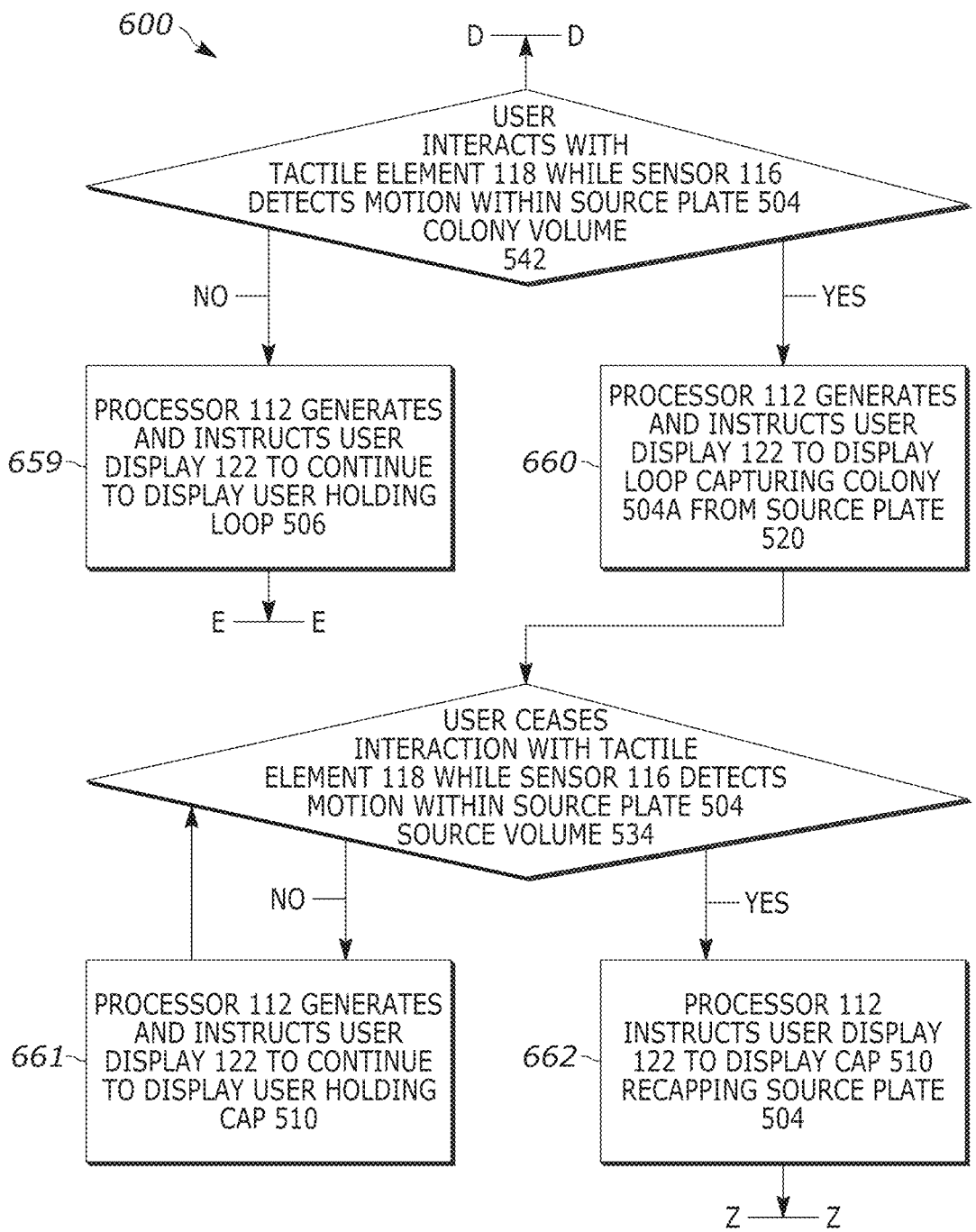
FIG. 6D is a schematic diagram of a method 600 of using a loop to capture a bacterial colony in a selected streaking simulation generated by an example virtual reality system, according to one example embodiment of the present disclosure.

As continued in example method 600 in FIG. 6D, continued from section line D-D, at 659 responsive to the virtual reality system 100 receiving a signal that the user is not interacting with the tactile element 118 or that the sensor 116 does not detect motion within the colony volume 542, the processor 112 instruct the user display 122 to continue to display the user icon 502*b* holding the loop 504 and the user icon 502*a* holding the cap 510 (see FIG. 5P). At 660, responsive to the virtual reality system 100 receiving a signal that the user is interacting with the tactile element 118 while the sensor 116 detects motion within the colony volume 542, the processor 112 instruct the user display 122 to display the loop 506 capturing a colony 504*a* from the source plate (see FIGS. 501-5P). At 661, responsive to the virtual reality system 100 receiving a signal that the user has continued actuate the tactile element 118 or the sensor 116 does not detect a presence of the controller 130 correlated with the user icon 502 holding the source cap 510 within the source volume 534, the processor 112 instruct the user display 122 to display the user icon 502 holding the cap 510 (see FIG. 5P).

At 662, responsive to the virtual reality system 100 receiving a signal that the user has deactivated the tactile element 118 while the sensor 116 detects a presence of the controller 130 correlated with the user icon 502 holding the source cap 510 within the source volume 534, the processor 112 instruct the user display 122 to display the user icon 502 recapping the source plate 504 with the cap 510 (see FIG. 5C). In one example embodiment, responsive to the virtual reality system 100 receiving a signal that the user has continued to actuate the tactile element 118 while the sensor 116 detects the continued presence of the controller 130 within the source volume 534 over a cap replacing duration, the processor 112 instruct the user display 122 to display the user icon 502 recapping the source plate 504 with the cap 510. In one example embodiment, the cap replacing duration is between 1 second to 5 seconds. In yet another example embodiment, responsive to the virtual reality system 100 receiving a signal that the user has continued to actuate the tactile element 118 while the sensor 116 detects a motion of the controller 130 toward the source volume 534 over the velocity threshold, the processor 112 instruct the user display 122 to display the user icon 502 recapping the source plate 504 with the cap 510. At 612, as illustrated in FIG. 6A, at section line Z-Z, the sensor 116 may detect motion in any of the volumes 532A, 532B, 534, 538, 540, and/or 542

Streaking Plate 520

Figure 6E:
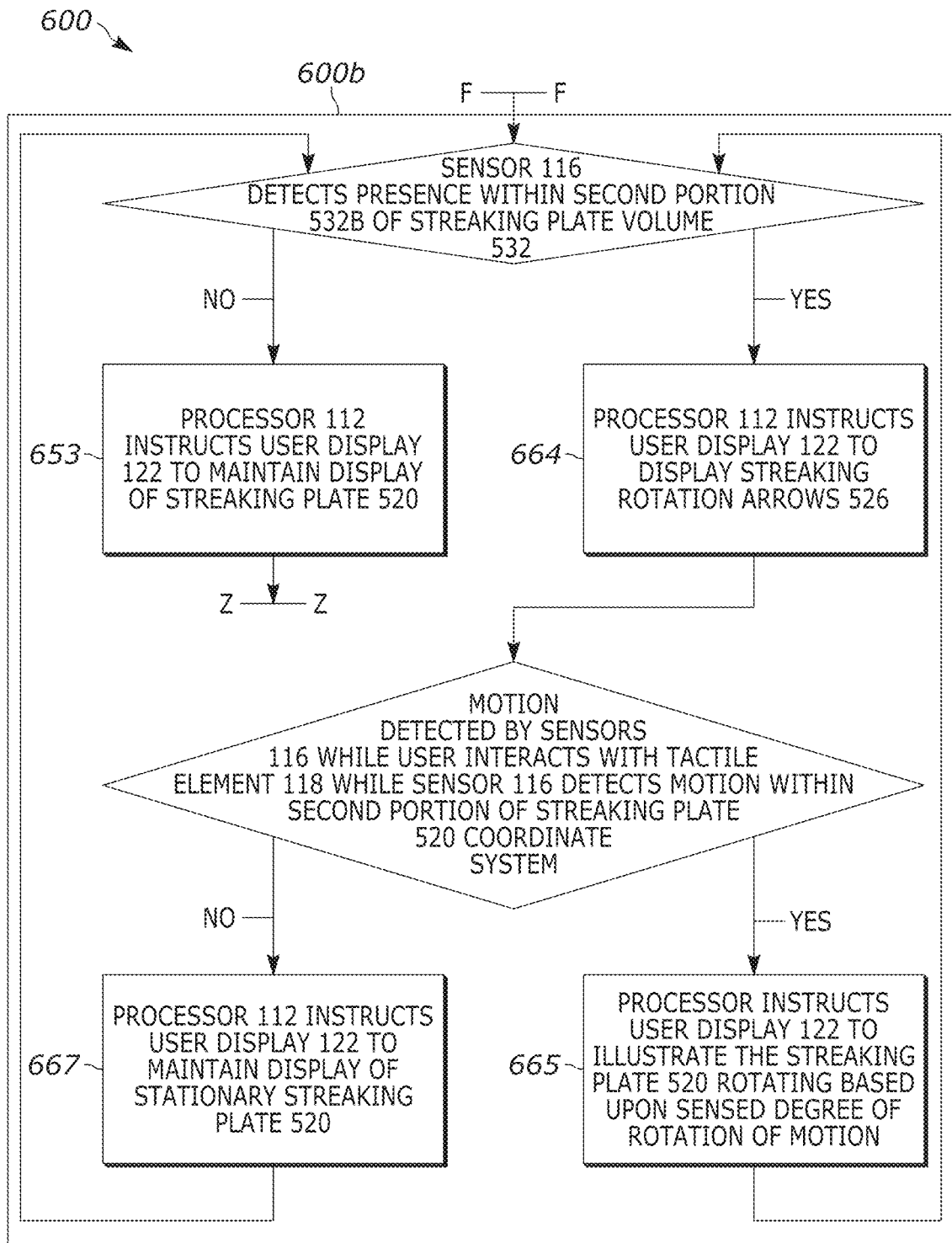
FIG. 6E is a schematic diagram of a method 600 of using a streaking plate rotation process in a selected streaking simulation generated by an example virtual reality system, according to one example embodiment of the present disclosure.

At 634, the sensor 116 detects motion in the second portion 532*b* of streaking plate volume 532 defined by the streaking plate 520 (FIG. 5H). As continued in example method 600 in FIG. 6E, at section line F-F, is streaking plate rotation process 600*b*. The streaking plate rotation process 600*b* begins at 663, as illustrated. At 663 absent the virtual reality system 100 receiving a signal that the user is interacting with the tactile element 118 while the sensor 116 detects a presence of the controller 130 within the second portion 532*b* of the streaking plate volume 532, the processor 112 instructs the user display 122 to continue to display the streaking plate 520 (see FIG. 5C). At 612, as illustrated in FIG. 6A, at section line Z-Z, the sensor 116 may detect motion in any of the volumes 532A, 532B, 534, 538, 540, and/or 532.

At 664, responsive to the virtual reality system 100 receiving that the sensor 116 detects the user's presence within the second portion 532*b* of the streaking plate volume 532, the processor 112 instructs the user display 122 to display the streaking rotation arrows 526 (see FIG. 5H). At 665, responsive to the virtual reality system 100 receiving a signal that the user is interacting with the tactile element 118 while the sensor 116 detects motion within the second portion 532*b* of the streaking plate volume 532, the processor 112 instruct the user display 122 to display the streaking plate 520 rotating based upon a sensed degree of motion (see FIG. 5H). In one example embodiment, responsive to the virtual reality system 100 receiving a signal that the user is interacting with the tactile element 118 while the sensor 116 detects motion within the second portion 532*b* of the streaking plate volume 532, the processor 112 instructs the user display 122 to cease the display of the streaking rotation arrows 526. In another example embodiment, the sensed degree of motion is determined based upon a sensed speed of the controller 130, wherein a first speed corresponds to a first degree of rotation and the faster the first speed the larger the first degree of rotation. In another example embodiment, the sensed degree of motion is determined based upon a rotational movement of the controller 130, wherein a 30-degree rotational movement by the user causes the processor 112 to instruct the user display 122 to display the streaking plate 520 rotating 30 degrees (e.g., a 1:1 relationship, although 1:2, 1:3, etc. relationships are contemplated). It would be understood by one having ordinary skill in the art that a combination of sensed speed and sensed degree of rotation may be used to determine a degree of rotation of the streaking plate 520. At 667, responsive to the virtual reality system 100 receiving a signal that the user is not interacting with the tactile element 118 and/or the sensor 116 does not detect the presence bf the controller 130 within the second portion 532b of the streaking plate volume 532, the processor 112 instruct the user display 122 to maintain the initial view of the streaking plate 520 (see FIG. 5H).

In this embodiment, the processor 112 may sense additional motion within the second portion 532b of the streaking plate volume 532 while the user interacts with the tactile element and repeat steps, 664, 665, and/or 667, or proceed from step 663, to steps 617 and 612, as illustrated in FIG. 6A, at section line E-E, wherein the sensor 116 may detect motion in any of the volumes 532A, 532B, 534, 538, 540, and/or 542

Figure 6F:
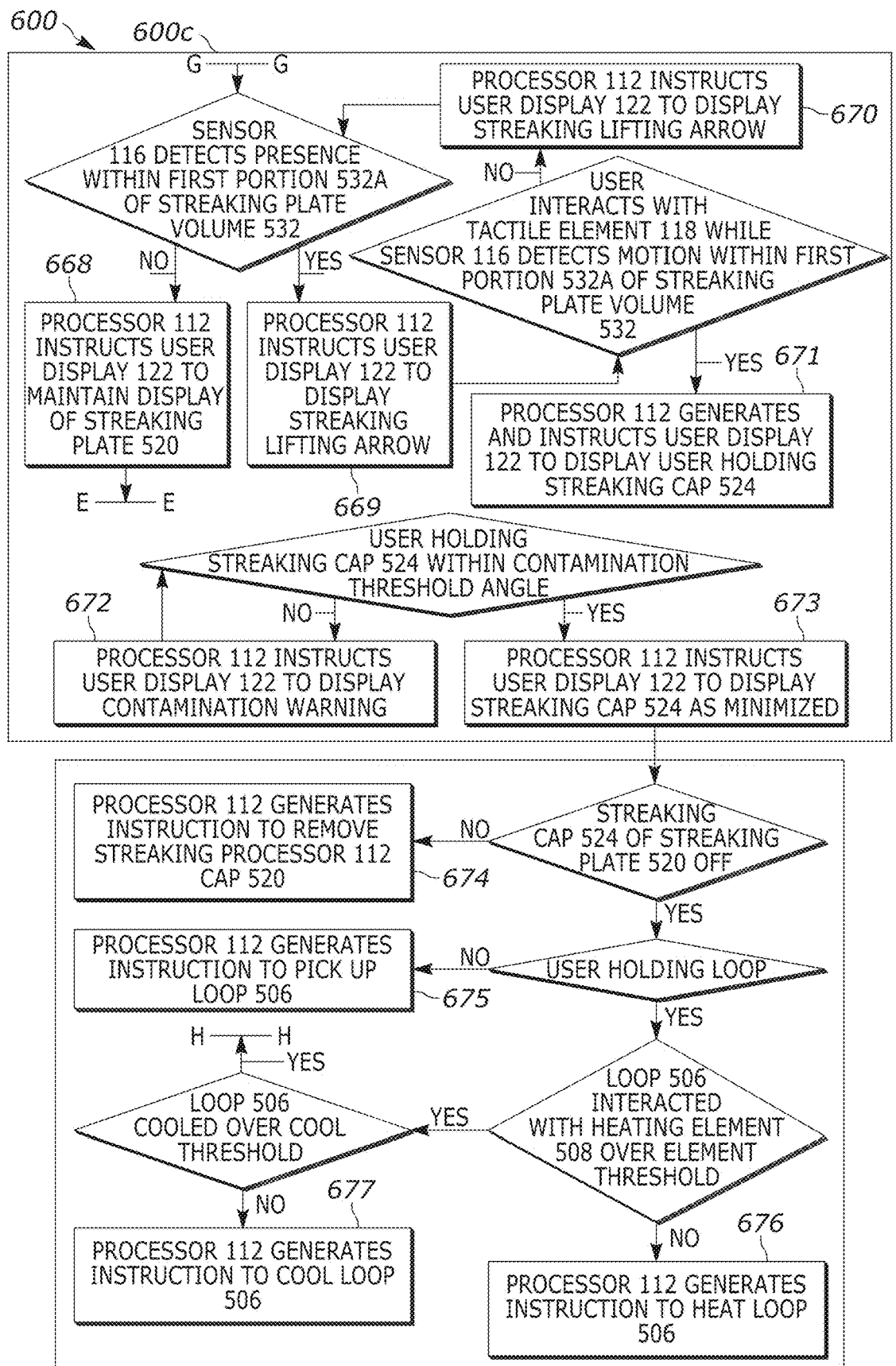
FIG. 6F is a schematic diagram of a method 600 of using a streaking plate cap removal process and a loop validation process in a selected streaking simulation generated by an example virtual reality system, according to one example embodiment of the present disclosure.

At 636, the sensor 116 detects motion in the first portion 532a of streaking plate volume 532 defined by the streaking plate 520 (FIG. 5E). As continued in example method 600 in FIG. 6F, at section line G-G, is a streaking plate cap removal process 600c. The streaking plate cap removal process 600c begins at 668, as illustrated. At 668, as illustrated in FIG. 6F, at section line G-G, absent the virtual reality system 100 receiving a signal that the user interacting with the tactile element 118 while the sensor 116 detects a presence of the controller 130 within the first portion 532a of the streaking plate volume 532, the processor 112 instructs the user display 122 to continue to display the streaking plate 520 (see FIG. 5C). At steps 617 and 612, as illustrated in FIG. 6A, at section line E-E, the processor 112 instructs the user display 122 to display the initial streaking view 530, and the sensor 116 may detect motion in any of the volumes 532A, 532B, 534, 538, 540, and/or 542 At 669, responsive to the virtual reality system 100 receiving a signal that the controller's 130 presence within the first portion 532a of the streaking plate volume 532, the processor 112 instruct the user display 122 to display the streaking lifting arrow 528 (see FIGS. 5F-5G).

At 670, responsive to the virtual reality system 100 receiving signal that the user is not interacting with the tactile element 118 and/or the sensor 116 is not detecting the presence of the controller 130 within the first portion 532a of the streaking plate volume 532, the processor 112 instruct the user display 122 to continue displaying the streaking lifting arrow 528 (see FIGS. 5F-5G). At 671, responsive to the virtual reality system 100 receiving a signal that the user is interacting with the tactile element 118 while the sensor 116 detects motion within the first portion 532a of the streaking plate volume 532, the processor 112 instruct the user display 122 to display the user icon 502b holding the streaking cap 524 (see FIG. 5P1). In one example embodiment, responsive to the virtual reality system 100 receiving a signal that the user is interacting with the tactile element 118 while the sensor 116 detects motion within the second portion 532b of the streaking plate volume 532, the processor 112 instruct the user display 122 to cease the display of the streaking lifting arrow 529. In the illustrated example embodiment of FIG. 5P1, the first user icon 502a is holding the loop 506 while the second user icon 502b is interacting with the streaking cap 524. It would be understood by one of ordinary skill in the art that the second user icon 502b may hold the loop 504, and/or the first user icon 502a could be interacting with the streaking cap 24, and further that one user icon need not be holding the loop for the streaking cap 54 to be removable.

At 672, responsive to the virtual reality system 100 receiving a signal that the user has moved the streaking cap 524 outside the contamination threshold angle 510a, the processor 122 instructs the user display 122 to display the contamination warning (e.g., text, visual, and/or audio) (see FIG. 5P1). Wherein, responsive to the streaking cap 524 being extended beyond the contamination threshold angle 510a, bacterial in the air may use gravity to land on the inside of said streaking cap 524, which will cause contamination within the streaking plate 520. At 673, responsive to the virtual reality system 100 receiving a signal that the user is maintaining the streaking cap 524 within the contamination threshold angle 510a, the processor 112 instructs the user display 122 to display the streaking cap 524 as minimized.

As continued in example method 600 in FIG. 6F, is a loop validation process 600d. The loop validation process 600d begins at 674, as illustrated. At 674, responsive to the processor 112 lacking a stored memory of the user icon 502 holding streaking cap 524, the processor generates an instruction to remove the streaking cap 524 (e.g., text, visual, and/or audio). In one example embodiment, the cap 510 being on the source plate 504 prevents access to the bacterial colony 504a, and no instruction is generated. At 675, responsive to the processor 112 lacking a stored memory of the user icon 502 holding the loop 504, the processor generates an instruction to pick of the loop (e.g., text, visual, and/or audio). In one example embodiment, the loop 504 remains stationary, and no instruction is generated. At 676, responsive to the processor 112 lacking a stored memory that the loop 504 has interacted with the heating element 508 over the heating element threshold (e.g., the loop has been assigned a bacteria count of 0), the processor generates an instruction to heat the loop (e.g., text, visual, and/or audio). In one example embodiment, no instruction is generated. At 677, responsive to the processor 112 lacking a stored memory that the loop 504 has cooled from interaction with the heating element 508 over the cool threshold, the processor generates an instruction to cool the loop (e.g., text, visual, and/or audio). In one example embodiment, nd instruction is generated. From 674, 675, 676, and 677, the method 600 continues to 617 by section line E-E in FIG. 6A, wherein the processor instructs the user display 122 to maintain the initial streaking view 530 (e.g., wherein the initial streaking view 530 includes past user inputs). At 612, the sensor 116 may detect motion in any of the volumes 532A, 532B, 534, 538, 540, and/or 532.

Figure 5Q:
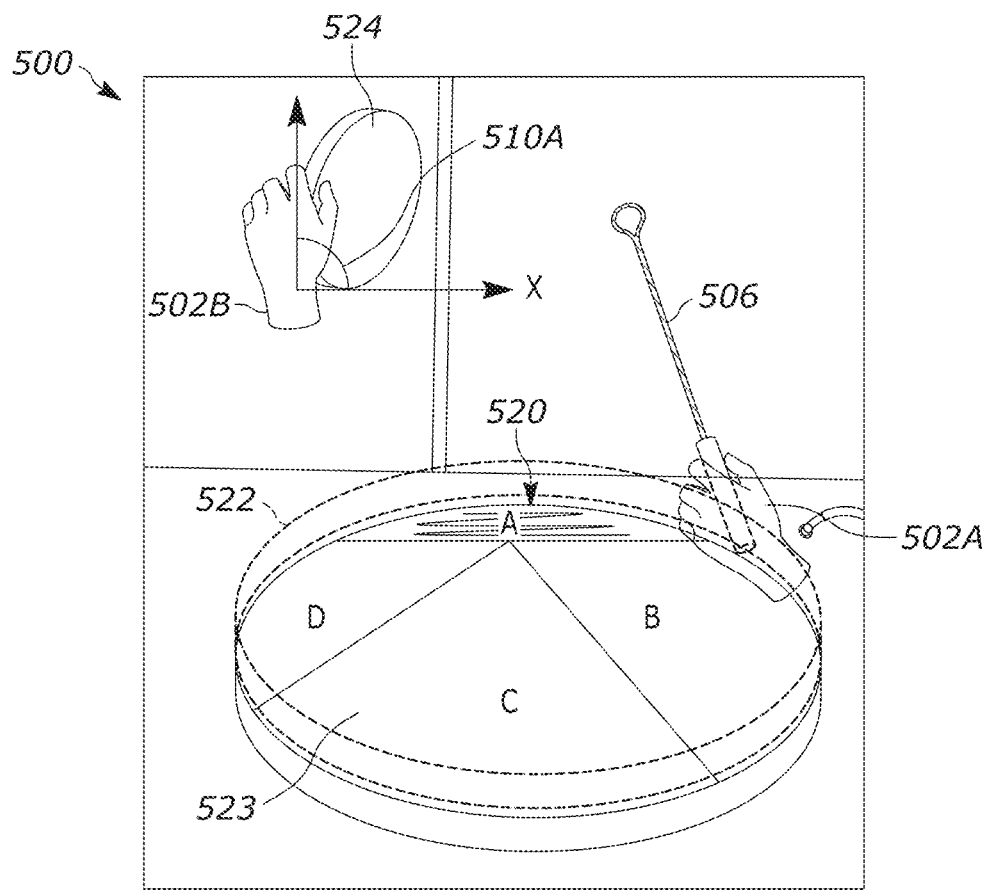
FIG. 5Q illustrates a streaking simulation including a loop interacting with a streaking plate having a streaking cap removed generated by an example virtual reality system, according to one example embodiment or the present disclosure.
Figure 5Q:
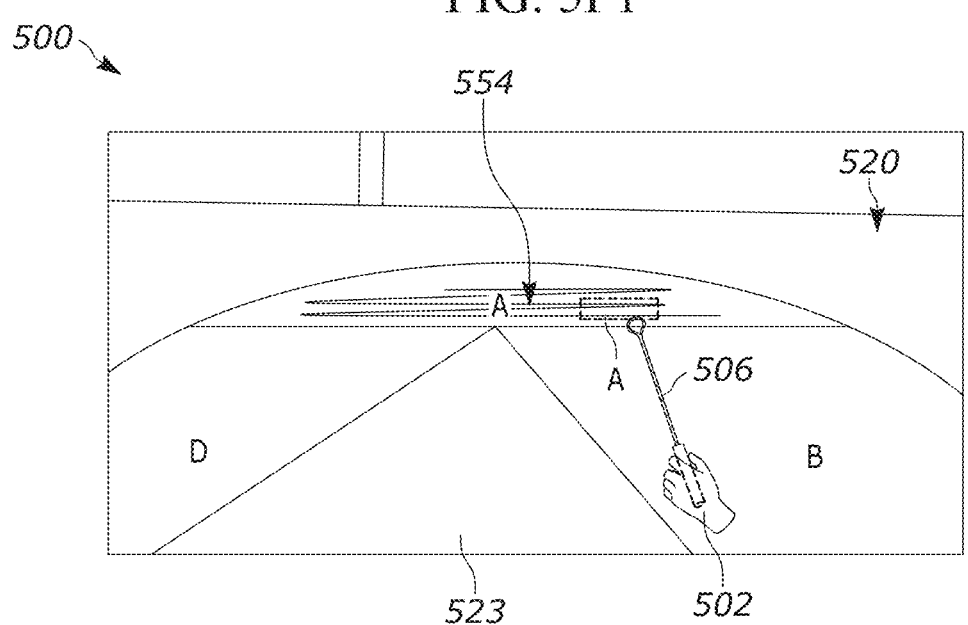
Figure 5R:
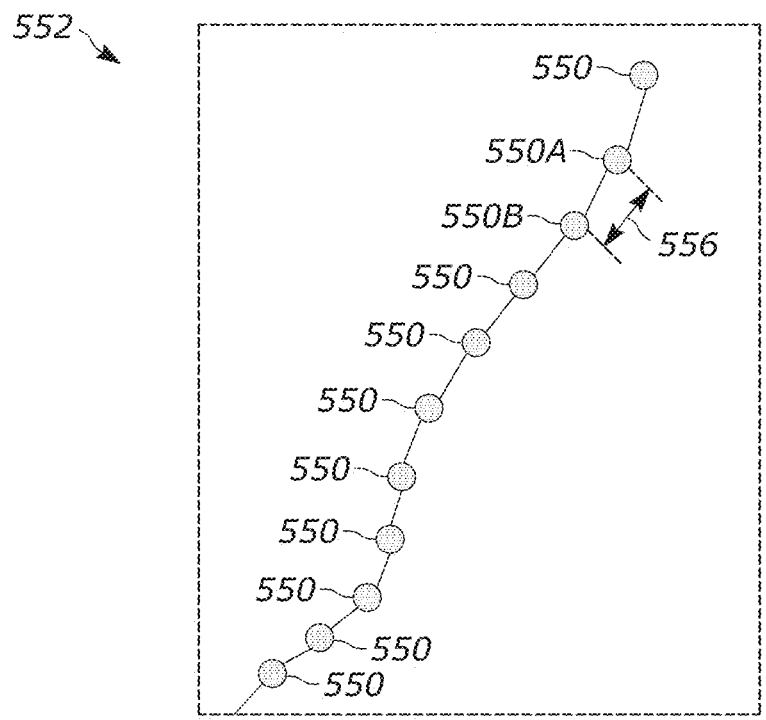
FIG. 5R illustrates a series of waypoints generated in a streaking simulation generated by an example virtual reality system, according to one example embodiment of the present disclosure.
Figure 6G:
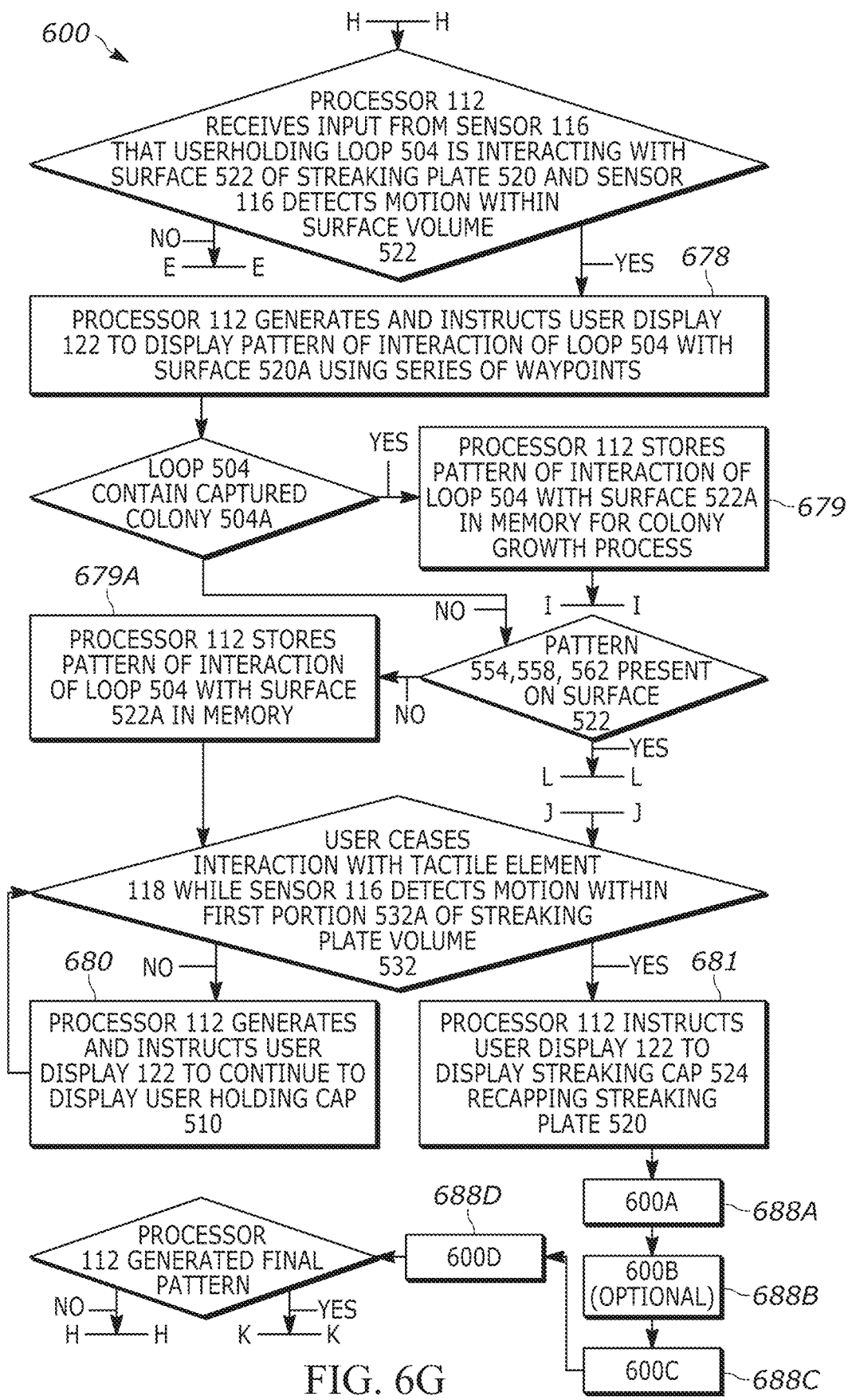
FIG. 6G is a schematic diagram of a method 600 of using a series of inputs to generate a series of way points in a selected streaking simulation generated by an example virtual reality system, according to one example embodiment of the present disclosure.

At 678, as illustrated in FIG. 6G, at section line H-H, responsive to the processor 112 having the stored memory of the user icon 502 holding the streaking cap 524, the user icon 502 holding the loop 504, the stored memory that the loop 504 has interacted with the heating element 508 over the heating element threshold, the stored memory that the loop 504 has cooled froth interaction with the heating element 508 over the cool threshold, and the sensor 116 detects motion within a surface volume 522 of the streaking plate 520, the processor 112 generates and instructs the user display 122 to display a line pattern 554 of interaction with loop 504 with a surface 523 of the streaking plate 520 using series of waypoints 550 (see FIG. 5R, 5Q). In an example embodiment, the processor 112 allows user interaction with the streaking plate 520 regardless of the presence of stored memory that the loop 504 has interacted with the heating element 508 over the heating element threshold, and/or the stored memory that the loop 504 has cooled from interaction with the heating element 508 over the cool threshold. Further, the processor 112 enables access to the top surface 523 of the streaking plate 520 that will support bacterial growth of the streaking plate 520 (see FIG. 5P1).

Absent the processer 112 having the stored memory of the user icon 502 holding the streaking cap 524, the processor 112 continues the method 600 to 617 by section line E-E in FIG. 6A, wherein the processor instructs the user display 122 to maintain the initial streaking view 536. At 612, the sensor 116 may detect motion in any of the volumes 532A, 532B, 534, 538, 540, and/or 542.

At 679*a*, responsive to the processor 112 not having a stored memory that the loop 504 contains a captured colony 504*a* and no pattern 554, 558, 562 is present on the surface 523 of the streaking plate 520, the processor 112 stores the pattern of interaction with the surface 523 in memory, and displays the pattern as it is being generated by the user input. At 679, responsive to the processor 112 having a stored memory that the loop 504 contains a captured colony 504*a*, the processor 112 stores a pattern of interaction with the surface 523 in memory for a colony growth process.

Figure 6H:
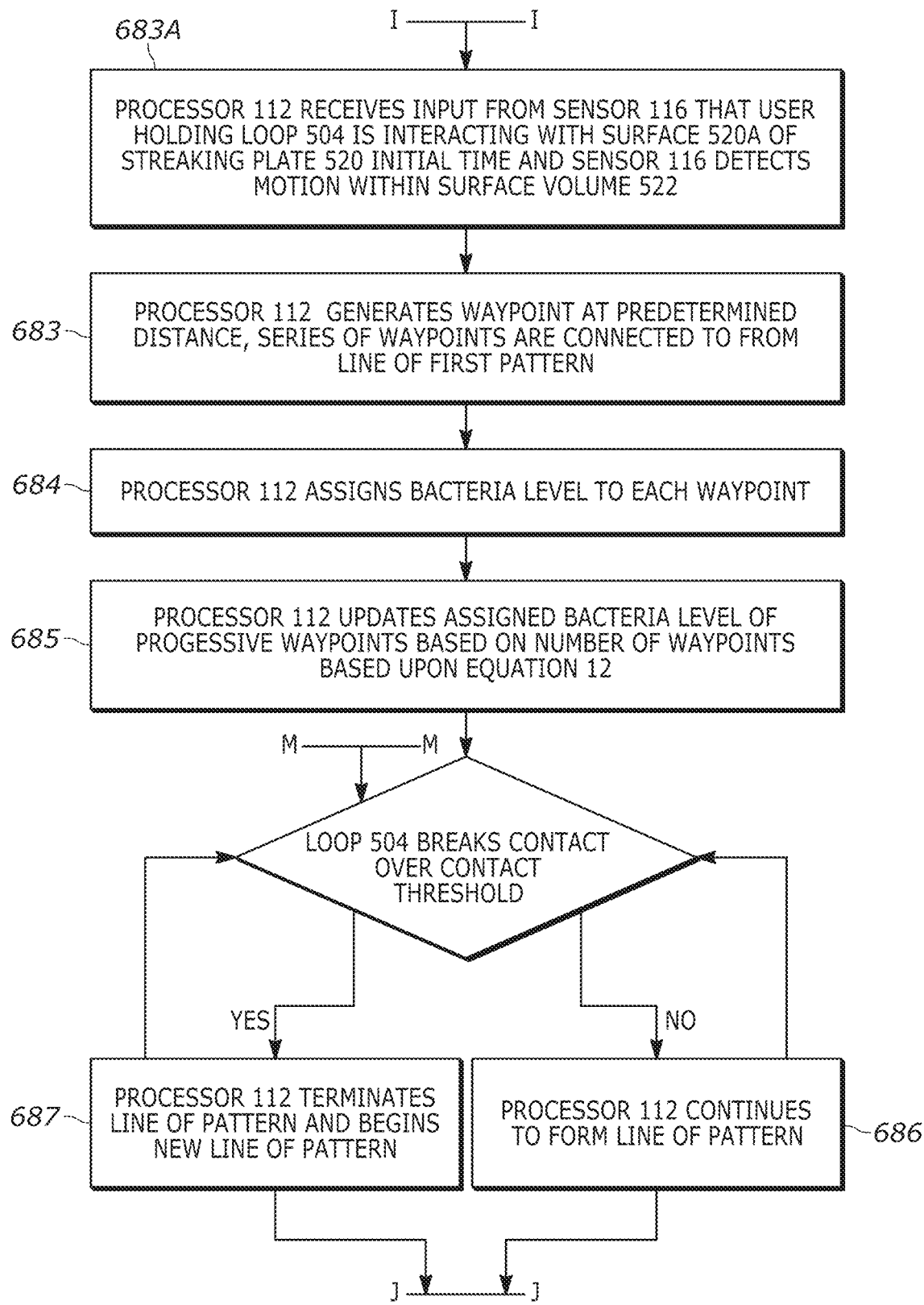
FIG. 6H is a schematic diagram of a method 600 of using a series of inputs to generate a pattern in a selected streaking simulation generated by an example virtual reality system, according to one example embodiment of the present disclosure.

Continued by section line I-I in FIG. 6H, at 683, the processor 112 receives an input form the sensor 116 that the user holding the loop 504 is interacting with the surface 523 of the streaking plate 520 an initial time (e.g., this is the first instance that the processor 112 has received input indicating interaction of the loop 504 having a bacteria colony 504*a* with the surface) and the sensor 116 detects motion within the surface volume 522.

At 683, the processor generates waypoints 550 at a predetermined generation distance 556, wherein a series of waypoints 552 are connected to form a first pattern 554 (see FIGS. 5Q-SS). At 684, the processor 112 assigns a bacterial level/concentration to each waypoint 550. In this example embodiment, the path of the loop 506 on the surface 523 of the streaking plate 520 is represented as the series of waypoints 552 connected to form a line. As illustrated in the example embodiment of FIG. 5R, an additional waypoint 550*a* is generated by the processor 112 responsive to the loop 504 moving a distance greater than predetermined generation distance 556 (e.g., 5 millimeters) from a previous waypoint 550*b*. If a waypoint 550 is a first waypoint of a pattern, the bacterial level or concentration on the loop 504 remains at the initial loop bacteria level value (e.g., 200). The sequential waypoints are connected together to form lines that form the first pattern 554.

At 685, the processor 112 updates assigned bacterial level/concentration of progressive waypoints 550, for example the assigned bacterial level is altered between waypoint 550*a* to waypoint 550*b*, based upon Equation 12, below. Responsive to a series of waypoints 552 being formed by connecting the previous waypoint 550*a* and the new waypoint 550*b* does not overlap any other pattern 554, 558, 562, 566 (see FIG. 5T), the bacteria level on the loop 504 is assigned to equal Concentration_n set by Equation 12:

$$\text{Concentration\_}n = \text{previousWaypointsConcentration} * 0.9975 \quad \text{EQUATION 12}$$

The initial concentration is 200 (200 is also the maximum concentration), wherein the concentration value of a second waypoint would equal 200 times the constant 0.9975. This progresses while additional waypoints 550 are being generated. When the processor 112 creates a waypoint 550, that waypoint is assigned a number of bacteria equal to the loop's 504 bacteria level (e.g., the loop's bacteria level is 200 after interacting with a bacteria colony 504*a* of the source plate 504). The processor 112 decreases the assigned bacteria concentration on the loop 504 as the pattern 554 is formed. In an actual laboratory setting, bacteria would strictly transfer from the loop 304, advantageously, modeling the distribution bacteria as described above, proves a more illustrative simulation of the real-world results of good and poor technique.

Figure 5S:
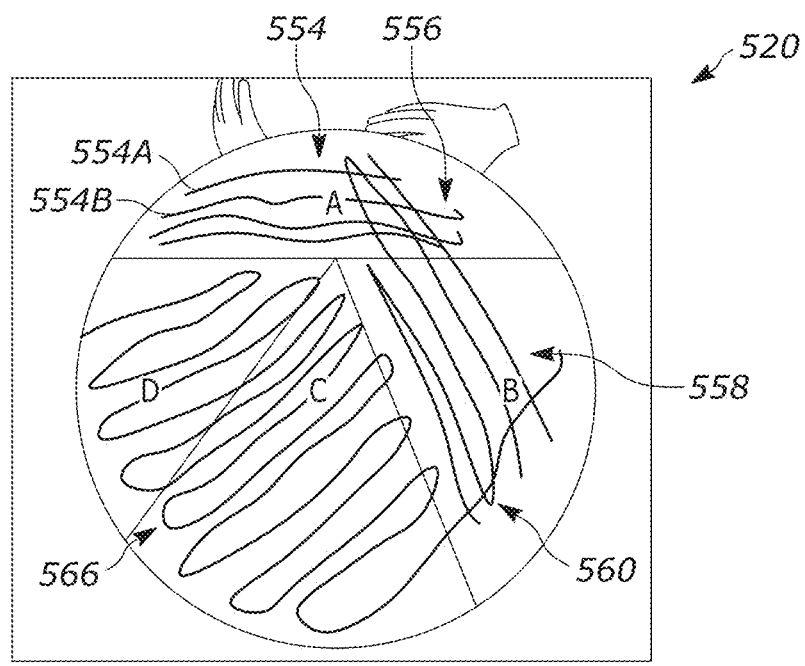
FIG. 5S illustrates a series of patterns of bacterial growth generated on a streaking plate generated in a streaking simulation generated by an example virtual reality system, according to one example embodiment or the present disclosure.

At 687, responsive to the sensor 116 indicating the loop 504 has broken contact with the surface 523 of the streaking plate 520 over a contact threshold, the processor 112 terminates an initial line 554*a* of pattern 554 and begins new line 554*b* of first pattern 554 (see FIG. 5S)(Note FIG. 5S illustrates bacterial growth, however the line 554 shape and terminations are the same whether bacteria is present or not). In one example embodiment, the contact threshold is 0.1 seconds. In another example embodiment, the contact threshold is between 0.005-1.0 seconds. At 686, responsive to the sensor 116 indicating the loop 504 has not broken contact with the surface 523 of the streaking plate 520 over the contact threshold, the processor 112 continues to form the line of first pattern 554 (see FIG. 5T).

Continued from section line J-J in FIG. 6H, illustrated in FIG. 6G as continuing from section line J-J or 679*a*, at 680, responsive to the processor 112 receiving a signal from the controller 130 that the user is continuing interaction with the tactile element 118 or the sensor 116 detects motion or presence within the first portion 532*a* volume of the streaking plate 520, the processor instructs the user display 122 to continue to display the streaking cap 524 being held by the user icon 502. At 681, responsive to the processor 112 receiving a signal from the controller 130 that the user ceased interaction with the tactile element 118 while the sensor 116 detects motion or the user presence within the first portion 532*a* volume of the streaking plate 520, the processor instructs the user display 122 to display the streaking cap 524 recapping the streaking plate 520.

At 688*a*, the processor 112 receives inputs from the loop sterilization process 600*a* illustrated in FIG. 6B. At 688*b*, the processor 112 receives optional inputs from the streaking plate rotation process 600*b* illustrated in FIG. 6E. At 688*c*, the processor 112 receives inputs from the streaking plate cap removal process 600*c* illustrated in FIG. 6F. In one example embodiment, the user icon 502 continues to hold the streaking cap 524. At 688*d*, the processor 112 receives inputs from the loop validation process 600*d* illustrated in FIG. 6F.

Continued from section line H-H in FIG. 6G, continuing in FIG. 6G, the processor 112 receives inputs from the sensor 116 generated at 678. Continued from section line L-L in FIG. 6G, continuing in FIG. 6I, at 689, responsive to the processor 112 having a stored memory that first/initial and/or intermediate patterns 554, 558, 562 are present on the surface 522 of the streaking plate 520, the processor 112 stores the pattern of interaction with the surface 523 in memory for colony growth process. At 690, the processor 112 receives input form the sensor 116 that the loop 504 is interacting with one or more lines of the first pattern 554 and/or intermediate patterns 558, 562. As described above with regard to Equation 12, the bacteria concentration assigned to the loop 504 will decrease as a line of the first pattern 554 is drawn. At 691, the processor 112 generates waypoints 550 at the predetermined distance, wherein the series of waypoints of the intermediate/second and/or third patterns 558, 562, and/or the final pattern 566 are connected to form a line. At 692, the processor 112 assigns a bacteria level to each waypoint based upon the interaction of the loop 504 with the one or more waypoints 550 of first, and/or intermediate patterns 554, 558, 562. Wherein, if the loop 504 crosses an existing pattern (e.g., first pattern 554, intermediate patterns 558, 562, and/or the final pattern 566), then the bacteria concentration assigned to the loop will be increased by an amount proportional to the difference between the assigned loop concentration at the most recently formed waypoint 550 and the waypoint of the existing pattern 558, 562, 566 nearest the overlap 556, 560, 564 of the existing pattern and the pattern being formed (see FIG. T). As illustrated in the example embodiment of FIG. 5T, wherein the patterns formed have been grown into a bacteria, a series of first overlaps 556 between the first pattern 554 and the second pattern 558, a series of second overlaps 560 between the second pattern 558 and the third pattern 562, and a series of third overlaps 564 between the third pattern 562 and the final pattern 566 are illustrated.

At 693, the processor 112 updates the assigned bacteria level of progressive waypoints 550 based on a number of overlaps of waypoints of first, and/or intermediate patterns 554, 558, 562 based upon Equations 13, 14, and/or 15, below. The bacterial concentration assigned to the loop 504 is based upon a pattern overlap, wherein the waypoint 550 in the existing pattern that is overlapped has an assigned bacterial concentration greater than the bacterial concentration assigned to the loop at the location of the overlap, The assigned bacteria concentration based upon said overlaps is calculated by Equations 13, 14, and 15 below.

$$\text{Concentration\_1} = \text{concentration\_}n + \text{beta} * (\text{overlappedSegmentsConcentration} - \text{concentration\_}n) * 0.00075 \quad \text{EQUATION 13}$$

$$\text{beta} = 2/(1 + e^{(\text{alpha} * (1-r))}) - 1 \quad \text{EQUATION 14}$$

$$r = \text{overlappedSegmentsConcentration} / \text{concentration\_}n \quad \text{EQUATION 15}$$

If the concentration_1 is zero, then r is equal to 10. Concentration_0 is equal to the concentration or bacteria level assigned to the loop 504 at the location of the overlap, as calculated by Equation 12 above. Alpha is a constant used in the fuzzy math formula presented in Equation 14. Alpha is a constant greater than zero.

Figure 6I:
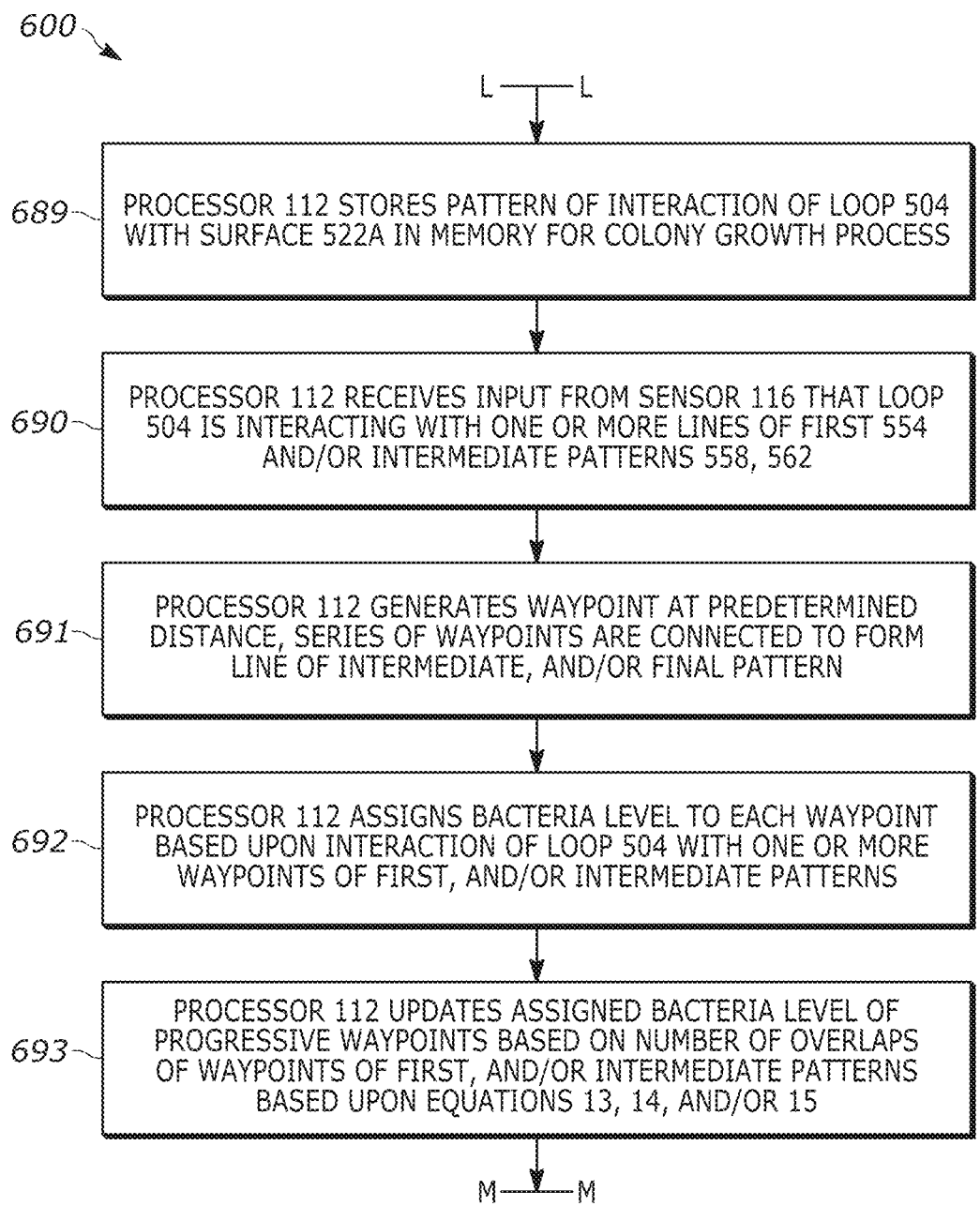
FIG. 6I is a schematic diagram of a method 600 of using a series of inputs to generate a pattern based upon existing pattern interactions in a selected streaking simulation generated by an example virtual reality system, according to one example embodiment of the present disclosure.

Continued from section line M-M in FIG. 6I, continuing at section line M-M in FIG. 6H, steps 686 and 687 are repeated to generate the pattern (e.g., with or without broken lines). Continued from section line J-J in FIG. 6H, continuing at section line J-J in FIG. 6G, at 680, responsive to the processor 112 receiving the signal from the controller 130 that the user is continuing interaction with the tactile element 118 or the sensor 116 detects motion or the user presence within the first portion 532*a* volume of the streaking plate 520, the processor instructs the user display 122 to continue to display the streaking cap 524 being held by the user icon 502. At 681, responsive to the processor 112 receiving a signal from the controller 130 that the user ceased interaction with the tactile element 118 while the sensor 116 detects motion or the user presence within the first portion 532*a* volume of the streaking plate 520, the processor instructs the user display 122 to display the streaking cap 524 recapping the streaking plate 520. At 688*a*, the processor 112 receives inputs from the loop sterilization process 600*a* illustrated in FIG. 6B. At 688*b*, the processor 112 receives optional inputs from the streaking plate rotation process 600*b* illustrated in FIG. 6E. At 688*c*, the processor 112 receives inputs from the streaking cap removal process 600*c* illustrated in FIG. 6F. At 688*d*, the processor 112 receives inputs from the loop validation process 600*d* illustrated in FIG. 6F.

Figure 5T:
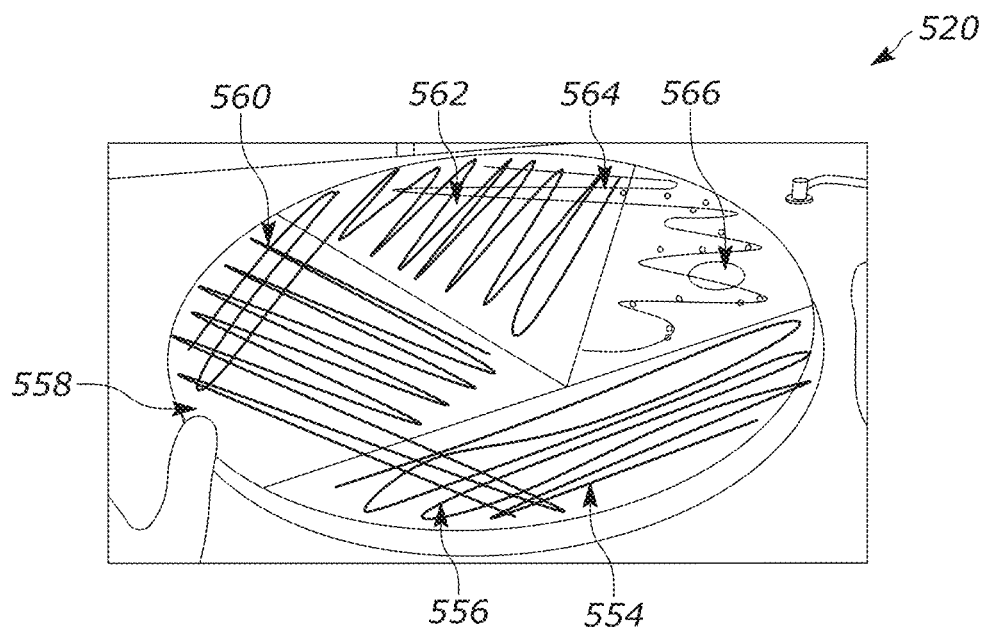
FIG. 5T illustrates a second series of patterns of bacterial growth generated on a streaking plate generated in a streaking simulation generated by an example virtual reality system, according to one example embodiment of the present disclosure.
Figure 5U:
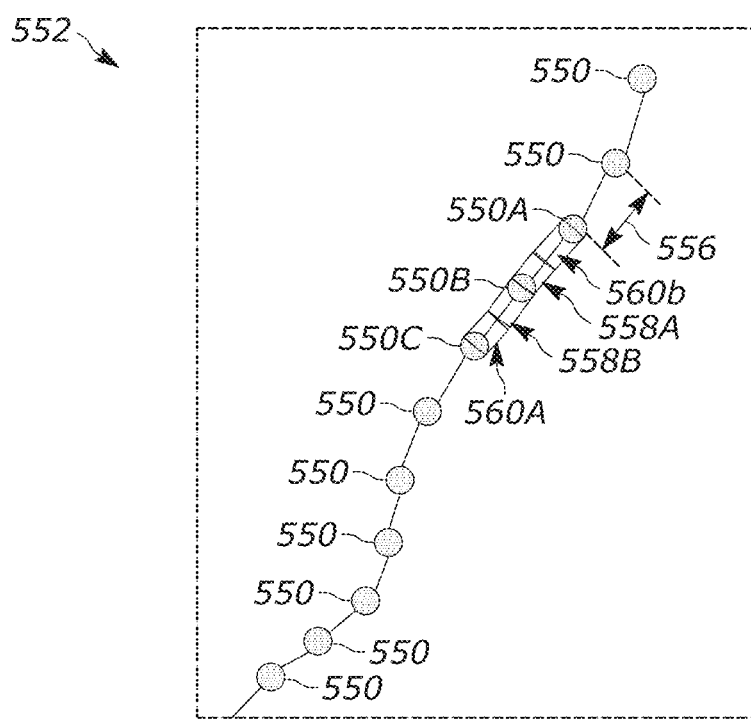
FIG. 5U illustrates a series of waypoints and corresponding rectangles generated in a streaking simulation generated by an example virtual reality system, according to one example embodiment of the present disclosure.
Figure 6J:
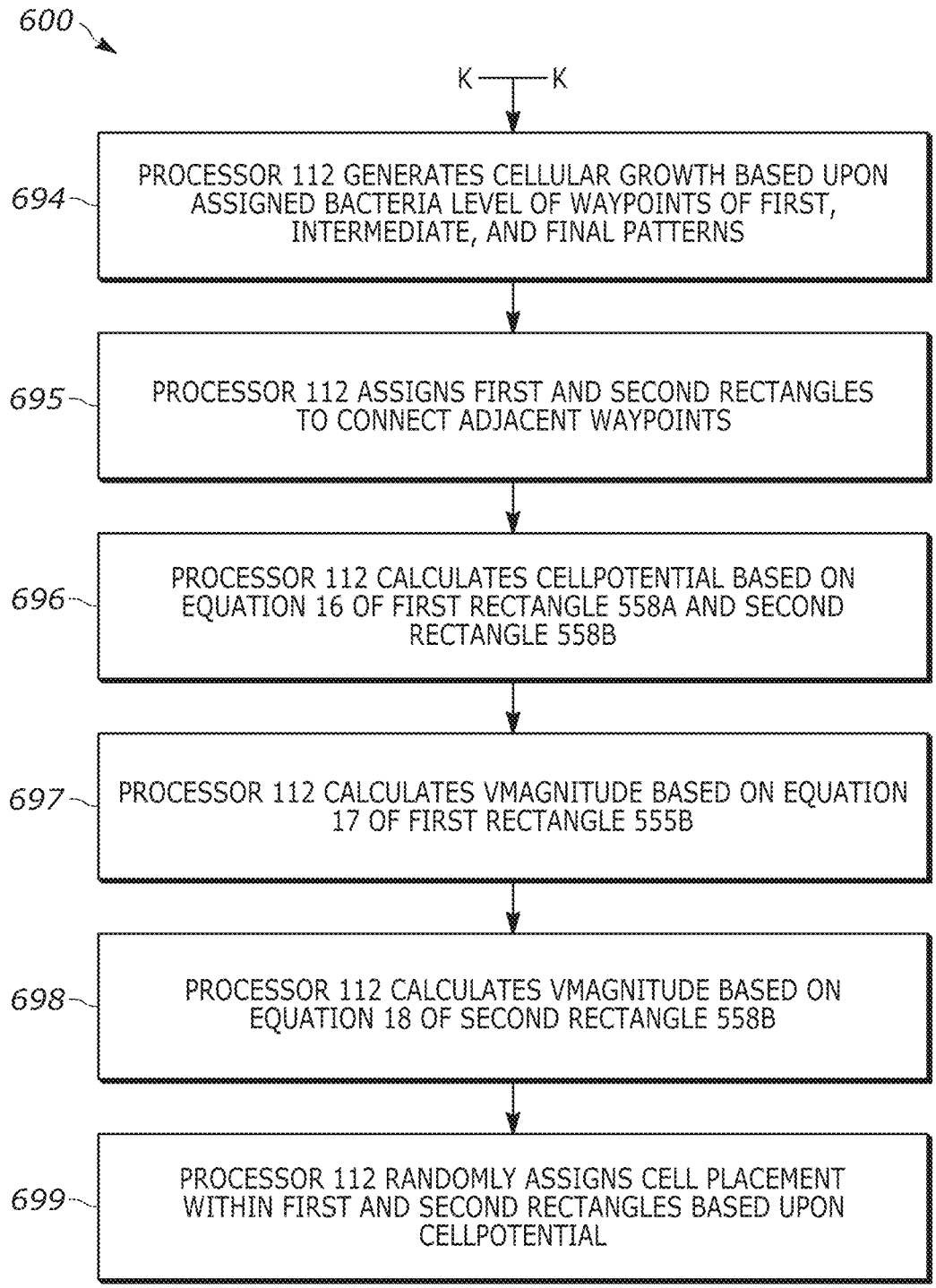
FIG. 6J is a schematic diagram of a method 600 of calculating bacterial growth based upon the pattern generated based upon a series of inputs based upon existing pattern interactions in a selected streaking simulation generated by an example virtual reality system, according to one example embodiment of the present disclosure.

Continued from section line K-K in FIG. 6G, continuing at section line K-K in FIG. 6J, responsive to the processor 112 having a stored memory that the final pattern 566 is present on the surface 523 of the streaking plate 520, the processor 112 generates cellular growth based upon the Assigned concentrations/bacteria levels of the waypoints 550 of the first, intermediate, and final pattern 554, 58, 362, 566 (see FIG. 5T). It would be appreciated by one having ordinary skill in the art that in one example embodiment, the final pattern 566 may be any pattern that extends into the fourth quadrant 520*d* (see, for example, FIG. 5S), wherein the first pattern may also comprise the final pattern responsive the pattern initiating in the first quadrant 520*a* and ending in the fourth quadrant 520*d*. In another example embodiment, the first pattern 554 is any pattern generated during the first streaking cap 524 removal and replacement, wherein after loop sterilization, the second pattern 558 is any pattern generated during a second streaking cap 524 removal and replacement, etc.

At 695, the processor 112 assigns first and second rectangles 558*a*, 558*b* (see FIG. 5U) to connect adjacent waypoints 550*a*, 550*b*, 550*c*. For each waypoint 550 on a line of a pattern 554, 558, 562, 566, two rectangles 558*a*, 558*b* are calculated. The first rectangle 558*a* extends from the waypoint 550*b* to halfway to a previous waypoint 550*c*. The second rectangle 588*b* extends from the waypoint 550*b* to halfway to a next waypoint 550*a*. Thus, as shown in the illustrated example embodiment of FIG. 5U, the first rectangle 558*a* of the waypoint 550*b* connects to a second rectangle 560*b* of the next waypoint 550*a*, and the second rectangle 558*b* of the waypoint 550*b* connects to a first rectangle 560*a* of the previous waypoint 550*c*, until an area is defined based upon the waypoints 550.

At 696, the processor 112 calculates the cell potential, based upon Equation 16 below, of the first rectangle 558*a* and the second rectangle 558*b* of the waypoints 550.

$$\text{cellPotential} = \text{waypointConcentration} * 330 * \text{vMagnitude}/0.005 \quad \text{Equation 16}$$

At 697, the vMagnitude for the first rectangle 558*a* is calculated using Equation 17, below. At 698, the vMagnitude for the second rectangle 558*b* is calculated using Equation 18, below. Wherein, in Equation 16, 330 and 0.005 are constants, and the waypointConcentration is the concentration of the waypoint 550*b*, wherein the waypointConcentration is the individual Concentration_n assigned to each waypoint 550 based upon Equation 12, above.

$$v\text{Magnitude} = \text{Magnitude}(\text{currentWaypointPosition} - \text{previousWaypointPosition}) \quad \text{Equation 17}$$

$$v\text{Magnitude} = \text{Magnitude}(\text{currentWaypointPosition} - \text{nextWaypointPosition}) \quad \text{Equation 18}$$

The Magnitude in Equations 17 and 18 is the Euclidian distance of a three-dimensional vector with components x,y,z, defined as $\text{sqrt}(x^2 + y^2 + z^2)$. As illustrated in the example embodiment of FIG. 5U, the currentWaypointPosition in both Equations 17 and 18, is the location of the waypoint 550*b* expressed as a three-dimensional vector relative to the coordinate system of the streaking plate 520. The previousWaypointPosition in Equation 17, is the location of the previous waypoint 550*c* expressed as a three-dimensional vector relative to the coordinate system of the streaking plate 520. The nextWaypointPosition in Equation 17, is the location of the next waypoint 550*a* expressed as a three-dimensional vector relative to the coordinate system of the streaking plate 520. In one example embodiment, steps 696-698 may occur in any order, or simultaneously. In another example embodiment, steps 697 and 698 occur before step 696.

At 699, the processor randomly assigns cell placement within the first and second rectangles 558a, 558b based upon the calculated cellPotential. Stated another way, a number of cells loosely based upon the concentration of the waypoint 550b are randomly placed within each rectangle 558. The higher the concentration, the more cells that are likely to be placed. If the cellPotential is greater than 20, it is capped at 20. After the cellPotential has been calculated, a random value between 0 and 1 is selected. If the value is less than the cellPotential, a cell is placed at a random location within the respective rectangle 558. Regardless of whether or not a cell was placed, cellPotential is decremented by 1.0. While cellPotential is greater than or equal to 0, the above steps of generating a random number, potentially placing a cell, and decrementing by 1.0 are repeated. The assignment of cells correlates to bacterial growth in the real world. In the real world, the streaking plate 520 must be left to grow for 12-24 hours, at a temperature conducive to bacterial growth, thus the user does not know if they have successfully isolated a bacterial colony until the 12-14 hours has passed. Here, the processor 112 may assign a growth time (e.g., the time it takes for colonies to fully grow) that is much shorter than the real-world growth time. In one example embodiment, the growth time is 1 sec to about 4 minutes. In another example embodiment, the growth time is 10 seconds.

As illustrated in FIG. 5T, an incubation and growth visualization is illustrated, wherein the first, intermediate and final patterns 554, 558, 562, 566 are converted into bacterial growth, wherein the first pattern 554 is within the first quadrant 520a, the second/intermediate pattern 558 is within the second quadrant 520b, the third/intermediate pattern 562 is within the third quadrant 520c, and the final pattern 566 is within the fourth quadrant 520d. For example, in order to transfer bacteria in the fourth quadrant 520d, the average of all waypoints 550 associated with the fourth quadrant 520d must be between 0.00001 and 0.0005. Every line of a pattern that is created is assigned to a quadrant 520a-520d. The quadrant 520a-520d assigned is not based on the waypoint's 550 physical location, rather the quadrant is assigned to whatever is specified as the "active quadrant" as assigned by the processor 112. During the formation of the initial/first pattern 554, the active quadrant is the first quadrant 520a. The active quadrant remains as the first quadrant 520a until at least one line is created and then the loop 504 has interacted with the heating element 508 (see method step 698a including inputs generated from the loop sterilization process 600a illustrated in FIG. 6B) and/or the streaking cap 524 has been positioned back on the streaking plate 504 (see method step 688c, including inputs from the streaking plate cap removal process 600c illustrated in FIG. 6F.). The processor 112 will update the active quadrant to the second/intermediate quadrant 520b. The processor 112 will continue to update the active quadrant until the active quadrant is the final quadrant 520d. The user is not limited by the processor 112 to the active quadrant and provide inputs across all the quadrants 520a-520d. The processor 112 calculates an outcome of the bacterial growth. The outcome is compared to a threshold, wherein the results (e.g., passing and over the threshold, failing and under the threshold) are provided to an output, including a visual display (e.g., user display 122), test data bank, etc.

Figure 6K:
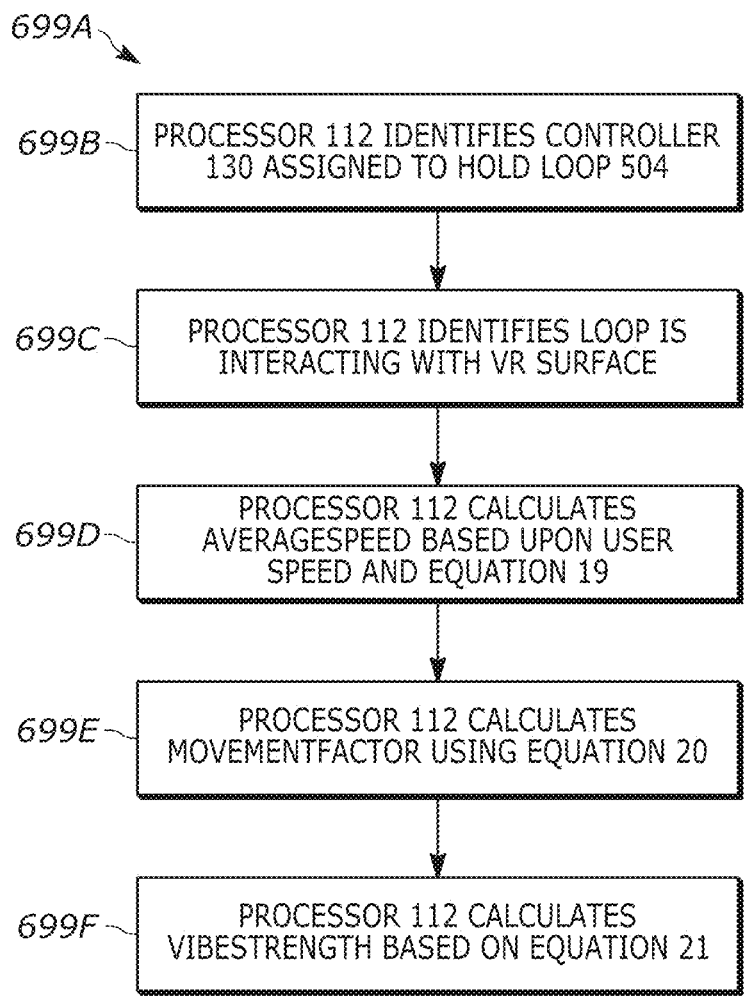
FIG. 6K is a schematic diagram of a method 699*a* of calculating haptic feedback based upon a series of inputs in a selected streaking simulation generated by an example virtual reality system, according to one example embodiment of the present disclosure.

As illustrated in the example embodiment of FIG. 6K, a method 699a of haptic feedback is illustrated. At 699b, the processor 112 identifies controller 130 assigned to hold loop 504 (e.g. based upon inputs received by the processor at steps 612, 616 in method 600 illustrated in FIG. 6A). At 699c, the processor 112 identifies that the loop 504 is interacting with a VR generated surface (e.g., the top surface 505 of the source plate 504 based upon inputs received by the processor at steps 630, 660 in method 600 illustrated in FIGS. 6A and 6D, respectively, and/or the surface 523 of the streaking plate 520 based upon inputs received by the processor at step 679 in method 600 illustrated in FIG. 6G). At 699d, the processor 112 calculates an average speed based upon a speed of the controller 130 assigned to hold the loop 504 and Equation 19, below.

$$averageSpeed = instantaneousSpeed * exponentialAverageCoefficientAlpha + averageSpeed\_0 * (1 - exponentialAverageCoefficientAlpha)$$

Equation 19

Wherein, the exponentialAverageCoefficientAlpha is a unitless constant assigned a value of 0.7, the instantaneousSpeed is the speed at which the user is moving the controller 130 in m/sec. The averageSpeed_0 The averageSpeed_0 is the result of the previous calculation of equation 19. If equation 19 has not been previously calculated, averageSpeed_0 starts with a value of 0. At 699e, the processor 112 calculates an movementFactor based upon the calculated averageSpeed and Equation 20, below.

$$movementFactor = averageSpeed/0.02$$

Equation 20

At 699f, the processor 112 calculates an vibestrength based upon the calculated movementFactor and Equation 21, below.

$$vibeStrength = baseStrength * movementFactor$$

Equation 21

Wherein, basestrength is a constant assigned a value of 1. The larger the vibeStrength the greater an intensity of the vibration of the designated controller 130. The haptic experience of using the loop 504 by modulating the vibration of the controller 130 increases the real feel of the virtual world. Stated simply, as the loop 504 is moved at increasing speeds across h surface, the processor 112 increases the intensity of the vibration.

Simulating and visualizing a transfer of bacteria from source colony 504 to streaking plate 520, such that poor technique results in too many or too few colonies allows for rapid and illustrative training. Advantageously, the processor 112 instructs that the streaking plate 502 be displayed on the user display 122 as oversized so that imprecision is easily visualized, while any lack of dexterity or fine motor skills with the controller 130 are minimized by the size of the streaking plate. Further, the processor 112 instructs the user display 122 to display the streaking plate 520 presenting bacterial growth results that are more visible by: a) increasing the bacteria count on portions of lines or patterns 554, 558, 562, and/or 566 that cross previous lines or patters; b) by decreasing the bacteria on the loop 504 as it is moved over the surface 523 of the streaking plate; c) by adding bacteria to the loop 504 responsive to the loop having successfully up taken a colony 504a, d) by assigning a bacteria concentration of 0 if the loop 504 successfully undergoes the loop sterilization process 600a, e) by creating visual indications of the concentration of bacteria in each pattern 554, 558, 562, and/or 566 so that proper technique results in separated/isolated colonies, and/or f) by speeding the incubation process of the bacteria so that results can be seen in a few seconds rather than 3-5 days. Further, the processor 112 instructs the controller 130 to provide haptic feedback to facilitate use of the streaking simulation 500.

Visual Inspection Simulation 700

Figure 7A:
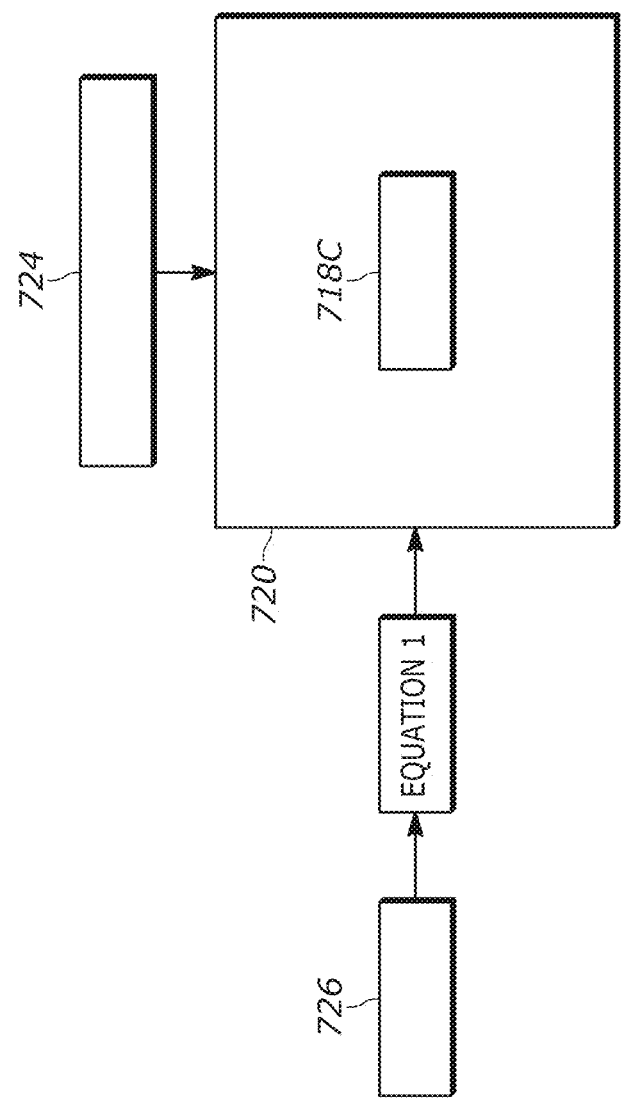
FIG. 7A illustrates a schematic view of inputs used in a visual inspection simulation generated by an example virtual reality system, according to one example embodiment of the present disclosure.
Figure 7B:
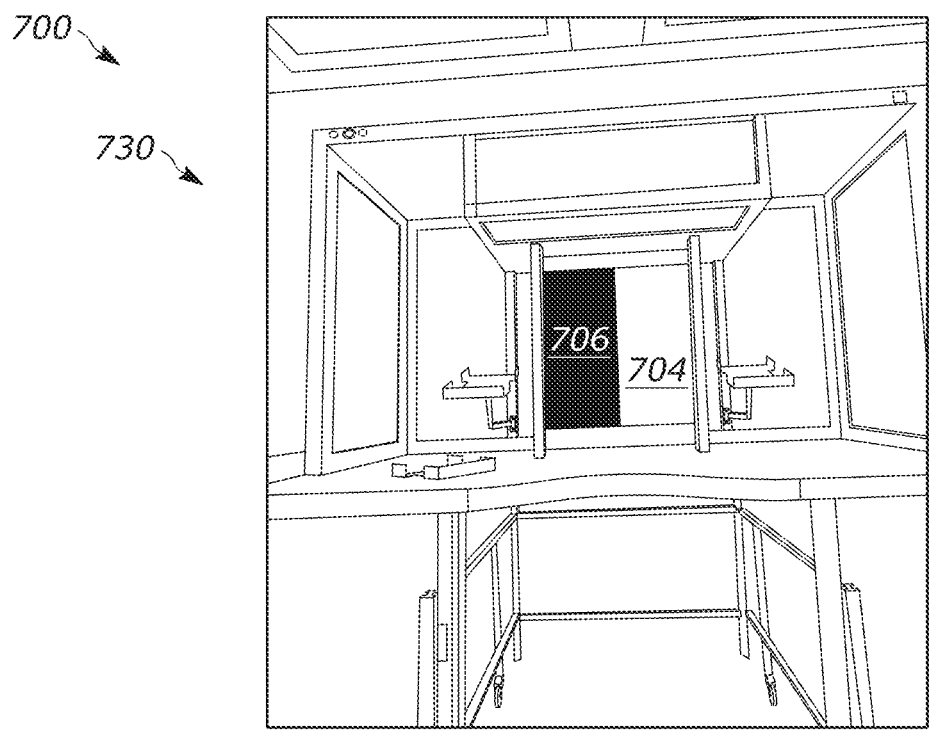
FIG. 7B illustrates a visual inspection simulation generated by an example virtual reality system, according to one example embodiment of the present disclosure.
Figure 7C:
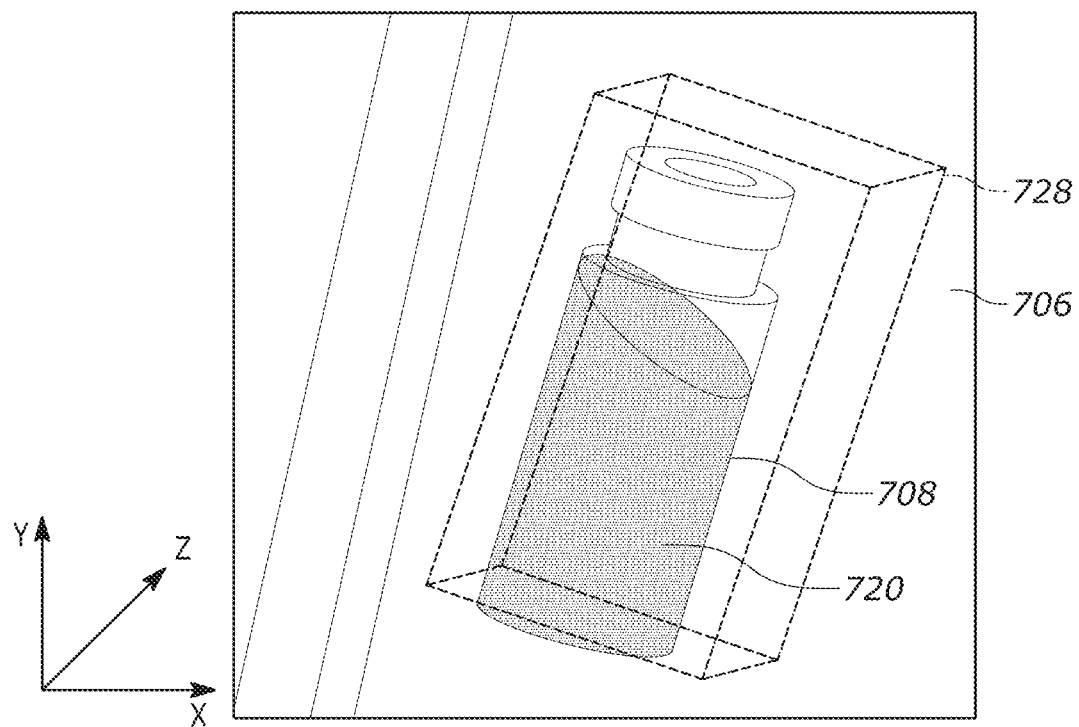
FIG. 7C illustrates a container generated in a visual inspection simulation generated by an example virtual reality system, according to one example embodiment of the present disclosure.
Figure 7D:
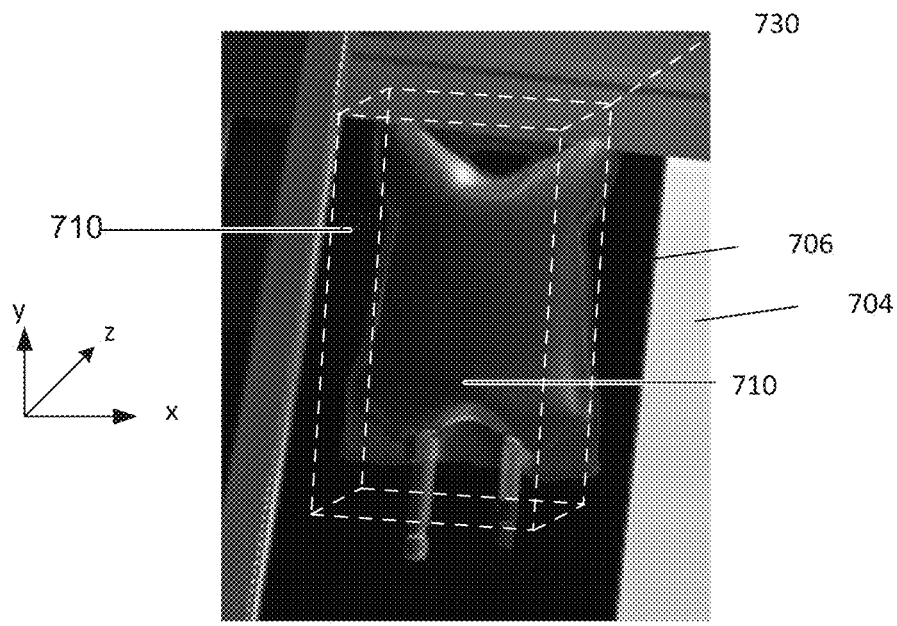
FIG. 7D illustrates a container generated in a visual inspection simulation generated by an example virtual reality system, according to another example embodiment of the present disclosure.
Figure 7E:
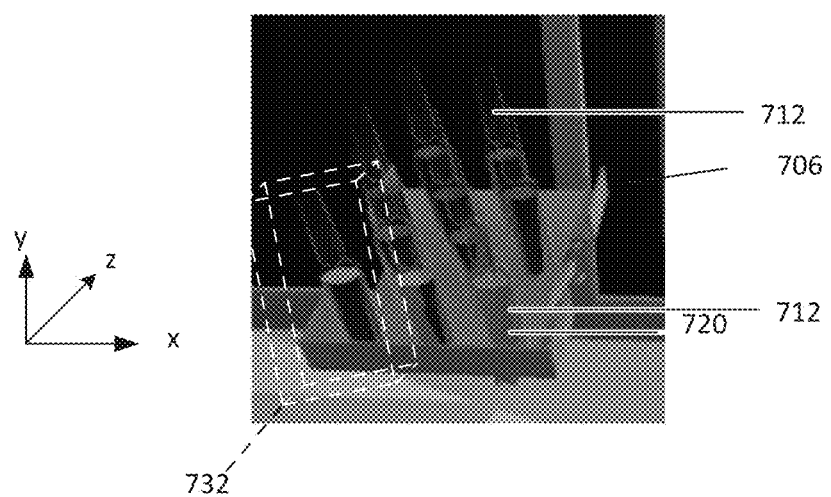
FIG. 7E illustrates a container generated in a visual inspection simulation generated by an example virtual reality system, according to yet another example embodiment of the present disclosure.
Figure 7F:
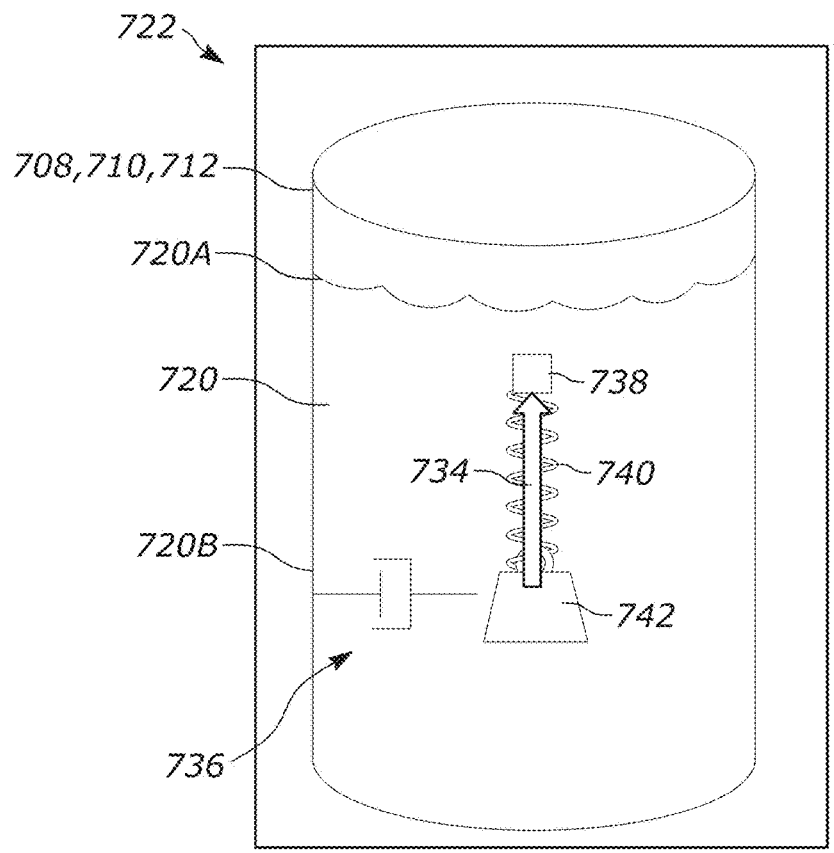
FIG. 7F illustrates a liquid mass model that is used as an input in a visual inspection simulation generated by an example virtual reality system, according to yet another example embodiment of the present disclosure.
Figure 7G:
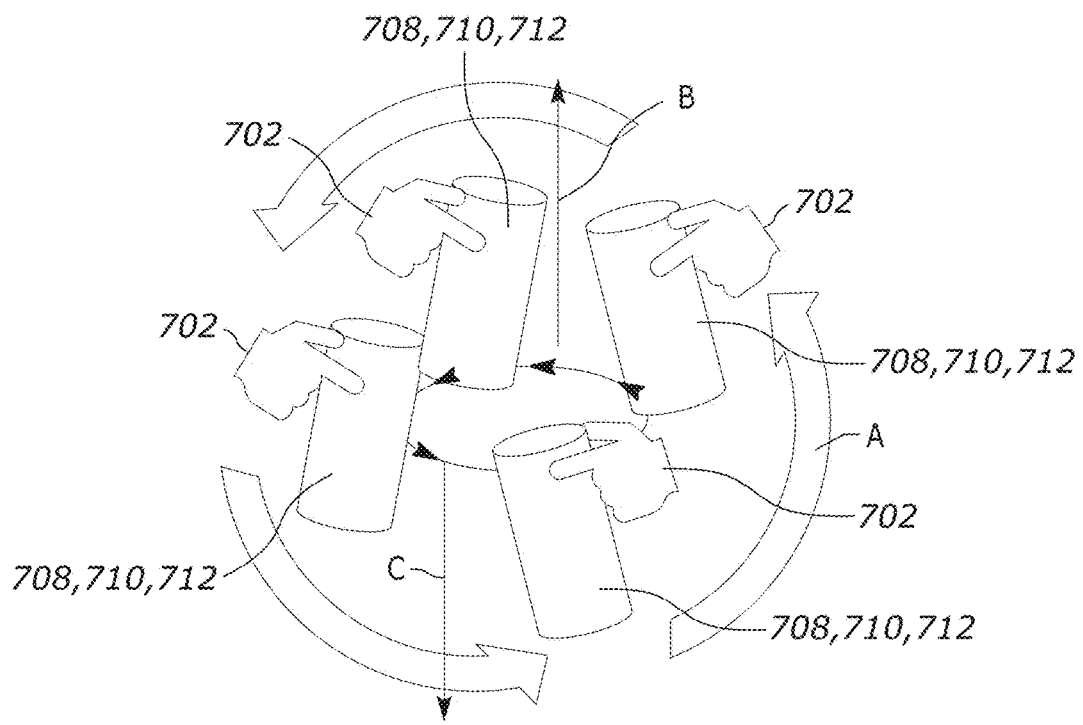
FIG. 7G illustrates a schematic-view of a container rotation motion generated in a visual inspection simulation generated by an example virtual reality system, according to yet another example embodiment of the present disclosure.
Figure 7H:
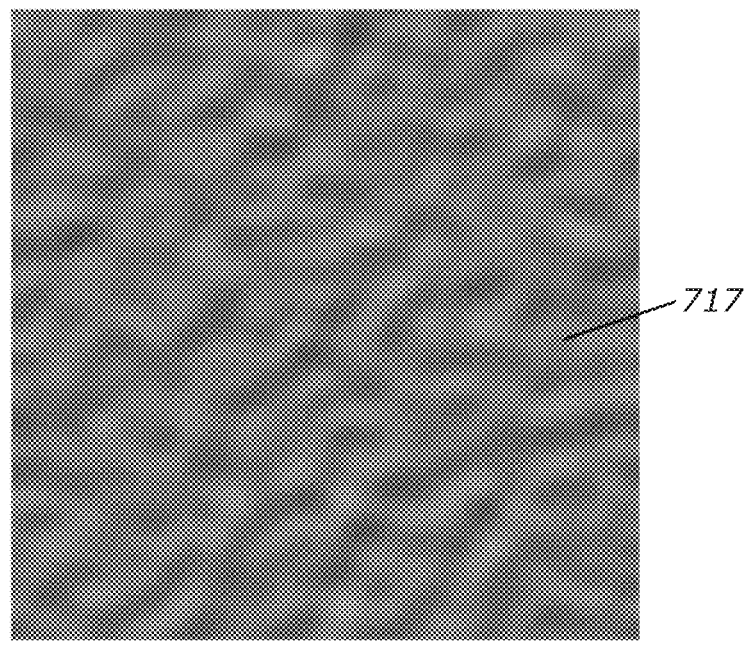
FIG. 7H illustrates a 2 dimensional (2D) surface used in a visual inspection simulation generated by an example virtual reality system, according to yet another example embodiment of the present disclosure.
Figure 7I:
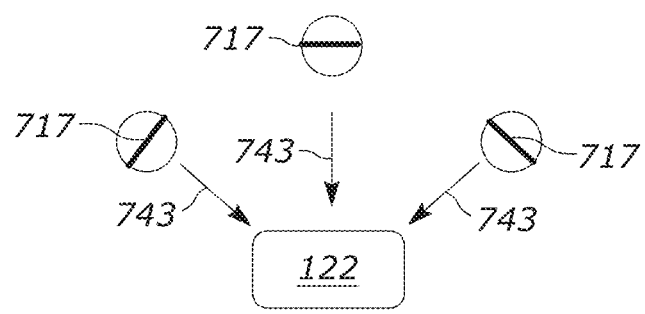
FIG. 7I illustrates an assigned orientation of a 2 dimensional (2D) surface relative to a user display used in a visual inspection simulation generated by an example virtual reality system, according to yet another example embodiment of the present disclosure.
Figure 7J:
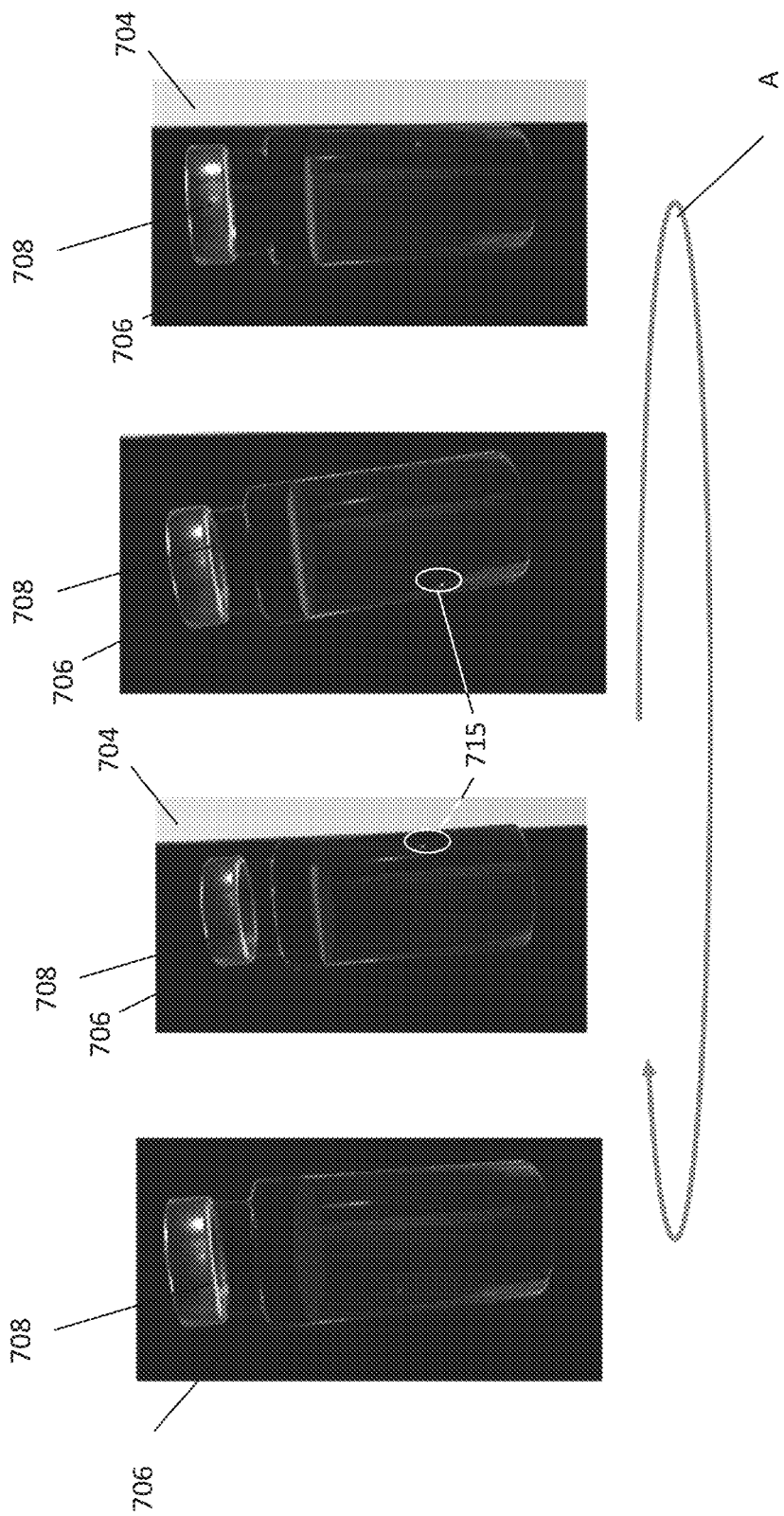
FIG. 7J illustrates a container that has been assigned shards generated in a visual inspection simulation generated by an example virtual reality system, according to yet another example embodiment of the present disclosure.
Figure 7L:
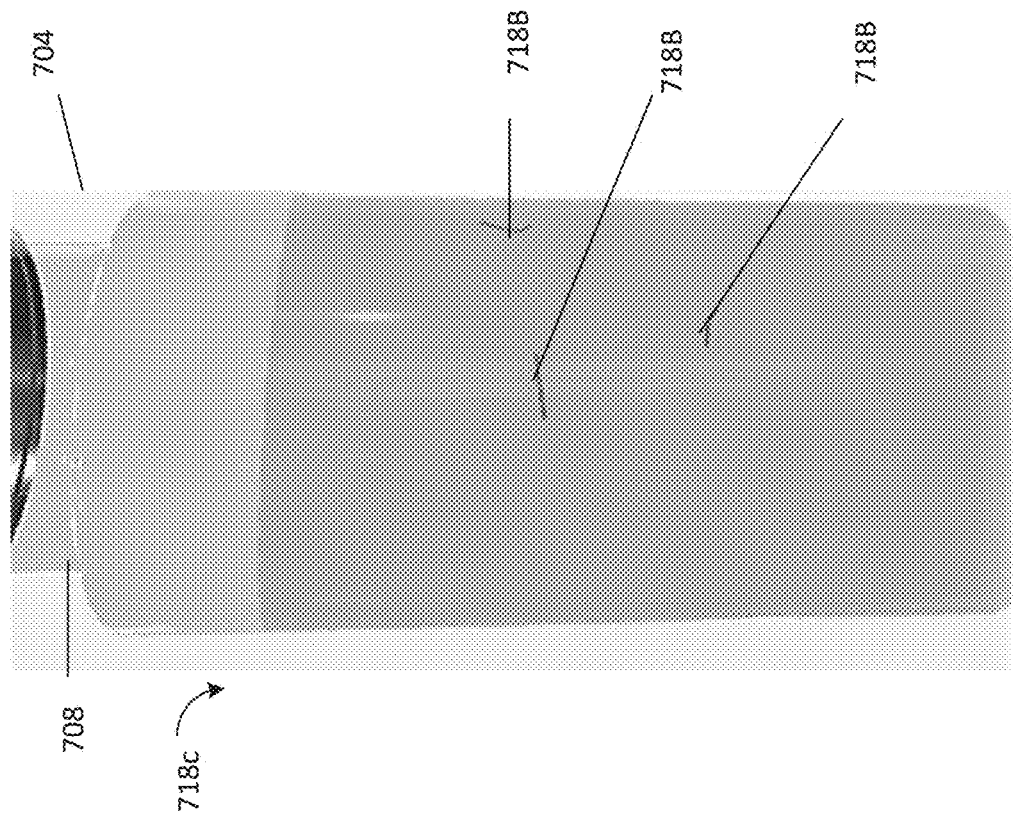
FIG. 7L illustrates a container having fibers assigned to be second visual indicator fibers illustrated as in front of a first background generated in a visual inspection simulation generated by an example virtual reality system, according to yet another example embodiment of the present disclosure.
Figure 7K:
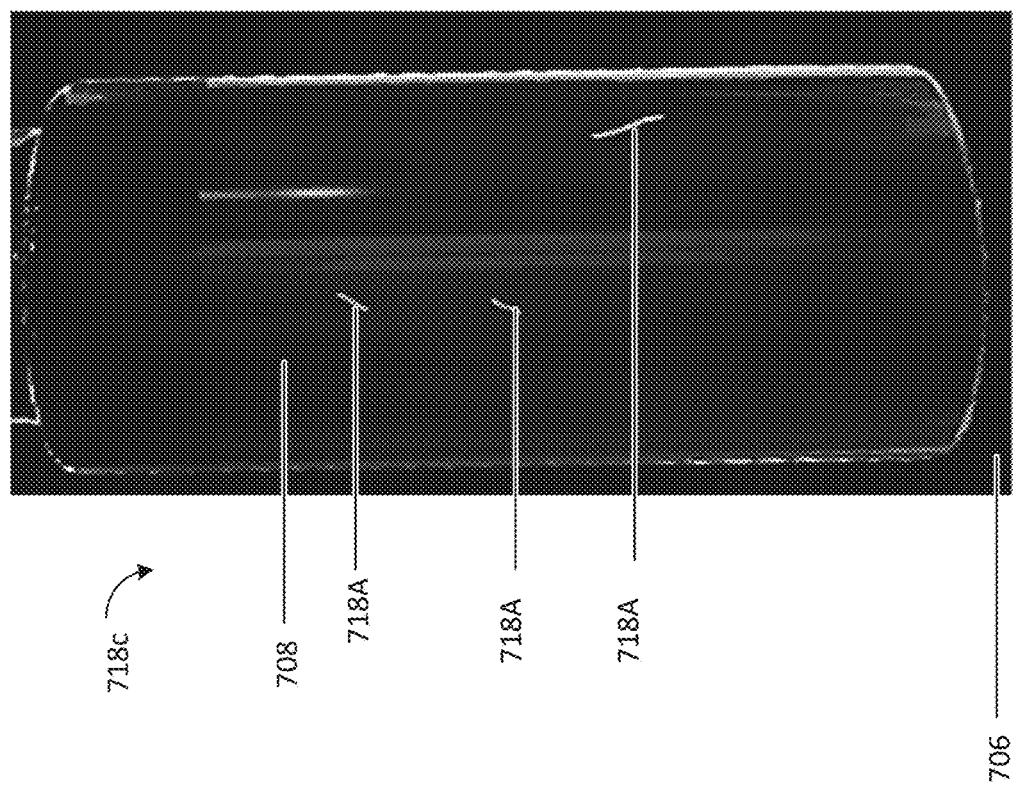
FIG. 7K illustrates a container having fibers assigned to be first visual indicator fibers illustrated as in front of a second background generated in a visual inspection simulation generated by an example virtual reality system, according to yet another example embodiment of the present disclosure.
Figure 7N:
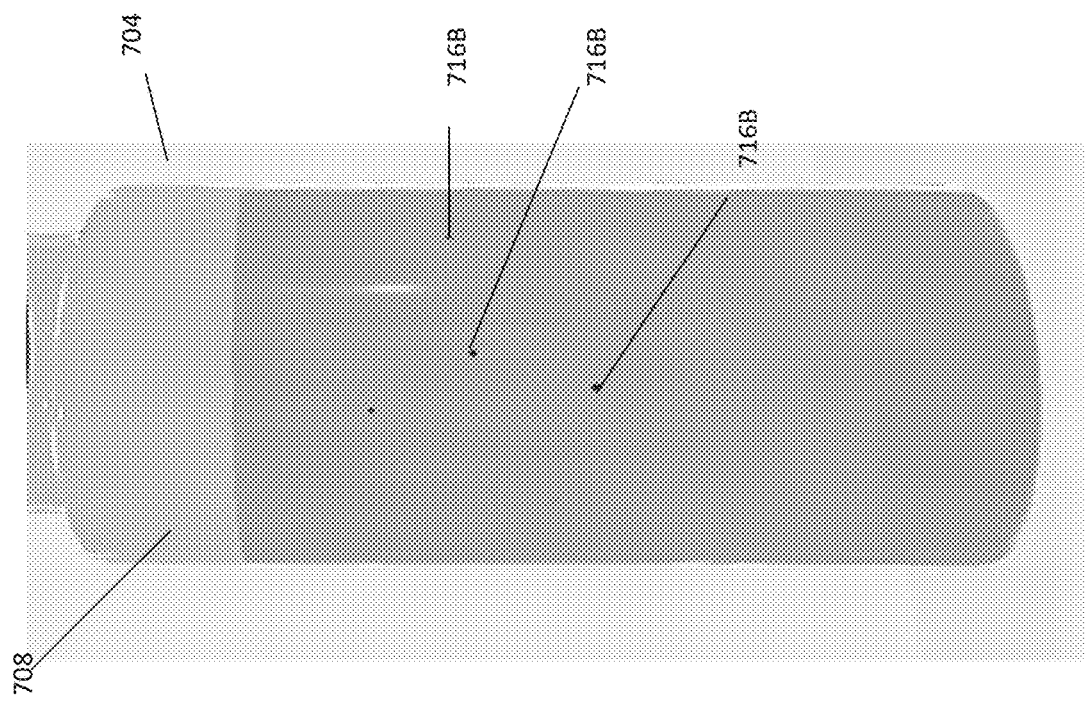
FIG. 7N illustrates a container having particles assigned to be second visual indicator particles illustrated as in front of a first background generated in a visual inspection simulation generated by an example virtual reality system, according to yet another example embodiment of the present disclosure.
Figure 7M:
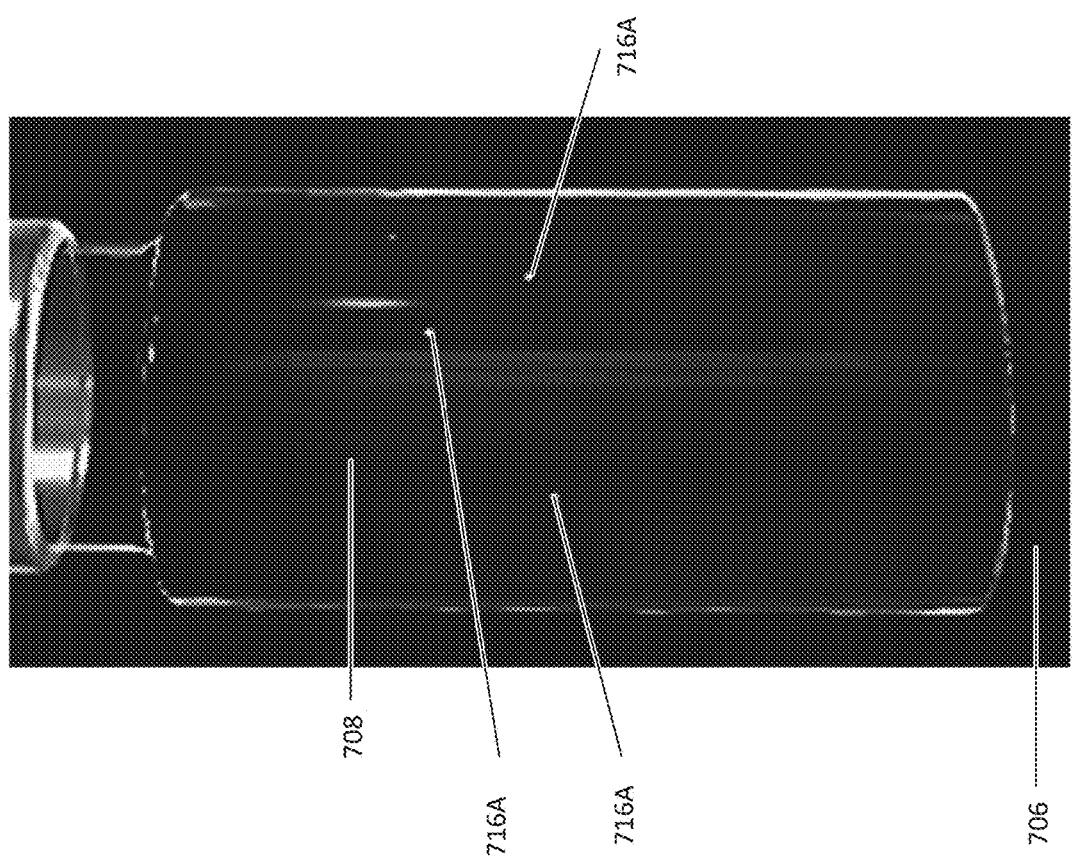
FIG. 7M illustrates a container having particles assigned to be first visual indicator particles illustrated as in front of a second background generated in a visual inspection simulation generated by an example virtual reality system, according to yet another example embodiment of the present disclosure.
Figure 7O:
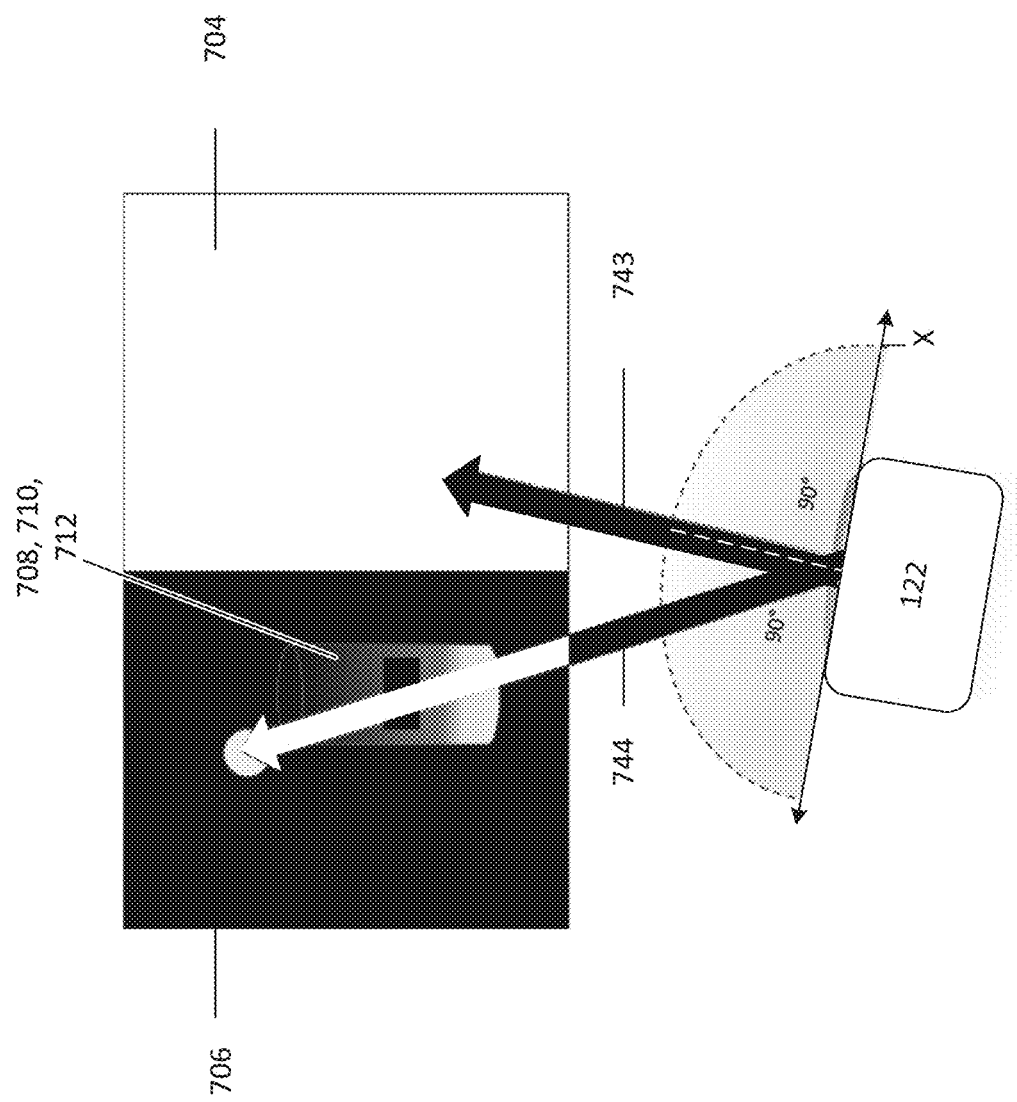
FIG. 7O illustrates a schematic view of a container observed in front of a second background generated in a visual inspection simulation generated by an example virtual reality system, according to yet another example embodiment of the present disclosure.
Figure 7P:
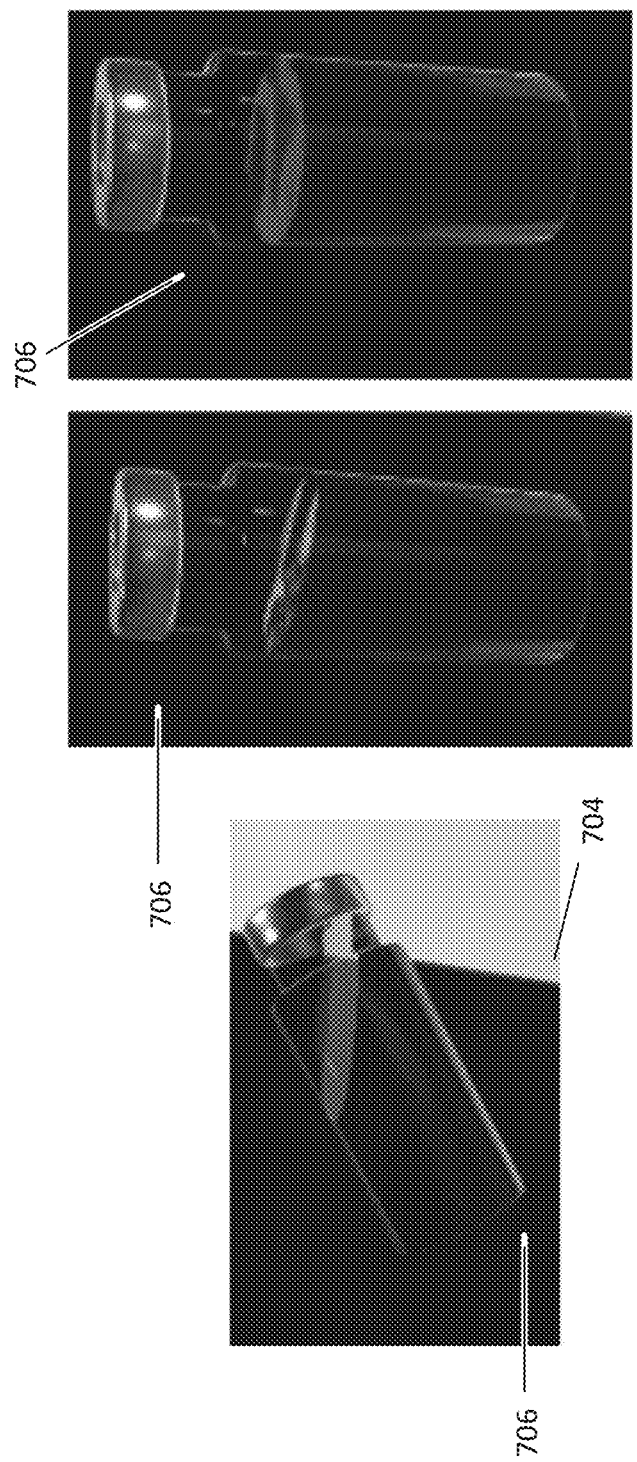
FIG. 7P illustrates a view of liquid sloshing in a container in a visual inspection simulation generated by an example virtual reality system, according to yet another example embodiment of the present disclosure.
Figure 7Q:
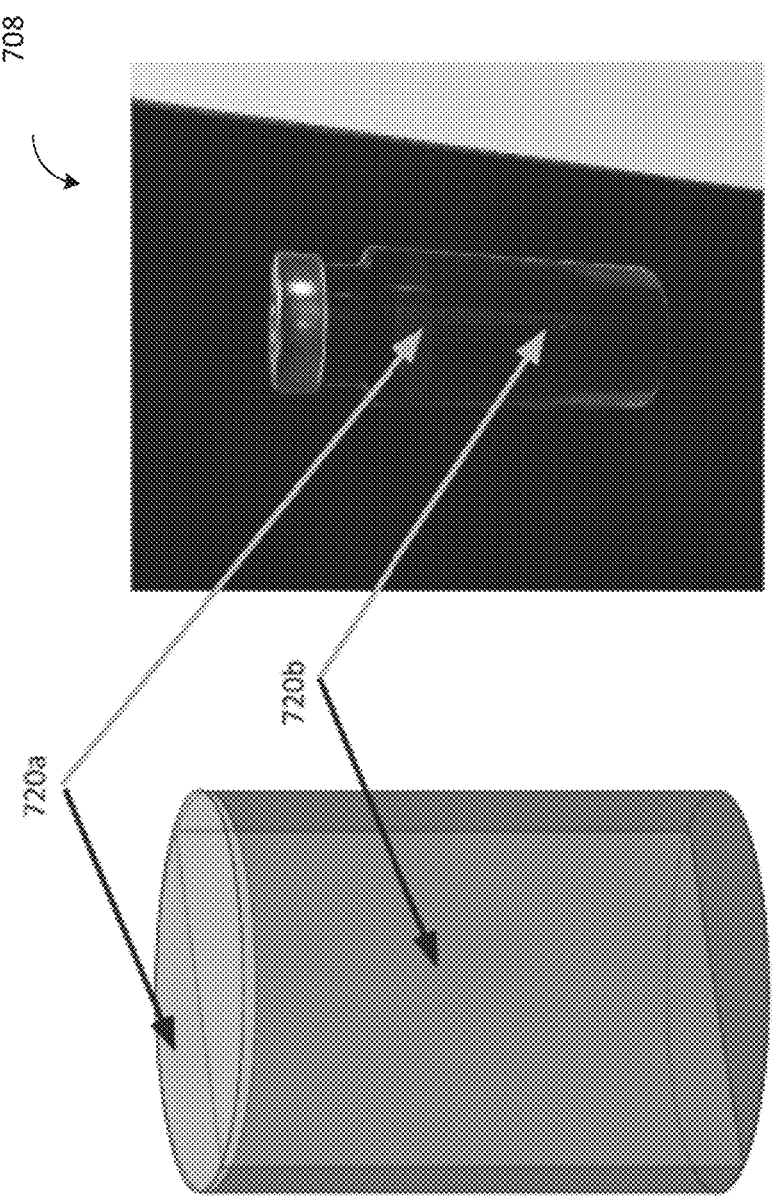
FIG. 7Q illustrates two-dimensional (2D) surfaces that are assigned by a processor to present an image to simulate a liquid top surface and a liquid side surface in a container in a visual inspection simulation generated by an example virtual reality system, according to yet another example embodiment of the present disclosure.
Figure 7R:
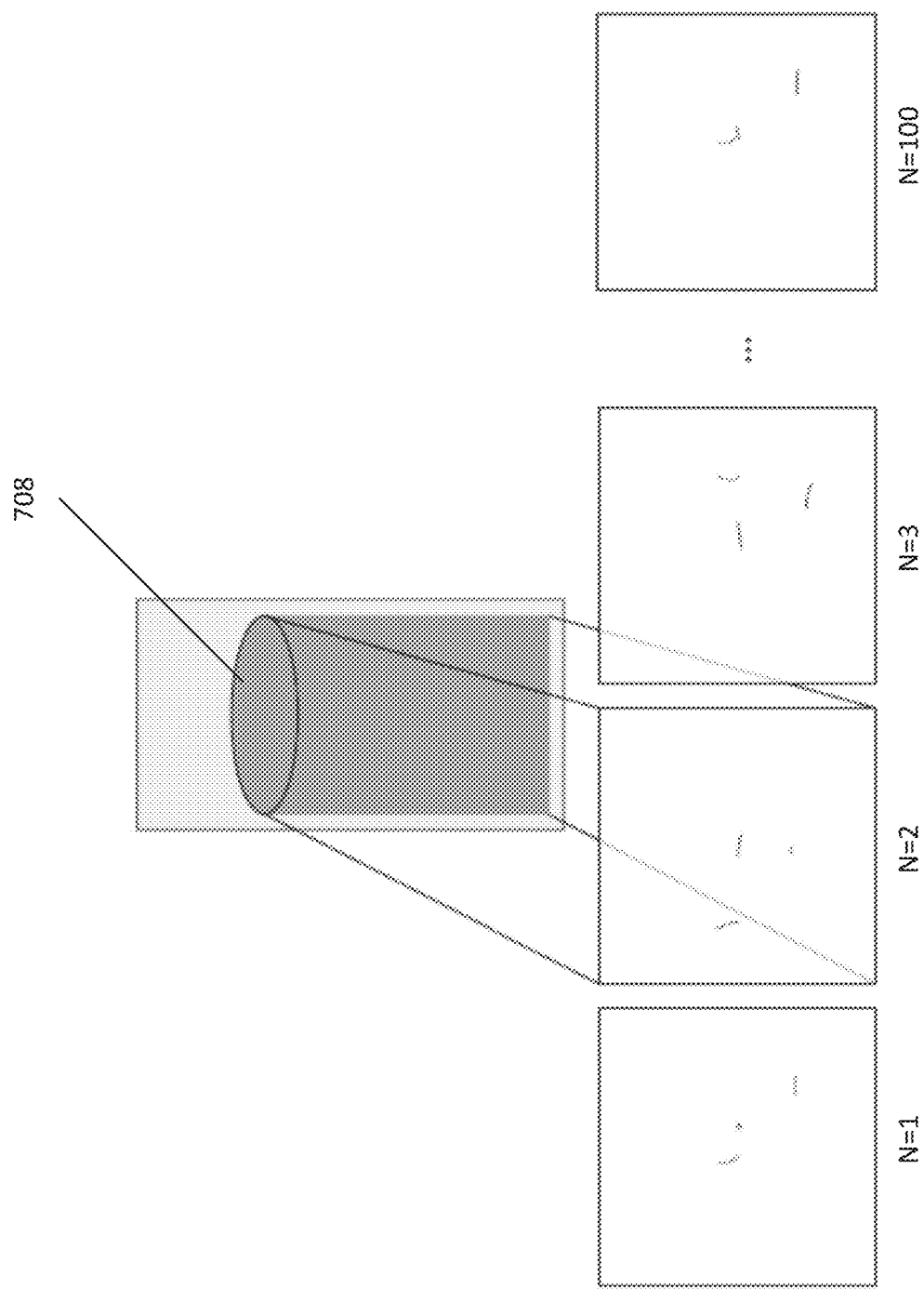
FIG. 7R illustrates a series of images of fibers from a sequence of rotation images in a visual inspection simulation generated by an example virtual reality system, according to yet another example embodiment of the present disclosure.
Figure 7S:
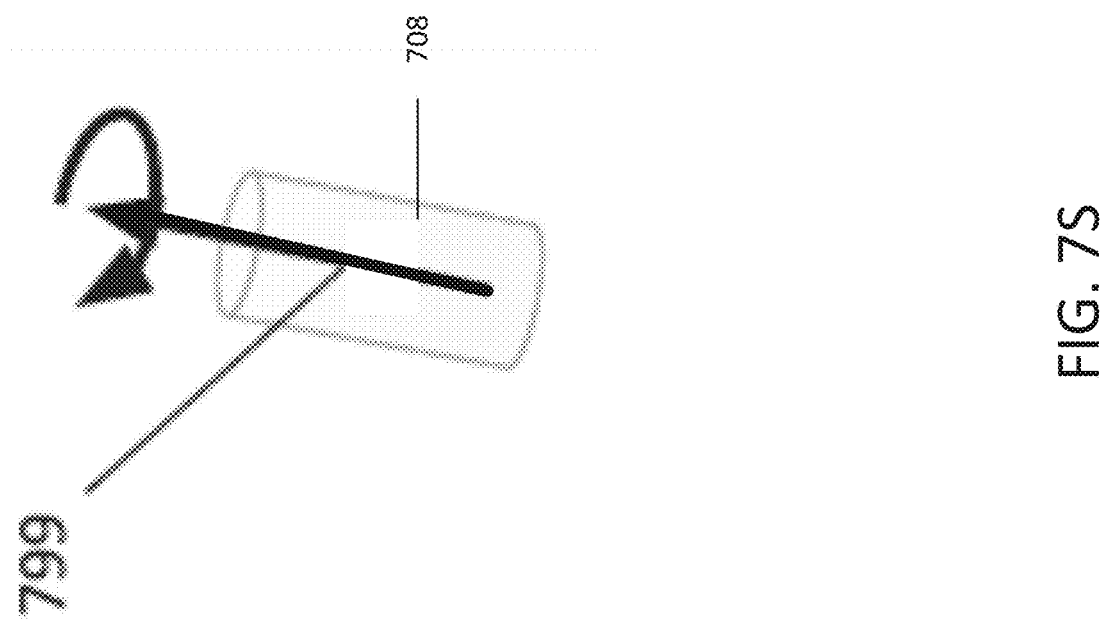
FIG. 7S illustrates a rotation vector of a container in a visual inspection simulation generated by an example virtual reality system, according to yet another example embodiment of the present disclosure.
Figure 7T:
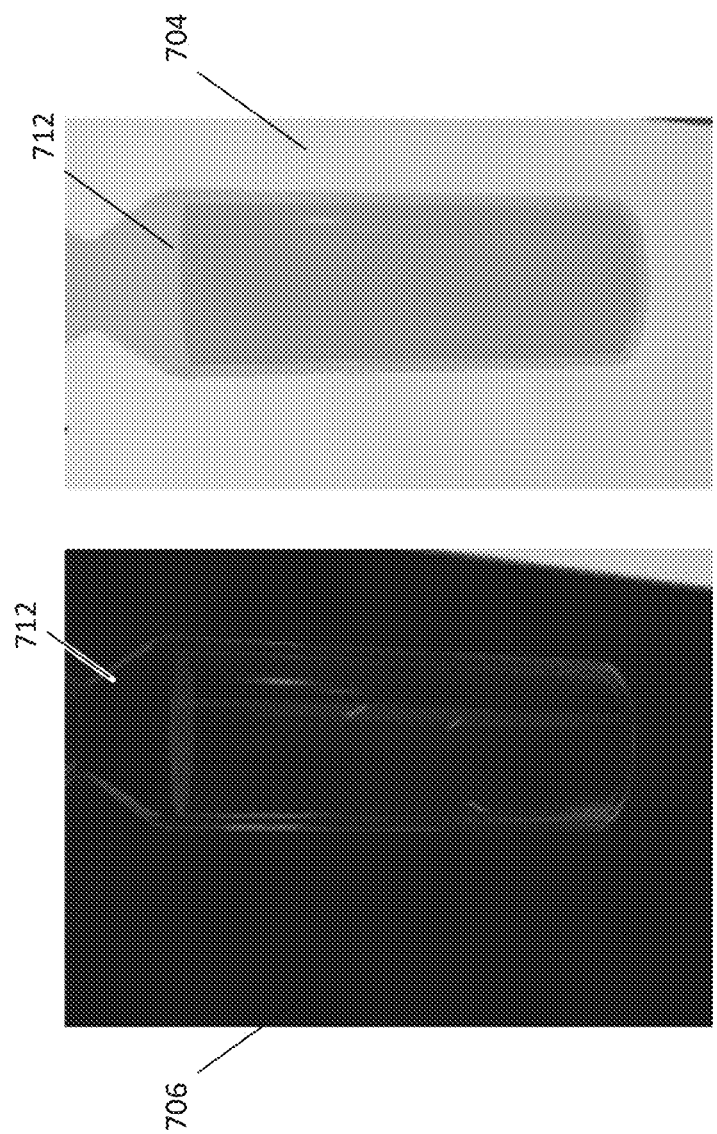
FIG. 7T illustrates first indicator fibers in front of both a second and first background in a visual inspection simulation generated by an example virtual reality system, according to yet another example embodiment of the present disclosure.
Figure 8A:
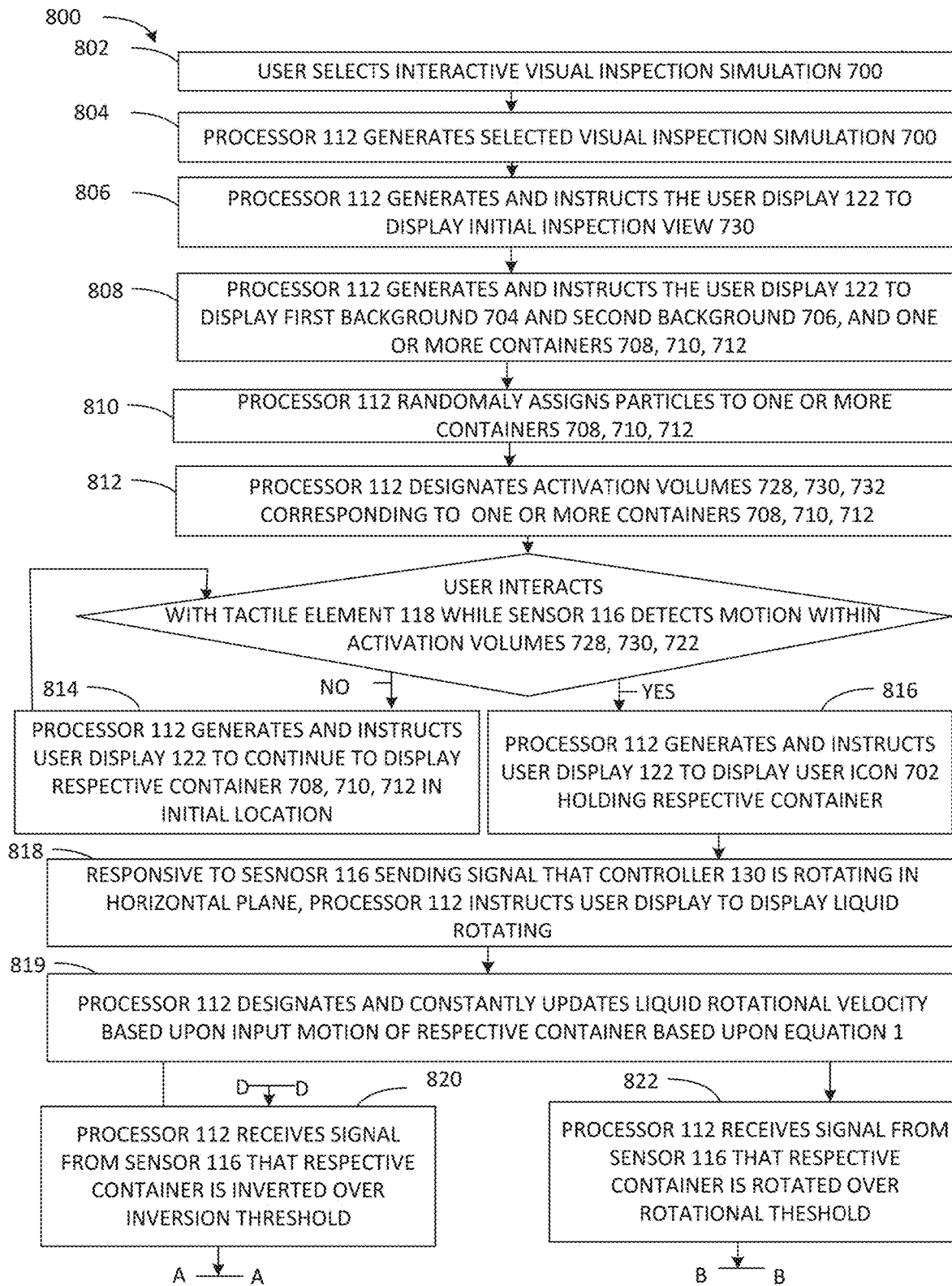
FIG. 8A is a schematic diagram of a method 800 of using a selected visualization simulation generated by an example virtual reality system, according to one example embodiment of the present disclosure.

As illustrated in FIG. 8A, a method 800 of use of the virtual reality system 100 with the interactive visual inspection simulation 700 is illustrated (see FIGS. 7A-7T). At 802, the processor 112 receives a signal indicating the user has selected the interactive visual inspection simulation 700 (see FIG. 7B). At 804, the processor 112 generates the visual inspection simulation 700. At 806, the processor 112 generates and instructs the user display 122 to display an initial visual inspection view 730. At 808, the processor 112 generates and instructs the user display 122 to display a first background 704 and a second background 706, and one or more containers 708, 710, 712 (see FIGS. 7B-7E). At 810, the processor 112 randomly assigns particles 716, glass shards 715, and/or fibers 718 to one or more containers 708, 710, 712. In one example embodiment, the processor 112 assigns the particles 716 as a first visual indicator particles 716A (e.g., white), a second visual indicator particles 716B (e.g., black), glass shards 715 (see FIG. 7J), first visual indicator fibers 718A (e.g., white), and/or second visual indicator fibers 718B (e.g., black) to the one or more containers 708, 710, 712 (see FIGS. 7K-7L). In one example embodiment, the processor 112 assigns particles 716, glass shards 715, and/or fibers 718 to between 30% to 70% of the total number of containers to be presented to the user, the remaining containers are designated as having no contaminations. In one embodiment, the one or more containers 708, 710, 712 comprise a vial 708, a fluid bag 710, and an ampule 712, wherein the container the controller 130 has been assigned by the processor 112 as interacting with will be referred to as the respective container. At 812, the processor 112 designates activation volumes 728, 730, 732 corresponding to the one or more containers 708, 710, 712, respectively (see FIGS. 7B-7E).

In one example embodiment, the sensor 116 sends a signal to the processor 112 that the controller 130 is within one of the activation volumes 728, 730, 732. The activation volumes 728, 730, 732 comprise a Cartesian coordinate system defining an activation distance (e.g. between 6 inches to 12 inches) of the container 708, 710, 712 of interest. The activation distance defines a three-dimensional volume that extends along x, y, and z axes. Steps 804-812 may be performed in any order, and/or may be performed simultaneously.

In one example embodiment, the activation volumes 728, 730, 732 comprise three dimensional volumes radiating out along x, y, and z axes from a central location (coordinates 0,0,0) wherein the respective container 708, 710, 712 is located, or a center point of the respective container. In this embodiment, the activation volumes 728, 730, 732 extend between 1 inch to about 7 inches along the x axis, between 1 inch to about 7 inches along the y axis, and/or between 1 inch to about 7 inches along the z axis, wherein the volume defined within comprises the respective activation volumes. Inches in space is based upon perceived distance by the user.

At 814, responsive to the user not interacting with the tactile element 118 and/or the sensor 116 not detecting motion within the activation volume 728, 730, 732, the processor instructs the user display 122 to maintain presentation of the respective container 708, 710, 712 in its initial position. In one example embodiment, one of the one or more types of containers 709, 710, 712 are displayed per simulation. In another example embodiment, two or more of the one or more types of containers 708, 710, 712 are displayed per simulation.

At 816, responsive to the user interacting with the tactile element 118 and the sensor 116 detecting motion within the activation volume 728, 730, 732, the processor 112 instructs the user display 122 to display a user icon 702 (e.g., same or similar to the user icons 302, and 502, described above) holding the respective container 708, 710, 712. In another example embodiment, no user icon or hand is shown, the processor 112 instructs the user display 122 to display the respective container 708, 710, 712 following the controller 130 motion without showing a hand icon responsive to interaction with the tactile element 118 and sensor 116 sending a signal to the processor 112 that motion has been detected within the activation volume 728, 730, 732.

As illustrated in model 722 of FIG. 7F, a single point mass 742 on the mass spring 740 with the lateral damper 736 is virtually attached to a fixed point 738 in the center of the container 708, 710, 712. As the processor 112 receives an input from the sensor 116 that the container 708, 710, 712 has altered its container orientation 724 (see FIG. 7A), a liquid top surface 720a is generated and drawn perpendicular to a vector drawn from the mass 742 to the center of the fixed point 738.

Responsive to the processor 112 receiving an input from the sensor 116 that the container 708, 710, 712, having been assigned to move with motion of the controller 130, is moved to one side, the mass 742 will swing back and forth and then settle again. As the processor 112 generates and instructs the user display 122 to display the liquid top surface 720a as following the orientation of the mass 742, the processor instructs the user display to display a liquid 720 (e.g.; the liquid in the container) to appear to be sloshing (see an example sloshing progression in FIG. 7P). The liquid top surface 720a and a liquid side surface 720b are not three dimensional, but rather 2D surfaces. The processor 112 instructs the user display 122 to display the liquid top surface 720a and the liquid side surface 720b as constantly facing a line of site 743 (see FIGS. 7Q and 7I).

In one example embodiment, an image 714 in FIG. 7H is used as a normal map for the texture applied to the liquid surface 720a, thereby giving a flat surface the appearance of having ripples. The greater the velocity of mass 742 relative to the respective container, the greater the Normal component of the surface plane is increased. In another example embodiment, the image 717 is illustrated as defining a vertical plane (e.g., the surface that the particles 716, glass shards 715, and/or the fibers 718 are drawn on). In one example embodiment, the image 717 comprises a ripple image illustrated in FIG. 7H is a texture that the processor 112 instructs the user display 122 to display on a top surface of the liquid 720.

At 818, responsive to sensor 116 sending a signal that the controller 130, the respective container having been assigned to move with motion of the controller 130, is rotating in a horizontal plane as shown in FIG. 7G, the processor instructs the user display 122 to display the liquid rotating (e.g., swirling), and responsive to the respective container being assigned particles 716, glass shards 715, and/or fibers 718, the user displays any air bubbles, glass shards, fibers, and/or particles contained in the liquid as rotating with the liquid. Responsive to the sensor 116 sending a signal that the controller 130 has stopped moving to the processor 112, the processor instructs the user display 122 to display the liquid 720 still rotating for a momentum duration. In one example embodiment, the momentum duration is between 1 second and about 4 seconds. Responsive to the respective container being displayed as being held still (e.g., the respective container is static), while the liquid is being displayed as still moving, visibility of particles 716, glass shards 715, fibers 718 and/or air bubbles moving relative to the container body is greatly increased. The mechanics of the liquid rotation and display as generated by the processor 112 of particles 716, glass shards 715, fibers 718 and/or air bubbles are described below.

Figure 8B:
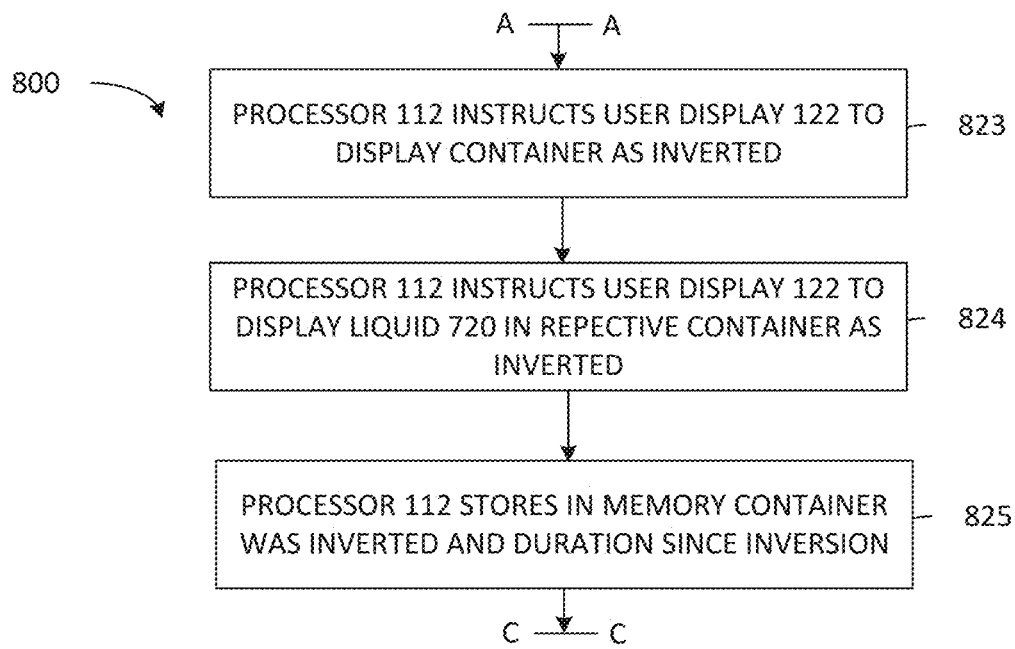
FIG. 8B is a schematic diagram of a method 800 of using a container inversion process in a selected visualization simulation generated by an example virtual reality system, according to one example embodiment or the present disclosure.

In this example embodiment, the processor 112 instructs the user display 122 to make the particles 716, glass shards 715, and/or fibers 718 visible responsive to the respective container being inverted over an inversion threshold, as described below. Inversion over an inversion threshold mimics simulating particles 716, glass shards 715, and/or fibers 718 that may have been stuck to an underside of a top of the respective container, and therefore would not be visible as the liquid 720 is swirled prior to inversion. At 820, the processor 112 receives a signal from the sensor 116 that the respective container (e.g., the container that the user icon 702 is holding) is inverted over an inversion threshold. In one example embodiment, the inversion threshold is a rotation of the respective container over 155 degrees, either clock-wise or counter-clockwise, and returning to a non-inverted state (e.g., an initial orientation). Steps 814, 816-820 can be done in any order. Continuing at section line A-A of FIG. 8B, at 823, the processor 112 instructs the user display 122 to display the respective container as inverted. At 824, the processor 112 instructs the user display to display the liquid 720 in the respective container as inverted. At 825, the processor 112 stores in memory that the respective container was inverted and stores a time when the inversion occurred, to determine a duration since the inversion.

Once the respective container is inverted over the inversion threshold, and returned upright, any particles 716, glass shards 715, and/or fibers 718 assigned to the respective container are instructed by the processor 112 to be displayed as visible by the user display 122. The processor 112 instructs the user display 122 to display particles 716, glass shards 715, fibers 718 end/or air bubbles on plane 720b, which as shown in FIG. 7I is continuously oriented to be perpendicular to the line of site 743 of a user viewing the user display.

Responsive to the respective container being held in front of a background (e.g., first or second background 704, 706) with contrasting color to that of the particle or the fiber, the processor 112 will instruct the user display 122 to display the particle or fiber as visible. For example, the processor 112 would instruct the user display 122 to display the first visual indicator particles 716A (e.g., white) and the first visual indicator fibers 718A. (e.g., white) as visible in front of the second background 706 (e.g., black) and the second visual indicator particles 716B (e.g., black), and the second visual indicator fibers 718B (e.g., black) as visible in front of the first background 704 (e.g., white) (see FIG. 7T).

Responsive to the respective container being held in front of a background (e.g., first or second background 704, 706) that lacks a contrasting color to that of the particle or the fiber, the processor 112 will instruct the user display 122 to display the particle or fiber as nearly invisible or invisible. For example, the processor 112 would instruct the user display 122 to display the first visual indicator particles 716A (e.g., white) and the first visual indicator fibers 718A (e.g., white) as invisible in front of the first background 704 (e.g., white) and the second visual indicator particles 716B (e.g., black) and the second visual indicator fibers 718B (e.g., black) as invisible in front of the second background 706 (e.g., black) (see FIG. 7T).

In one example embodiment, the processor 112 instructs the user display 122 to display the air bubbled as visible in the liquid 720 when a rotational velocity of the liquid (variable liquid rotational velocity calculated below in Equation 22) exceeds a rotational threshold. In one example embodiment, the rotational threshold is between 0.1 to about 1 revolutions per second. In one example embodiment, the rotational threshold is 0.5 revolutions per second. Responsive to the processors 112 determining that the liquid rotational velocity has dropped below the revolution threshold, the processor 112 will instruct the user display 122 to display the air-bubbles rising (e.g., in direction indicated by arrow B in FIG. 7G) and then disappear after a bubble duration. In one example embodiment, the bubble duration is between 2 seconds to about 6 seconds. In another example embodiment, the bubble duration is about 4 seconds. In yet another example embodiment, the processor 112 instructs the user display 122 to display the bubbles as visible after inversion over the inversion threshold.

Figure 8C:
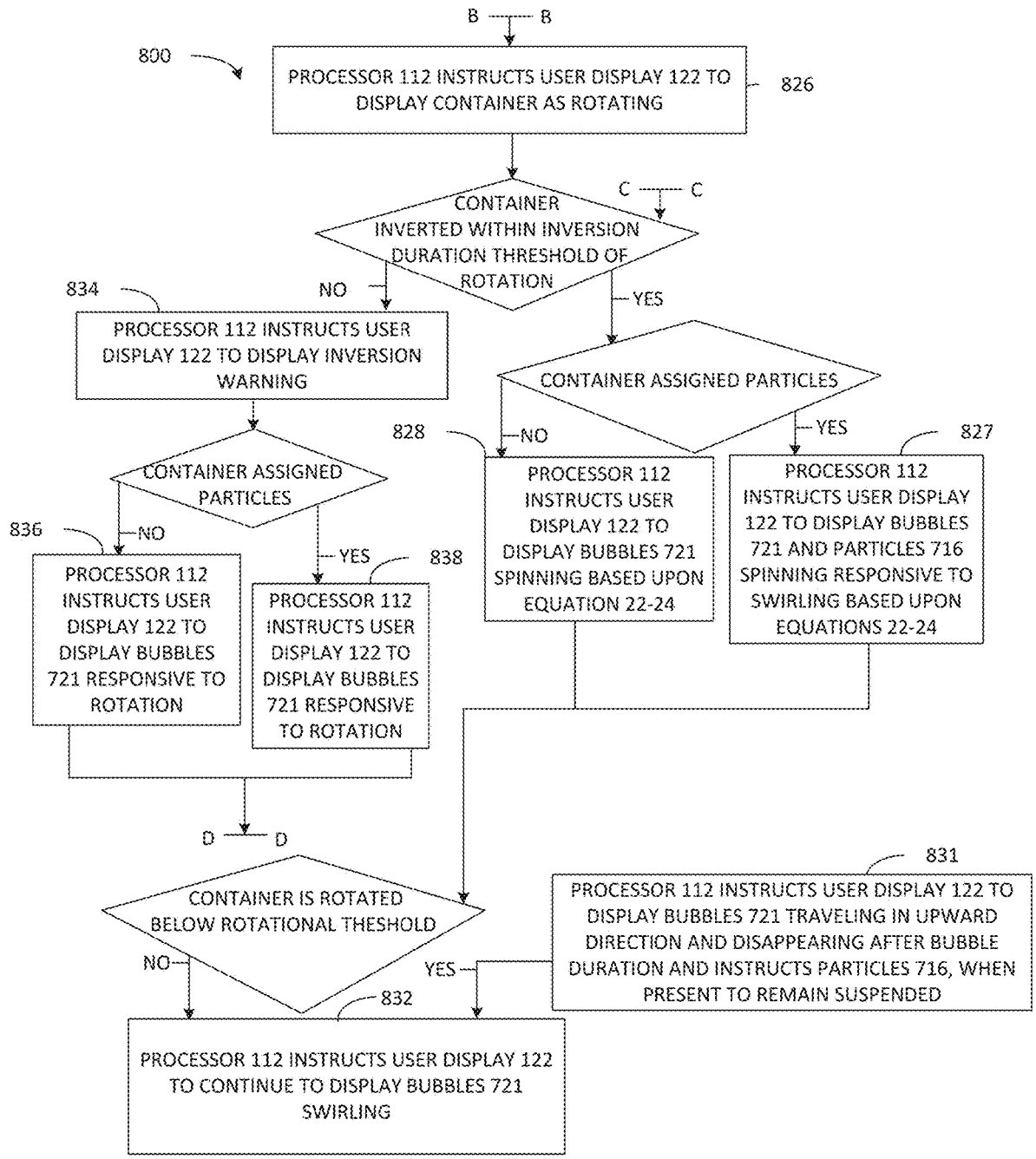
FIG. 8C is a schematic diagram of a method 800 of using a container rotation process and generating bubbles or particles within a container in a selected visualization simulation generated by an example virtual reality system, according to one example embodiment of the present disclosure.

At 822, as illustrated in FIG. 8A, the processor 112 receives a signal from the sensor 116 that the respective container is being rotated such that liquid rotation velocity exceeds the rotational threshold. Continuing at section line B-B of FIG. 8C, at 826, the processor 112 instructs the user display 122 to display the respective container as being rotated. At 834, responsive to the respective container not being inverted over the inversion threshold within in an inversion duration threshold of the rotation, the processor 112 instructs the user display 122 to display an inversion warning. At 836 and at 838, responsive to the respective container having been assigned particles 716 and/or fibers 718 (see FIG. 7J) or not assigned particles and/or fibers, the processor 112 instructs the user display 122 to display bubbles 721 responsive to the rotation.

At 832, responsive to the respective container not being rotated above the rotational threshold for a gravity duration, the processor 112 instructs the user display 122 to continue to display the bubbles 721 swirling as indicated by Equations 22-24. At 832, responsive to the container being rotated below the rotational threshold for a gravity duration, the processor 112 instructs the user display 122 to display the bubbles 721 traveling in upward direction and disappearing after a bubble duration and instructs particles 716 and/or fibers 718, when present, to remain suspended. The bubbles 721 rotate more slowly as indicated by Equations 22-24 when the rotation speed is decreased. In one example embodiment, responsive to the rotation of the respective container being sensed as rotating below the rotation threshold, the bubbles 721 will slow to a rising revolution speed and start to rise (along direction B)(see FIG. 7G). In one example embodiment, the rising revolution speed is between 0.25 to about 0.75 revolutions per second. In another example embodiment, the rising revolution speed is 0.5 revolutions per second. In one example embodiment, the gravity duration is between 2-5 seconds. In another example embodiment, the gravity duration is 4 seconds.

Figure 7U:
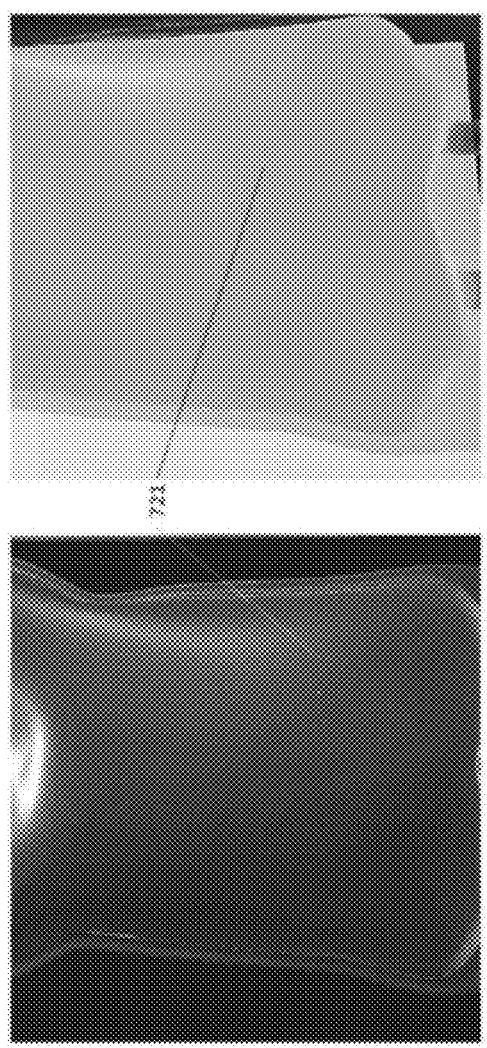
FIG. 7U illustrates air bubbles in front of a first and second backgrounds in a visual inspection simulation generated by an example virtual reality system, according to yet another example embodiment of the present disclosure.

In one example embodiment, the processor 112 instructs the user display 122 to display the particles 716 and fibers 718 (if assigned to be present) and air bubbles 721 as swirling by altering an image shown on the liquid side surface 720b to one from a sequence of 101 pre-rendered swilling particles or air bubbles (see FIG. 7R). In another example embodiment, the sequence may comprise between 50 to about 500 images. The processor 112 may instruct that several images from different sequences be stacked on top of each other, e.g., first visual indicator particles 716B (as shown in FIG. 7R) and air bubbles 721 (see FIG. 7M-7N, 7U) in order to display both the first visual indicator particle and the bubbles concurrently.

The image that the processor 112 instructs the user display 122 to display is calculated based upon a container orientation of the respective container and a calculated rotational velocity of the liquid 720, as illustrated in Equations 23-24 below.

$$\text{Image\_number} = \text{Container\_orientation}/360 \text{ degrees} * 100 + \text{liquid\_rotational\_velocity} * \text{speed\_constant} \quad \text{Equation 23}$$

If Image_number>100, then image_number=0

Else if image_number<0 then image_number=100    Equation 24

Wherein the Container_orientation is a degree of rotation from 0 degrees about container_up_vector 799, as illustrated in FIG. 7S, the liquid_rotational_velocity is calculated below with to Equation 22, and the speed constant is 1.0, wherein the speed constant is adjustable by the processor 112, wherein fluids having different viscosities are being displayed. Equation 22 provides views of the liquid 720 within the respective container from different angles, whether the controller 130 is rotating the respective container manually about container_up_vector 799 or the liquid is swirling within the respective container.

As the respective container is swirled/rotated by the controller 130, the mass's 742 rotational velocity in the container's UP direction (illustrated, for example, by arrow 799 in FIG. 7S), is used to generate the liquid_rotational_velocity which is used in a visualization state machine 722 of the processor 112 to simulate swirling particles 716, fibers 718 and/or air bubbles 721.

The mass's 742 rotational velocity being applied by the procesor 112 alone would generate spinning bf the particles 718 that would start and stop almost instantly (unlike liquid in the real world that exhibits momentum). Therefore, another variable (liquid_rotational_velocity) is calculated based on an "exponential moving average" of the mass's rotational velocity with alpha=0.6 (Equation 22). Thus, for every rotation computed, the liquid_rotational_velocity increases to 60% nearer to a target velocity (e.g., the actual velocity at which the mass 742 of the respective container 708, 710, 712 is rotating), thus creating a lag in a ramp up or down of the liquid rotational velocity, and simulating liquid with realistic rotational momentum.

$$\text{liquid\_rotational\_velocity} = \text{mass\_rotational\_velocity} [\text{dot product}] \text{container\_up\_vector} * 0.6 + \text{liquid\_rotational\_velocity\_0} * 0.4 \quad \text{Equation 22}$$

Wherein mass_rotational_velocity [dot product] container_up_vector calculates the rotational velocity of the mass abbot the container_up_vector. 0.6 and 0.4 are constants that affect the ramp up or ramp down speed, and can be adjusted by the processor 112 to better simulate liquids 720 with different viscosities.

The processor 112 assigns observed or not observed to each container 708, 710, 712. As illustrated in FIG. 7O, a respective container will be assigned as observed by the processor 112 responsive to an input from the sensor 114 that an observation my 744 is intersecting at least one of the first or second backgrounds 704, 706 and that the observation ray 744 is within a degree threshold (e.g., within 90 degrees) of the line of sight 743 (horizontally or vertically). The observation ray 744 and the line of sight 743 are identified based upon an input orientation of the user display 122 by the sensor 114. The input from the sensors 114 allows peripheral vision of the user to qualify as observed. This design permits users with bi- or trifocals to successfully inspect the containers 708, 710, 712.

In an example embodiment, a respective container will be assigned as observed responsive to the input front the sensor 114 that the observation ray 744 is intersecting at least one of the first or second backgrounds 704, 706 over a viewing duration (e.g., 5 seconds). Responsive to the sensor 114 indicating that the observation ray 744 has left both of the first or second backgrounds 704, 706, the processor 112 pauses a timer timing the viewing duration. Responsive to the observation my 744 having left both of the first or second backgrounds 704, 706 over an observation threshold (e.g., 1 second) the timer resets, and the full viewing duration will be observed prior to the processor 112 assigning the respective container as observed.

In an example embodiment, a user determines whether a defect is present in the respective container and which defect is present (e.g., the first visual indicator particles 716a, the first visual indicator fibers 718a, the second visual indicator particles 716b, the second visual indicator fibers 718b, and/or the glass shards 715). The visual inspection simulation 700 teaches good inspection technique (invert the container, swirl, stop twirling, hold in front of one background for 5 seconds, swirl, stop swirling, hold in front of the other background for 5 seconds) in order to determine the defect. If a container has light particles, those particles will be nearly invisible if the student only observes the container in front of the white background. Also, if the student does not swirl a container with glass shards, they may be nearly invisible in front of both backgrounds when held steady, as the glass particles appear invisible from some orientations as shown in FIG. 7J. If a student does not hold a container long enough, the student may incorrectly think air bubbles are light particles.

This interactive visual inspection simulation 700 and method provides a method for simulating particles 718 in fluid-filled containers 708, 710, 712 that mimic real particles in fluid without the need, and attendant cost of computing power, for complex fluid dynamics modeling. The interactive visual inspection simulation 700 mimics the dark and light particles 718a, 718b (e.g, fibers, particles, and/or glass shards), and air bubbles 721 that may occur in container such as vials 708, bags 710, and/or ampoules 712 during their manufacture and filling of said containers. Advantageously, as this interactive visual inspection simulation 700 forgoes complex fluid dynamics modeling, it may be run in real time on a typical gaming computer system in a virtual reality experience. Further, pre-rendering the images into 2D images sequences rather than rendering 3D models in real-time enables the use of higher fidelity modeling, lighting and behavior mechanics than would be possible in real-time in virtual reality.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities of actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. In one non-limiting embodiment the terms are defined to be within for example 10%, in another possible embodiment within 5%, in another possible embodiment within 1%, and in another possible embodiment within 0.5%. The term "coupled" as used herein is defined as connected or in contact either temporarily or permanently, although not necessarily directly and not necessarily mechanically. A device or structure that is "configured" in a certain way is configured in at least that way, but may also be configured in ways that are not listed.

To the extent that the materials for any of the foregoing embodiments or components thereof are not specified, it is to be appreciated that suitable materials would be known by one of ordinary skill in the art for the intended purposes.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A non-transitory computer readable medium storing instructions executable by an associated processor to perform a method for implementing a bacteria streaking simulation comprising:
   generating a three-dimensional initial view based upon a view selection input by a user;
   sending instructions to present the initial view to a user display of a headset, the user display comprised within the headset;
   receiving an input from a controller comprising at least one sensor indicating user movement within the initial view;
   accessing memory to identify an assigned status of a loop; and
   responsive to the loop being coupled to a user icon within the initial view, storing a pattern of interaction between the loop and a streaking plate comprised within the initial view, storing the pattern comprising:
      generating a series of waypoints and connecting them to comprise the pattern.

2. The method of claim 1, wherein responsive to the pattern of interaction overlapping one or more existing waypoints of one or more existing patterns, assigning an altered bacterial concentration to the loop based upon the assigned value of the one or more existing waypoints and the assigned bacterial concentration of the loop at the location of the overlap.

3. The method of claims 2, and storing the series of waypoints and their assigned bacterial concentrations.

4. The method of claim 1 assigning a decreasing bacterial concentration to the loop, wherein the concentration of the loop at the location of a waypoint creation is assigned to the waypoint, wherein each progressive waypoint within the series of waypoints being created by the loop has a decreasing bacterial concentration.

5. The method of claim 1, generating a first rectangle extending toward a previous waypoint in the series of waypoints and a second rectangle extending toward a next waypoint in the series of waypoints.

6. The method of claim 3, calculating a cell potential of the first and second rectangles based upon the assigned bacterial concentration of the waypoint, and randomly assigning cell placement with the first and second rectangles based upon the cell potential.

7. The method of claim 4, simulating bacterial growth on the streaking plate based upon the cell placement within the first and second rectangles.

8. A virtual reality system for providing a bacterial streaking simulation, the system comprising:
   a processing device having a processor configured to perform a predefined set of operations in response to receiving a corresponding input from at least one of virtual reality headset and at least one controller, the processing device comprising memory, wherein a three-dimensional initial view of the bacterial streaking simulation is stored, the initial view comprising a streaking plate, a heating element, and a loop;
   the processor instructs the initial view to be presented on a user display comprised within the headset;
   the at least one controller sends an input to the processor indicating the controller is moving within the initial view;
   the processor instructs the movement of the controller of the at least one controller be presented on the user display;
   responsive to an input from the controller, the processor assigns the loop to be controlled by movement of the controller;
   the controller sends an input indicating that the controller is moving and interacting with the streaking plate; and
   the processor generates and stores a pattern of interaction between the loop and the streaking plate, wherein the processor generates the pattern by assigning a exponentially decreasing bacterial concentration to the loop responsive to a distance traveled by said loop while interacting with the streaking plate, the processor generates a series of waypoints, wherein the bacterial concentration of the loop at the location of a waypoint creation is assigned to the waypoint , the processor instructs the user display to illustrate the waypoints as a line forming the pattern on the streaking plate.

9. The system of claim 6, responsive to the controller sending a signal to the processor that the loop as overlapped with an existing pattern, the processor assigns an altered bacterial concentration to the loop based upon the assigned value of the one or more existing waypoints and the assigned bacterial concentration of the loop at the location of the overlap.

10. The system of claim 6, wherein responsive to an input from the at least one controller indicating user movement within a loop activation volume corresponding to the loop of the initial view, the processor assigns the loop to be controlled by movement of the controller.

11. The system of claim 6, wherein the processor generates a first rectangle extending toward a previous waypoint in the series of waypoints and a second rectangle extending toward a next waypoint in the series of waypoints, the processor calculates a cell potential of the first and second rectangles based upon the assigned bacterial concentration of the waypoint.

12. The system of claim 9, the processor randomly assigns cell placement with the first and second rectangles based upon the cell potential.

13. The system of claim 10, the processor simulates bacterial growth on the streaking plate based upon the cell placement within the first and second rectangles.

14. The system of claim 11, responsive to the processor detecting the loop is interacting with a surface, the processor instructs the controller to provide haptic feedback responsive to being within a threshold distance of the surface.

15. A non-transitory computer readable medium storing instructions executable by an associated processor to perform a method for implementing a visual inspection simulation comprising:
   generating a three-dimensional initial view based upon a view selection input by a user;
   sending instructions to present the initial view to a user display of a headset, the user display comprised within the headset;
   receiving an input from a controller comprising at least one sensor indicating user movement within the initial view;
   accessing memory to identify an assigned status of a selected container of one or more containers;
   responsive to an input from the controller, the processor assigns the selected container to be controlled by movement of the controller;
   continuously generating a fluid flow pattern utilizing a visualization state machine, wherein a single point mass on a mass spring with a lateral damper is virtually attached to a fixed point in a center of the container.

16. The system of claim 13, responsive to the controller sending a signal to the processor that the selected container is within a first background, the processor having assigned particles to be first visual indicator particles instructs the user display to display the first visual indicator particles to be invisible or nearly invisible wherein the first background and the first visual indicator particles are assigned non-contrasting colors, and the processor having assigned particles to be second visual indicator particles instructs the user display to the display the second visual indicator particles to be visible wherein the first background and the second visual indicator particles are assigned contrasting colors.

17. The system of claim 13, responsive to particles being assigned to the selected container, the processor generates and instruct the user display to display a two-dimensional liquid side surface by displaying images of a sequence of image particles in various rotations.

18. The method of claim 13, responsive to receiving an input from the controller that the container moved in a defined direction, swinging the single point mass back and forth along the defined direction then settling the single point mass into an original position.

19. The method of claim 16, displaying a two-dimensional liquid top surface as following the orientation of the single point mass, wherein the liquid top surface is continually oriented to face a line of sight from the user display.

20. A virtual reality system for providing a visual inspection simulation, the system comprising:
   a processing device having a processor configured to perform a predefined set of operations in response to receiving a corresponding input from at least one of virtual reality headset and at least one controller, the processing device comprising memory, wherein a three-dimensional initial view of a visual inspection simulation is stored, the initial view comprising at least one container;
   the processor instructs the initial view to be presented on a user display comprised within the headset;
   the at least one controller sends an input to the processor indicating the controller is moving within the initial view;
   the processor instructs the movement of the controller of the at least one controller be presented on the user display;
   responsive to an input from the controller, the processor assigns a selected container of the at least one container to be controlled by movement of the controller;
   the controller sends an input indicating that the controller is moving the selected container; and
   the processor generates a continuous fluid flow pattern utilizing a visualization state machine, wherein the visualization state machine comprises a single point mass on a mass spring with a lateral damper virtually attached to a fixed point in a center of the container.

21. The system of claim 18, wherein the controller sends a signal to the processor that the container moved in a defined direction.

22. The system of claim 19, the processor swings the single point mass back and forth along the defined direction then has the single point mass return to an initial position, wherein the processor instructs the user display to display a two-dimensional liquid top surface as following the orientation of the single point mass, wherein the process instructs the user display to display the liquid top surface to be continually oriented to face a line of sight.

\* \* \* \* \*